United States Patent
Sugiyama et al.

(10) Patent No.: US 12,288,606 B2
(45) Date of Patent: Apr. 29, 2025

(54) REHABILITATION SYSTEM AND IMAGE PROCESSING APPARATUS FOR HIGHER BRAIN DYSFUNCTION

(71) Applicant: TECHLICO INC., Osaka (JP)

(72) Inventors: Takashi Sugiyama, Osaka (JP); Reo Sakamoto, Osaka (JP); Kimitaka Hase, Osaka (JP); Shingo Hashimoto, Osaka (JP)

(73) Assignee: TECHLICO INC., Osaka (JP)

( * ) Notice: Subject to any disclaimer, the term of this patent is extended or adjusted under 35 U.S.C. 154(b) by 806 days.

(21) Appl. No.: 17/424,329

(22) PCT Filed: Jan. 22, 2019

(86) PCT No.: PCT/JP2019/001869
§ 371 (c)(1),
(2) Date: Jul. 20, 2021

(87) PCT Pub. No.: WO2020/152779
PCT Pub. Date: Jul. 30, 2020

(65) Prior Publication Data
US 2022/0076803 A1 Mar. 10, 2022

(51) Int. Cl.
*G16H 20/70* (2018.01)
*G06T 19/00* (2011.01)
(Continued)

(52) U.S. Cl.
CPC ........... *G16H 20/70* (2018.01); *G06T 19/006* (2013.01); *G16H 10/60* (2018.01); *G16H 40/20* (2018.01); *G16H 80/00* (2018.01)

(58) Field of Classification Search
CPC ........ G16H 20/70; G16H 10/60; G16H 40/20; G16H 80/00; G16H 40/67; G16H 50/30;
(Continued)

(56) References Cited

U.S. PATENT DOCUMENTS 5,997,439 A 12/1999 Ohsuga et al.
6,339,721 B1 1/2002 Yamazaki et al.
(Continued)

FOREIGN PATENT DOCUMENTS

CN 107308638 A 11/2017
CN 109011097 A 12/2018
(Continued)

OTHER PUBLICATIONS

Taguchi et al., "3. Effect of number erasure task using mixed reality technology on cognitive function", Outstanding Presentation Award Session, 1st day 1st venue 17: 10-18: 10, Oct. 28, 2017, total 4 pages; English translation.
(Continued)

*Primary Examiner* — Robert W Morgan
*Assistant Examiner* — Liza Tony Kanaan
(74) *Attorney, Agent, or Firm* — RANKIN, HILL & CLARK LLP

(57) ABSTRACT

The present invention is a rehabilitation system for performing rehabilitation of higher brain dysfunction, and includes: an image processing apparatus that executes an app for presenting a patient a problem for rehab based on an image using virtual reality, augmented reality, or mixed reality and stores the patient's problem solution record as rehab record information; a practitioner-side terminal that receives the rehab record information from the image processing apparatus; a server that saves the rehab record information transmitted from the practitioner-side terminal; and a doctor-side terminal that receives the rehab record information from the server and displays the state of rehabilitation performed for the patient on the basis of the rehab record information.

40 Claims, 38 Drawing Sheets

(51) Int. Cl.
  *G16H 10/60* (2018.01)
  *G16H 40/20* (2018.01)
  *G16H 80/00* (2018.01)
(58) Field of Classification Search
  CPC ...... G16H 40/63; G06T 19/006; A61B 5/744; A61B 2505/09; A61B 5/0022; A61B 5/168; A61B 5/1114; A61B 5/163; A61B 5/4848; A61B 5/6803; A61B 5/7445; A61B 5/4082; A61B 5/4088; A61B 5/4064
  See application file for complete search history.

(56) References Cited

U.S. PATENT DOCUMENTS

| | | | |
|---|---|---|---|
| 2004/0006287 A1* | 1/2004 | Epley | A61B 5/11 600/595 |
| 2006/0161218 A1* | 7/2006 | Danilov | A61B 5/682 607/45 |
| 2006/0241718 A1* | 10/2006 | Tyler | G06F 3/015 607/45 |
| 2007/0050715 A1 | 3/2007 | Behar | |
| 2010/0016730 A1 | 1/2010 | Tanaka et al. | |
| 2012/0214143 A1 | 8/2012 | Severson et al. | |
| 2016/0310059 A1 | 10/2016 | Faubert et al. | |
| 2017/0039718 A1* | 2/2017 | Kotake | G06T 7/73 |
| 2017/0196482 A1 | 7/2017 | Matsumoto et al. | |
| 2019/0247719 A1 | 8/2019 | Hara | |

FOREIGN PATENT DOCUMENTS

| | | |
|---|---|---|
| JP | 8-280762 A | 10/1996 |
| JP | 9-120464 A | 5/1997 |
| JP | 10-151162 A | 6/1998 |
| JP | 2000-126148 A | 5/2000 |
| JP | 2001-79050 A | 3/2001 |
| JP | 2005-143559 A | 6/2005 |
| JP | 2006-325740 A | 12/2006 |
| JP | 2007-267802 A | 10/2007 |
| JP | 2009-502335 A | 1/2009 |
| JP | 2011-110215 A | 6/2011 |
| JP | 2013-161315 A | 8/2013 |
| JP | 2014-506141 A | 3/2014 |
| JP | 2015-213539 A | 12/2015 |
| JP | 2015-228957 A | 12/2015 |
| JP | 2017-511891 A | 4/2017 |
| JP | 6200615 B1 | 9/2017 |
| JP | 2018-79308 A | 5/2018 |
| JP | 2018-185501 A | 11/2018 |
| JP | 6425287 B1 | 11/2018 |
| JP | 2018-195273 A | 12/2018 |
| JP | 2019-10441 A | 1/2019 |

OTHER PUBLICATIONS

International Search Report (ISR) dated Apr. 23, 2019 filed in PCT/JP2019/001869.
Japanese Office Action (JPOA) dated Nov. 11, 2020 for the corresponding Japanese Patent Application No. 2017-129815 and its English machine translation.
Japanese Office Action (JPOA) dated Mar. 24, 2021 for the corresponding Japanese Patent Application No. 2017-129815 and its English machine translation.
"About the start of "Rehamaru" service", Rehamaru, (website), https://rehamaru.jp/%E3%80%8C%E3%83%AA%E3%83%8F% E3%81%BE%E3%82%8B%E3%80%8D%E3%82%B5%E3%83% BC%E3%83%93%E3%82%B9%E9%96%8B%E5%A7%8B%E3% 81%AB%E3%81%84%E3%81%84%E3%81%A6/, Jun. 1, 2017, total 4 pages; English machine translatio.
"Contents Tokyo 2017 Opening, "VR /AR World" Report—Increasing Demonstrations of FiveSenses", Dospara Express, (web media), https://www.dospara.co.jp/express/vr/448493, Jun. 28, 2017, total 21 pages; English machine translation.
"Techlico Inc. of MR / VR contents and Kansai Medical College collaborate! Rehabilitation system "Rehamaru" using Hololens announced at the medical society", Rehamaru Press Release, (website), https://rehamaru.jp//www.rehamaru.jp, Oct. 20, 2017, total 5 pages; English machine translation.
"Rehabilitation system "Rehamaru" using Hololens announced at the Rehabilitation Medical Society", StartHome, (web media), https://home.kingsoft.jp/news/app/vrinside/126123.html, Oct. 20, 2017, total 9 pages; English machine translation.
"Prevention of dementia with MR technology Rehabilitation system of Kansai Medical College and others", MoguraVR News, (web media), https://www.moguravr.com/rehamaru-mr/, Oct. 24, 2017, total 7 pages; English machine translation.
"Rehabilitation system "Rehamaru" using MR technology announced at the Medical Society Techlico Inc.", Panora, (web media), https://panora.tokyo/42914/, Oct. 24, 2017, total 8 pages; English machine translation.
"Next-generation rehabilitation system "Rehamaru" announced by Techlico Inc. and Kansai Medical College", Dementia net, (web media), https://info.ninchisho.net/archives/26486, Oct. 25, 2017, total 7 pages; English machine translation.
"Breaking news! Excellent presentation award! 1st Autumn Meeting of the Rehabilitation Medical Society", Rehamaru, (website), https://rehamaru.jp/%E3%80%90%E9%80%9F%E5%A0%B1%EF% BC%81%E3%80%91%E5%84%AA%E7%A7%80%E6%BC%94% E9%A1%8C%E8%B3%9E%E5%8F%97%E8%B3%9E%EF%BC% 81%EF%BC%88%E7%AC%AC1%E5%9B%9E%E3%83%AA% E3%83%8F%E3%83%93%E3%83%AA%E3%83%86%E3%83% BC/, Oct. 31, 2017, total 4 pages; English machine translation.
"Our service "Rehamaru" was adopted for the 18th Ikeda Senshu Bank New Business Award", Rehamaru, (website), https://rehamaru.jp/ikeda-newbusiness/, Nov. 10, 2017, total 4 pages; English machine translation.
"Techlico announces rehabilitation system "Rehamaru" using Hololens in collaboration with Kansai Medical College at the medicao society -Launch of software services for dementia prevention and stroke care in Japan and overseas-", Innavi net, (web media), https://www.innervision.co.jp/products/release/20171202/, Dec. 2, 2017, total 4 pages; English machine translation.
"Rehamaru will be exhibiting at Medical Japan 2018 on Feb. 21 and 23!", Rehamaru, (website), http://rehamaru.ip/%E3%83%A1%E3% 83%87%E3%82%A3%E3%82%AB%E3%83%AB%E3%83%BB% E3%82%B8%E3%83%A3%E3%83%91%E3%83%B3%EF%BC% 92%EF%BC%90%EF%BC%91%EF%BC%98%EF%BC%88%EF% BC%92%E6%9C%88%EF%BC%92%EF%BC%91%E6%97%A5% EF%BD%9E%EF%BC%92/, Feb. 19, 2018, total 5 pages; English machine translation.
Medical Japan 2018, exhibition of Feb. 21, 2018; English machine translation.
"The News α", Fuji television broadcast, Feb. 26, 2018, total 6 pages; English machine translation.
International Innovation Conference HackOsaka2018 Startup showcase of Feb. 27, 2018; English machine translation.
"News Voice", MBS broadcast, of Feb. 27, 2018, total 6 pages; English machine translation.
"Health Sakai 21 Health Fair "Health promotion for a bright future"~From the old days to the present and the future" will be held,Sakai City Press Materials, Mar. 4, 2018, total 8 pages; English machine translation.
"MR and cognitive function improvement rehabilitation are fused. Combining the latest technology with the knowledge and resources of medical colleges", Kansai Medical University Press Release, (web media), http://www.kmu.ac.jp/news/laaes70000001d0v-att/ 20180405Press_Release_re.pdf, Apr. 5, 2018, total 12 pages; English machine translation.
HAT!! Kobe Health fair of Apr. 7, 2018, total 4 pages; English machine translation.
"Realistic virtual image overlay Cognitive function improvement Motivation stimulation like a game, Kansai Medical University",

(56) References Cited

OTHER PUBLICATIONS

Nishinippon Newspaper, (web media), https://www.nishinippon.co.jp/nnp/medical/article/408090/, Apr. 12, 2018, total 20 pages; English machine translation.
"Realistic virtual image overlay, cognitive function improvement/ Stimulate motivation like a game / Kansai Medical College", 47News, (web media), Apr. 12, 2018, total 4 pages; English machine translation.
"Realistic improvement of virtual image overlay cognitive function. Motivation stimulation like a game / Kansai Medical University", Kyodo News, (web media), Apr. 12, 2018, total 8 pages; English machine translation.
"Realistic improvement of virtual image overlay cognitive function Motivation stimulation like a game / Kansai Medical University", goo News, (web media), Apr. 12, 2018, total 5 pages; English machine translation.
"Realistic improvement of virtual image overlay cognitive function. Motivation stimulation like a game / Kansai Medical University", Fukuishinbun Online, (web media), Apr. 12, 2018, total 5 pages; English machine translation.
"Realistic improvement of virtual image overlay cognitive function. Motivation stimulation like a game / Kansai Medical University", Yamagata News Online, (web media), Apr. 12, 2018, total 3 pages; English machine translation.
"Spatial recognition of people with dementia Experience virtual reality on a goggle-type terminal", Kyoto News, (web media), Nov. 4, 2018, total 5 pages; English machine translation.
"Improve cognitive function with 3D images Development of new rehabilitation method", Asahi Shimbun Digital, (web media), https://www.asahi.com/articles/ASL4C5HZ3L4CPLBJ005.html, Apr. 12, 2018, total 11 pages; English machine translation.
"Dementia prevention in 3D, Kansai Medical University, etc.", Article Publication of Asahi Shimbun, Apr. 13, 2018, pp. 29, total 3 pages; English machine translation.
"MR improves brain cognitive function. System development by Kansai Medical University and Techlico Inc.", Article Publication of Nikkan Industrial newspaper, Apr. 13, 2018, pp. 29, total 3 pages; English machine translation.
"Prevention of dementia with 3D images. Developed by Kansai Medical College, etc.", Asahi Shimbun Digital, (web media), https://www.asahi.com/articles/ASL4F7TDLL4FUBQU01M.html, Apr. 14, 2018, total 11 pages; English machine translation.
"Improve cognitive function with 3D video / MR technology Development of new rehabilitation method", Asahi Shimbun, (web media), https://www.youtube.com/watch?v=P1y75b7dD54, Apr. 14, 2018, total 3 pages; English machine translation.
"[Series] Yuji Kotari VR column from a wheelchair Enjoyable rehabilitation with MR "Rehamaru" edition", Panora, (web media), https://panora.tokyo/58525/, Apr. 18, 2018, total 16 pages ; English machine translation.
"[Series] Yuji Kotari VR column from a wheelchair Enjoyable rehabilitation with MR "Rehamaru" edition", Niconico News, (web media), https://news.nicovideo.jp/watch/nw3443193, Apr. 18, 2018, total 13 pages; English machine translation.
"[Series] Yuji Kotari VR column from a wheelchair Fun rehabilitation with MR "Rihamaru" edition", Hacka Doll, (web media), Apr. 18, 2018, total 12 pages; English machine translation.
""Rehamaru" that combines MR (Mixed Reality) and cognitive function improvement rehabilitation", (web media), https://info.ninchisho.net/archives/28871, Apr. 21, 2018, total 8 pages; English machine translation.
""Rihamaru" is a fusion of MR (Mixed Reality) and cognitive function improvement rehabilitation.", Rakuten Infoseek News, (web media), Apr. 21, 2018, total 6 pages; English machine translation.
"Cognitive function improvement rehabilitation with MR", Electoronic Device Industry News, (web media), https://www.sangyo-times.jp/article.aspx?ID=2645, Jun. 1, 2018, total 5 pages; English machine translation.
"Cognitive function improvement rehabilitation with "mixed reality"", Yahoo! Japan Finance News, (web media), Jun. 4, 2018, total 6 pages; English machine translation.
"Cognitive function improvement rehabilitation with "mixed reality"", Excite News, (web media), https://www.excite.co.jp/news/article/Toushin_6264/?p=3, Jun. 4, 2018, total 18 pages; English machine translation.
""Rehamaru" that you can rehabilitate while having fun with VR / MR", ASCII Startup, (web media), http://ascii.jp/elem/000/001/707/1707527/, Jul. 23, 2018, total 11 pages; English machine translation.
""Rehamaru" that you can rehabilitate while having fun with VR / MR", Weekly ASCII, (web media), https://weekly.ascii.jp/elem/000/000/417/417146/, Jul. 23, 2018, total 16 pages; English machine translation.
""Rihamaru" that you can rehabilitate while having fun with VR / MR.", Startup Times, (web media), Jul. 23, 2018, total 6 pages; English machine translation.
"Rihamaru/ "Entertainment in medical care" Full-scale rehabilitation medical software using MR/VR.", Earthkey lab, (web media), Aug. 2, 2018, total 7 pages; English machine translation.
"Connecting Shenzhen and entrepreneurs", Article Publication of Japan Economic Times [Nikkei], Aug. 18, 2018, total 4 pages; English machine translation.
"Connecting Shenzhen and entrepreneurs Osaka City and Osaka Chamber of Commerce Evolution from ordering, collaboration in medical care and long-term care", Japan Economic Times [Nikkei], (web media), https://www.nikkei.com/article/DGKKZO34261960X10C18A8LKD000/, Aug. 18, 2018, total 6 pages; English machine translation.
"Make rehabilitation fun with mixed reality. Can also be applied to prevent dementia.", Aug. 31, 2018, pp. 39, total 6 pages; English machine translation.
"Make rehabilitation fun with mixed reality.", Japan Economic Times [Nikkei], (web media), https://www.nikkei.com/article/DGXMZO34795620Q8A830C1LKA000/, Aug. 31, 2018, total 8pages; English machine translation.
"The spatial search task of Mixed Reality increases gaze range on the case with unilateral spatial neglect", 52nd Occupational Therapy Society of Japan Oral Presentation, Sep. 8, 2018, total 4 pages; English machine translation.
The 23rd Shenzhen International Medical Devices Exhibition 2018 of Sep. 27, 2018; English machine translation.
"3D rehabilitation future form", Mainichi Newspaper, Oct. 13, 2018, No. 48917, p. 4; English machine translation.
"3D rehabilitation future form", Mainichi Newspaper, web media, https://mainichi.jp/articles/20181013/ddf/001/040/003000c, Oct. 13, 2018; English machine translation.
The 2nd Annual Autumn Meeting of the Japanese Association of Rehabilitation Medicine, "Rehabilitation Medicine is Adding Live to Years and Years to Life", Nov. 2, 2018; English machine translation.
The 2nd Annual Meeting of the Japanese Association of Rehabilitation Medicine of Nov. 2, 2018; English machine translation.
Hase et al., "The future of stroke rehabilitation for functional reconstruction", The 48th Annual Autumn Meeting of the Japanese Society of Clinical Neurophysiology, Nov. 8, 2018, vol. 46, No. 5, p. 323; English machine translation.
Hirakata Citizen's University 2018, Kansai Medical University, Nov. 18, 2018; English machine translation.
42nd Annual Meeting of the Japanese Society of Higher Brain Dysfunction of Dec. 6, 2018; English machine translation.
Hashimoto et al., "Validity of the Mixed Reality selective elimination task for unilateral spatial neglect", 42nd Annual Meeting of the Japanese Society of Higher Brain Dysfunction, Dec. 7, 2018, 2B4-2, p. 237; English machine translation.
Chinese Office Action (Chinese OA) issued on May 23, 2022 for Patent Application No. 201980089743.1 and its English translation.

\* cited by examiner

FIG. 11
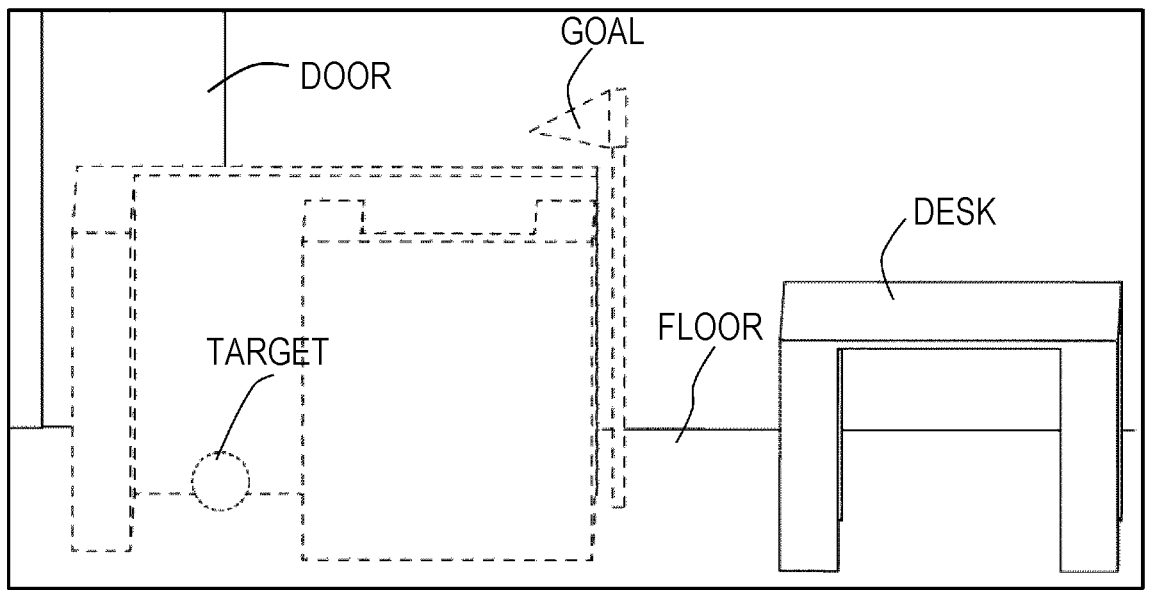
(a)
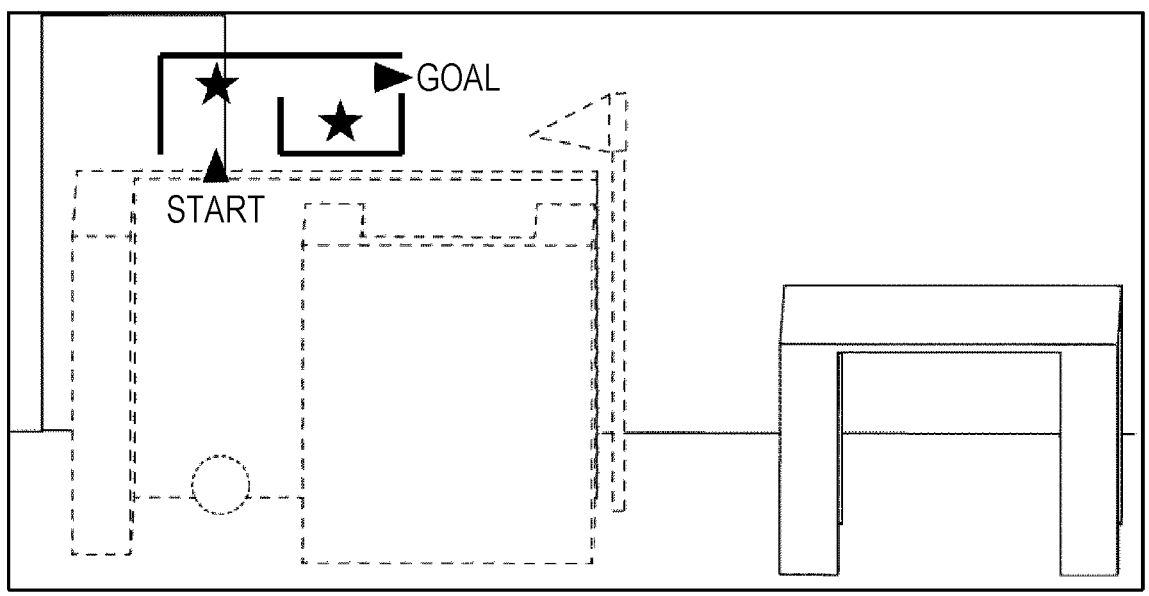
(b)

FIG. 12
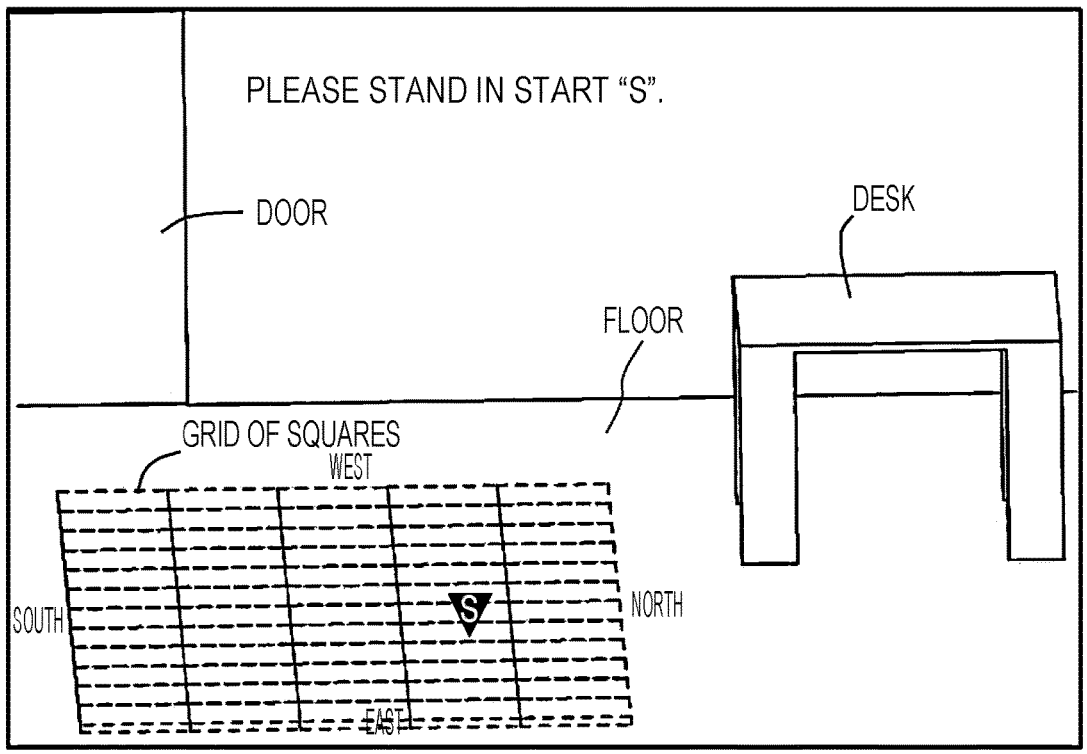
(a)
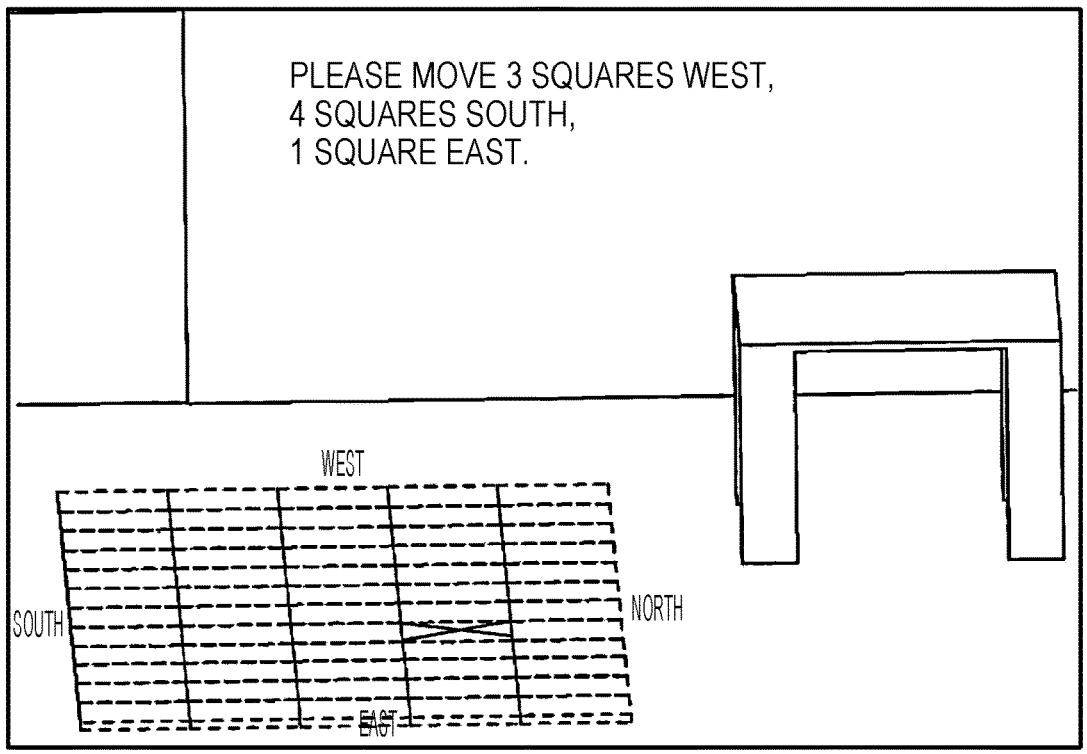
(b)

FIG. 13

| REHAB RECORD INFORMATION | | | | | | | | | |
|---|---|---|---|---|---|---|---|---|---|
| DOCTOR | PATIENT | TYPE OF APP | MODE | YEAR, MONTH, AND DAY OF TREATMENT | PRACTITIONER | SCORE | ACHIEVEMENT RECORD | EYE POINT POSITION MOVEMENT RECORD | MOVING IMAGE |
| A | a | 1 | 1 | 12182018 | x | 45 | ... | ... | a1.mp4 |
| | | 2 | 1 | 12182018 | x | 52 | ... | ... | a2.mp4 |
| | | 3 | 1 | 12182018 | x | 30 | ... | ... | a3.mp4 |
| | | 4 | 1 | 12182018 | x | 67 | ... | ... | a4.mp4 |
| | | 5 | 2 | 12182018 | x | 20 | ... | ... | a5.mp4 |
| | b | 1 | 1 | 12192018 | y | 72 | ... | ... | b1.mp4 |
| | | 2 | 1 | 12192018 | y | 47 | ... | ... | b2.mp4 |
| | | 3 | 1 | 12192018 | y | 32 | ... | ... | b3.mp4 |
| | | 4 | 1 | 12192018 | y | 51 | ... | ... | b4.mp4 |

| REHAB SCHEDULE | | | | | | | |
|---|---|---|---|---|---|---|---|
| PATIENT NAME: ICHIRO TANAKA | | | | | | | |
| DECEMBER 2018 | | | | | | | |
| SAT 15 | SUN 16 | MON 17 | TUE 18 | WED 19 | THU 20 | FRI 21 | |
| | TANAKA 1 | TANAKA 1 | TANAKA 1 | TANAKA 2 | | | |
| | NUMBER CANCELLATION | NUMBER CANCELLATION | NUMBER CANCELLATION | NUMBER CANCELLATION | | | |
| | FIRST SELECTION CANCELLATION | FIRST SELECTION CANCELLATION | FIRST SELECTION CANCELLATION | FIRST SELECTION CANCELLATION | | | |
| | SECOND SELECTION CANCELLATION | SECOND SELECTION CANCELLATION | SECOND SELECTION CANCELLATION | SECOND SELECTION CANCELLATION | | | |
| | SPATIAL ARRANGEMENT | SPATIAL ARRANGEMENT | SPATIAL ARRANGEMENT | SPATIAL ARRANGEMENT | | | |
| | MAZE | MAZE | MAZE | | | | |
| | MOVE INSTRUCTION | MOVE INSTRUCTION | MOVE INSTRUCTION | | | | |

(b)

| REHAB SCHEDULE | | | | | | | |
|---|---|---|---|---|---|---|---|
| PATIENT NAME: ICHIRO TANAKA | | | | | | | |
| DECEMBER 2018 | | | | | | | |
| SAT 15 | SUN 16 | MON 17 | TUE 18 | WED 19 | THU 20 | FRI 21 | |
| | TANAKA 1 | TANAKA 1 | TANAKA 1 | TANAKA 2 | TANAKA 3 | | |
| | NUMBER CANCELLATION | NUMBER CANCELLATION | NUMBER CANCELLATION | NUMBER CANCELLATION | NUMBER CANCELLATION | | |
| | FIRST SELECTION CANCELLATION | FIRST SELECTION CANCELLATION | FIRST SELECTION CANCELLATION | FIRST SELECTION CANCELLATION | FIRST SELECTION CANCELLATION | | |
| | SECOND SELECTION CANCELLATION | SECOND SELECTION CANCELLATION | SECOND SELECTION CANCELLATION | SECOND SELECTION CANCELLATION | SECOND SELECTION CANCELLATION | | |
| | SPATIAL ARRANGEMENT | SPATIAL ARRANGEMENT | SPATIAL ARRANGEMENT | SPATIAL ARRANGEMENT | | | |
| | MAZE | MAZE | MAZE | | | | |
| | MOVE INSTRUCTION | MOVE INSTRUCTION | MOVE INSTRUCTION | | | | |

FIG. 15

(a)
REHAB SCHEDULE
DATE OF TREATMENT
MENU — CREATE NEW MENU / SELECT EXISTING MENU (b)
EDIT MENU
MENU NAME: TANAKA 3
SELECT APP [+] ← ADD APP

SAVE   CANCEL (c)
ADD APP
TEST | TRAINING
SPATIAL PERCEPTION | EXECUTIVE FUNCTIONING | MEMORY | INFORMATION ACQUISITION ABILITY
ATTENTION | INHIBITION

FIRST SELECTION CANCELLATION | SPATIAL ARRANGEMENT | MAZE

ADD   CANCEL (d)
EDIT MENU
MENU NAME: TANAKA 3
SELECT APP [+]

NUMBER CANCELLATION
FIRST SELECTION CANCELLATION
SECOND SELECTION CANCELLATION

SAVE   CANCEL

FIG. 16
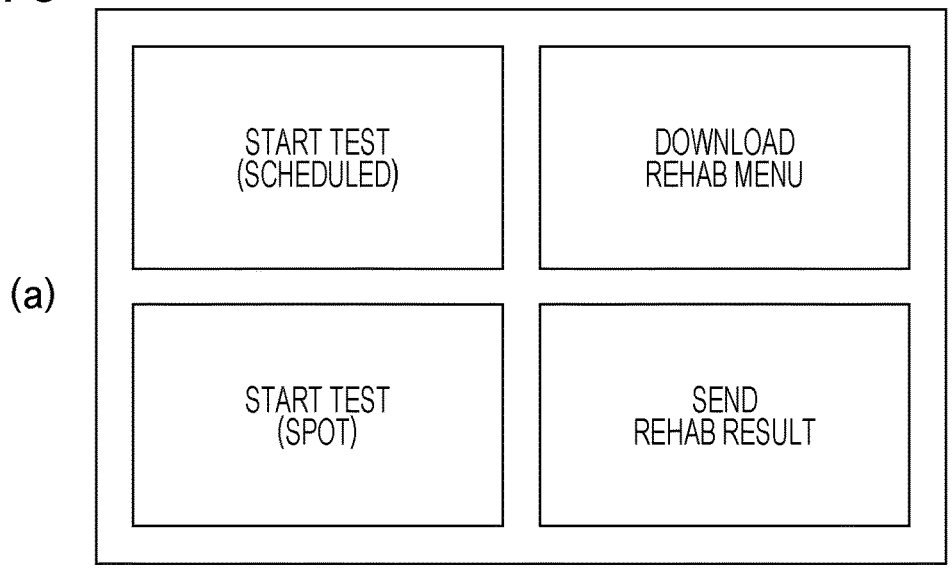
(a)
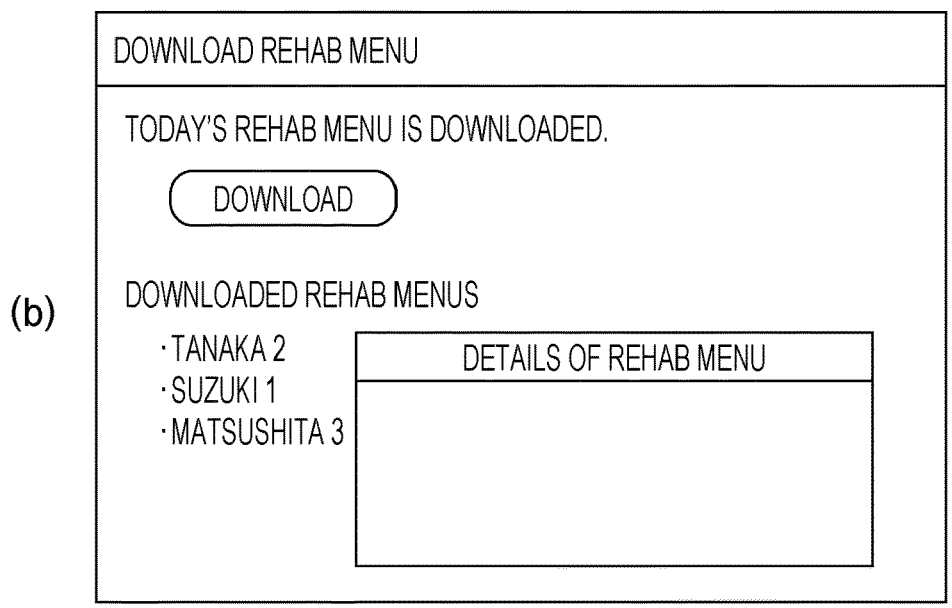
(b)
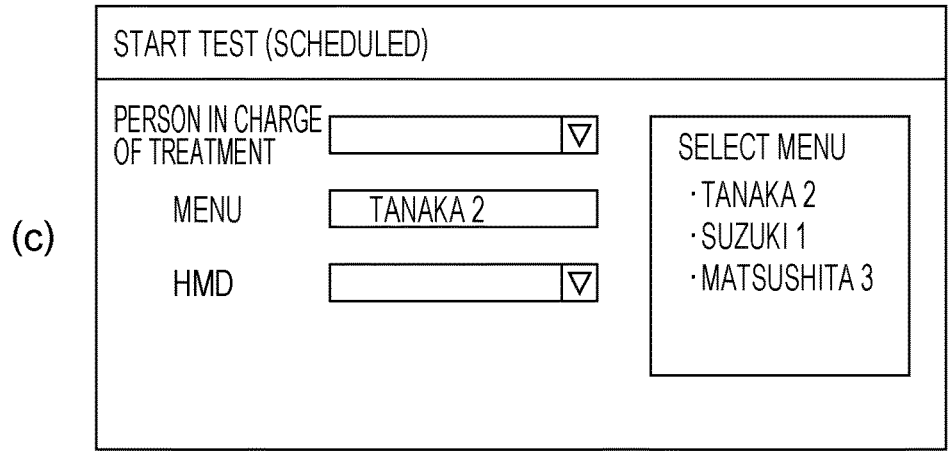
(c)

```
START TEST (SCHEDULED)

PERSON IN CHARGE    [GORO TOKKYO ▽]     SETTING INFORMATION
OF TREATMENT
         MENU       [TANAKA 2      ]    (PREVIOUS APP) (NEXT APP)
         HMD        [TERMINAL A  ▽]         DETAILS OF APP

NUMBER CANCELLATION
                                        BALL COLOR
                                        NUMBER OF BALLS
                                        TEXT SIZE
                                        HINT DISPLAY GRACE
                                        SETTING RANGE
                                        MODE
                                        CANCELLATION METHOD
                                        TIME LIMIT (EDIT) (EXECUTE)
```

(b)

```
REHAB IN PROGRESS

PATIENT'S VIEW                    EXECUTION SETTINGS

LINE OF SIGHT          NUMBER CANCELLATION
       ①         ↙  ④                BALL COLOR
                 ●                   NUMBER OF BALLS
                 ②                   TEXT SIZE
                                     HINT DISPLAY GRACE
       ⑦                             SETTING RANGE
                                     MODE
                                     CANCELLATION METHOD
                                     TIME LIMIT

NO. 1 NEXT                       (STOP) (ADVISE)
```

FIG. 18
(a) 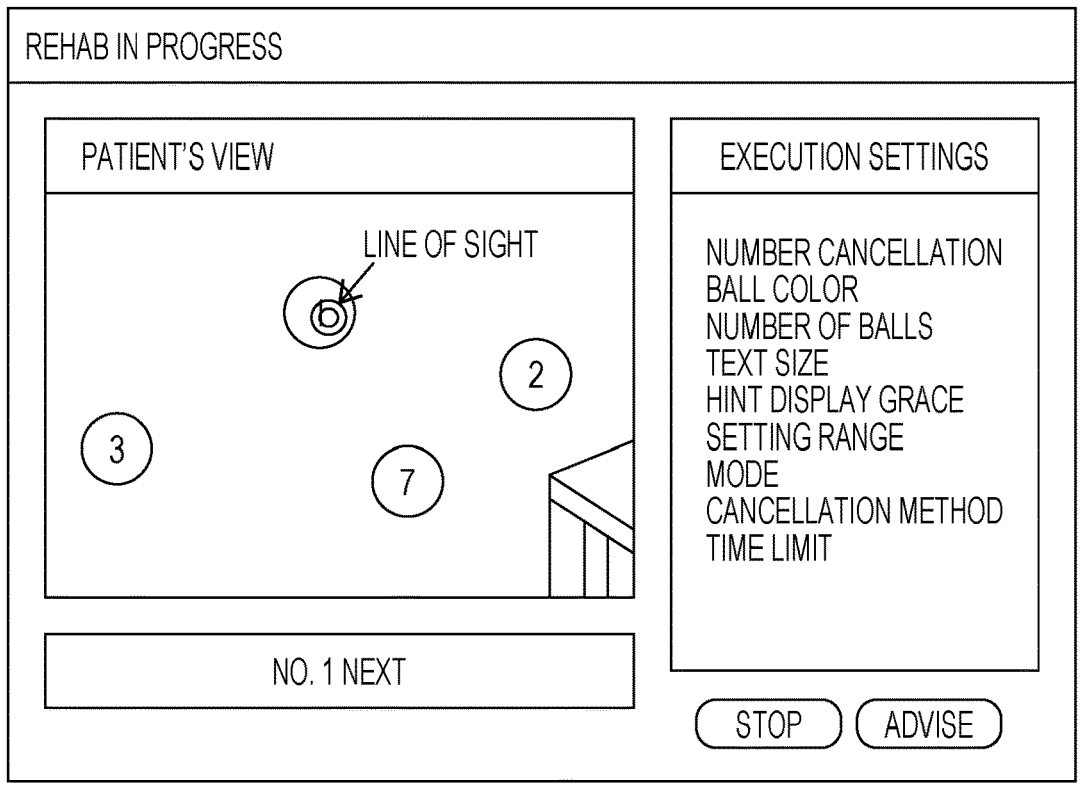
(b) 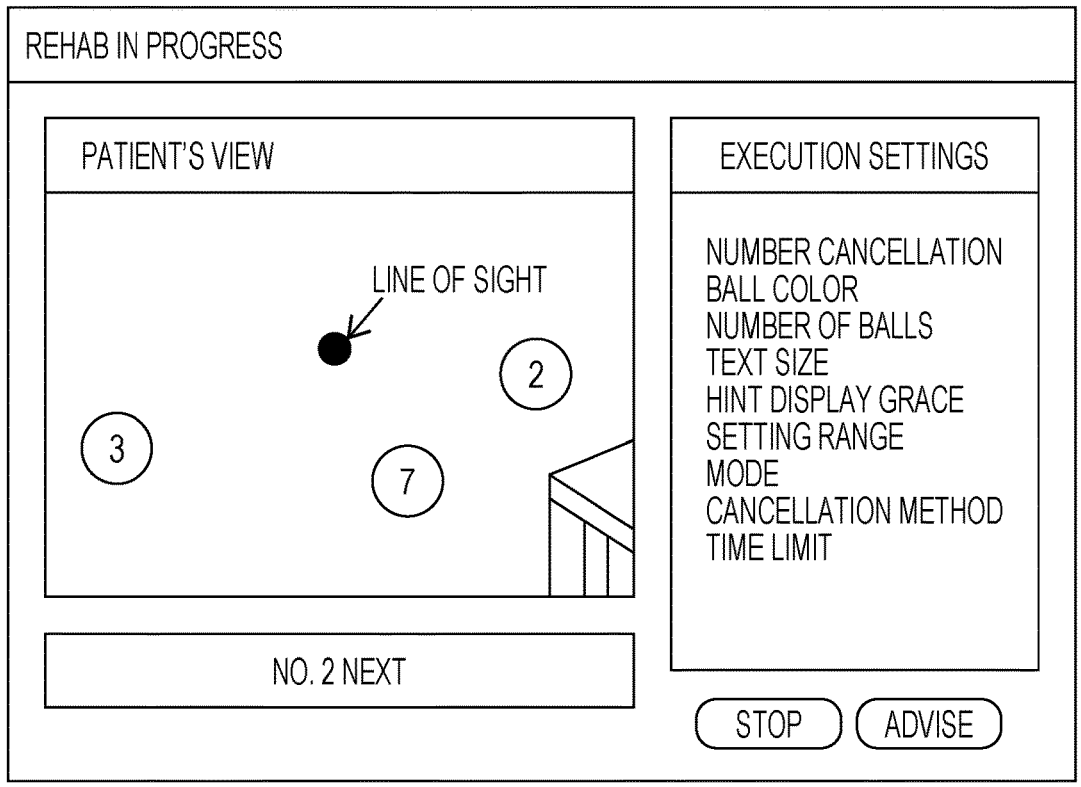

FIG. 19

| EXECUTION RESULT | | | | | |
|---|---|---|---|---|---|
| SCORE: 47 POINTS | | | | | CHECK SETTINGS |
| TAP RECORD | | | | | NUMBER CANCELLATION |
| No | TAPPED TIME | REQUIRED TIME | OBJECT | CORRECT/ INCORRECT | BALL COLOR |
| 1 | ... | ... | 1 | ○ | NUMBER OF BALLS |
| 2 | ... | ... | 3 | × | TEXT SIZE |
| 3 | ... | ... | 2 | ○ | HINT DISPLAY GRACE |
| 4 | ... | ... | 3 | ○ | SETTING RANGE |
| 5 | ... | ... | 8 | × | MODE |
| 6 | ... | ... | 6 | × | CANCELLATION METHOD |
| 7 | ... | ... | 5 | ○ | TIME LIMIT |

CLOSE

FIG. 20
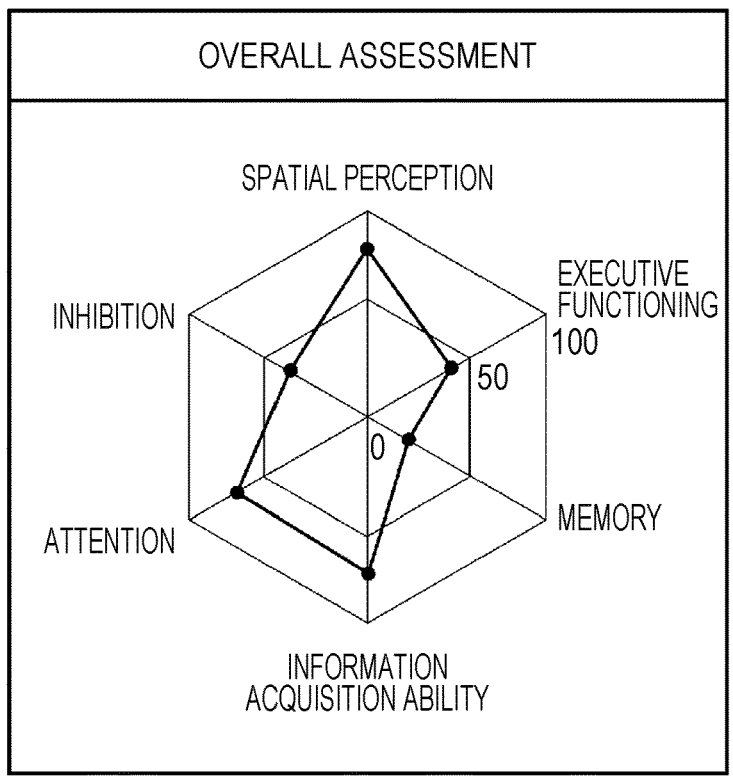
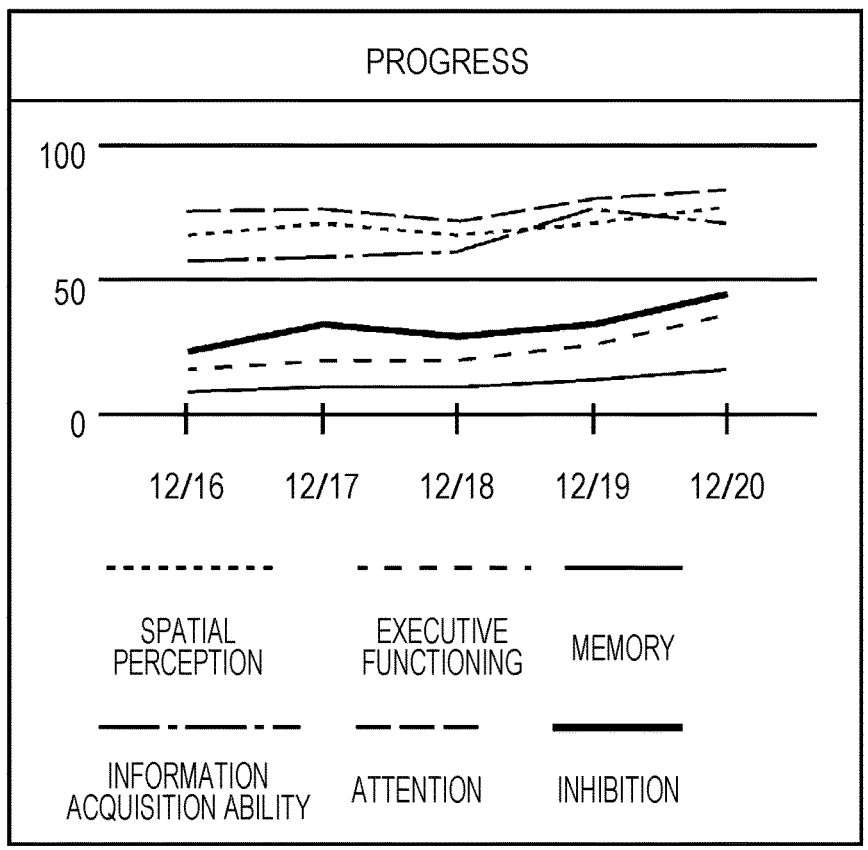

| NUMBER CANCELLATION APP SETTING ITEM | | |
|---|---|---|
| TARGET COLOR | RED | ▽ |
| NUMBER OF TARGETS | 10 | ▽ |
| TEXT SIZE | MEDIUM | ▽ |
| HINT DISPLAY GRACE TIME | 5 | ▽ |
| SETTING RANGE | 80° | ▽ |
| MODE | MEASUREMENT MODE | ▽ |
| CANCELLATION METHOD | GESTURE | ▽ |
| TIME LIMIT | 0 SECONDS | ▽ |

FIG. 38

| FIRST SELECTION CANCELLATION APP SETTING ITEM | | | | | | | |
|---|---|---|---|---|---|---|---|
| CORRECT TARGET | MEDIUM | ▽ | DOUGHNUT | ▽ | 10 PIECES | ▽ | |
| | ⊕ ⊖ | | | | | ▽ | |
| INCORRECT TARGET | SMALL | ▽ | PENCIL | ▽ | 10 PIECES | ▽ | |
| | ⊕ ⊖ | | | | | ▽ | |
| SETTING RANGE | 90° | | | | | ▽ | |
| MODE | MEASUREMENT MODE | | | | | ▽ | |
| CANCELLATION METHOD | GESTURE | | | | | ▽ | |
| TIME LIMIT | 300 SECONDS | | | | | ▽ | |

FIG. 39

| SECOND SELECTION CANCELLATION APP SETTING ITEM | | | | | | | |
|---|---|---|---|---|---|---|---|
| CORRECT TARGET | MEDIUM | ▽ | RED BALL | ▽ | 10 PIECES | ▽ | |
| | ⊕ ⊖ | | | | | ▽ | |
| SETTING RANGE | 120° | | | | | ▽ | |
| MODE | MEASUREMENT MODE | | | | | ▽ | |
| CANCELLATION METHOD | GESTURE | | | | | ▽ | |
| TIME LIMIT | 300 SECONDS | | | | | ▽ | |

FIG. 40

| SPATIAL ARRANGEMENT APP SETTING ITEM | | | | | | |
|---|---|---|---|---|---|---|
| WALL TYPE | BRICK | | | | | ▽ |
| ROAD LENGTH | 300cm | | | | | ▽ |
| ROAD WIDTH | 150cm | | | | | ▽ |
| WALL HEIGHT (MINIMUM) | 100cm | | | | | ▽ |
| WALL HEIGHT (MAXIMUM) | 120cm | | | | | ▽ |
| CORRECT TARGET | LARGE | ▽ | RED FLOWER | ▽ | 10 PIECES | ▽ |
| | ⊕ ⊖ | | | | | ▽ |
| INCORRECT TARGET | MEDIUM | ▽ | YELLOW FLOWER | ▽ | 5 PIECES | ▽ |
| | ⊕ ⊖ | | | | | ▽ |
| MODE | TRAINING MODE | | | | | ▽ |
| CANCELLATION METHOD | LINE OF SIGHT (GAZE) | | | | | ▽ |
| TIME LIMIT | 0 SECONDS | | | | | ▽ |

FIG. 41

| MAZE APP SETTING ITEM | | | | | | |
|---|---|---|---|---|---|---|
| MODE | MEASUREMENT MODE | | | | | ▽ |
| NUMBER OF SQUARES OF MAZE IN BREADTH | 3 SQUARES | | | | | ▽ |
| NUMBER OF SQUARES OF MAZE IN DEPTH | 6 SQUARES | | | | | ▽ |
| PASSAGE WIDTH | 100cm | | | | | ▽ |
| WALL HEIGHT | 50cm | | | | | ▽ |
| CORRECT TARGET | MEDIUM | ▽ | DOUGHNUT | ▽ | 5 PIECES | ▽ |
| | ⊕ ⊖ | | | | | ▽ |
| TIME LIMIT | 0 SECONDS | | | | | |

FIG. 42

| SQUARE MOVE APP SETTING ITEM | | |
|---|---|---|
| NUMBER OF SQUARES IN BREADTH | 5 SQUARES | ▽ |
| NUMBER OF SQUARES IN DEPTH | 5 SQUARES | ▽ |
| NUMBER OF MOVES | 3 | ▽ |
| NUMBER OF TIMES OF REPETITION | one | ▽ |
| STOP ALLOWED TIME | 10 SECONDS | ▽ |
| MODE | MEASUREMENT MODE | ▽ |
| TIME LIMIT | 0 SECONDS | ▽ |

FIG. 43

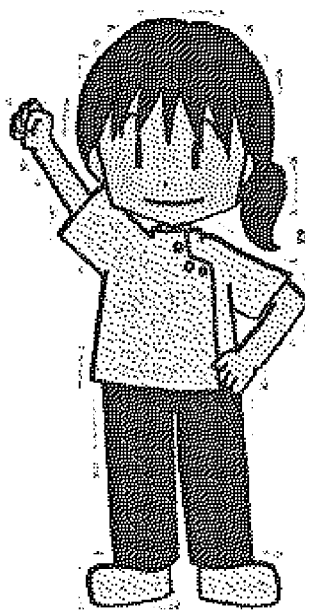

HELLO, XX!
DO YOUR BEST WITH REHAB TODAY!

PLEASE LOOK A LITTLE TO THE LEFT.

THIS IS AMAZING! YOUR SCORE IS HIGHER THAN LAST TIME!
LET'S CHALLENGE A LITTLE MORE DIFFICULT PROBLEM NEXT TIME!

REHABILITATION SYSTEM AND IMAGE PROCESSING APPARATUS FOR HIGHER BRAIN DYSFUNCTION

TECHNICAL FIELD

The present invention relates to a system for rehabilitating a patient of higher brain dysfunction caused by, for example, stroke, dementia, cerebral palsy, traumatic brain injury, brain tumors, development disability, depression, schizophrenia, or Parkinson's disease, or more particularly relates to a system and image processing apparatus for rehabilitation of higher brain dysfunction by use of an image processing technology.

BACKGROUND ART

Higher brain dysfunction is a disease that is due to damage to the brain caused by, for example, stroke, dementia, cerebral palsy, traumatic brain injury, brain tumors, development disability, depression, schizophrenia, or Parkinson's disease, and has symptoms such as memory impairment, an attention disorder, and executive dysfunction.

Apparatuses for rehabilitation of higher brain dysfunction by use of virtual images have conventionally been proposed as described in Patent Literatures 1 to 7.

In a rehabilitation apparatus for a person with brain dysfunction, which is described in Patent Literature 1, a virtual reality image is displayed on a head mounted visual display device (4). A patient operates a training machine (6) and a space joystick (5). Accordingly, an image that looks as if the patient is moving in a virtual space is displayed on the head mounted visual display device (4). Consequently, the patient operates, for example, the training machine (6), viewing the image of the virtual environment, and the operation is reflected on the image of the virtual environment. Accordingly, it is considered that it is possible to restore the function of moving the body in response to visual stimuli to the brain. In Patent Literature 1, various images can be prepared as the virtual environment image. Accordingly, it is considered that a further change in visual information, which includes a large amount of information, can evoke the patient's motivation and interest in training.

In a higher brain dysfunction rehabilitation apparatus described in Patent Literature 2, a virtual world is displayed on a virtual world control means (104), and also task data is presented to a patient. Success or failure is determined on the basis of the patient's response to the task data. Data on the cognitive state of the patient is created on the basis of the result of the determination of success or failure. Moreover, in the higher brain dysfunction rehabilitation apparatus described in Patent Literature 2, the degree of difficulty of the task data is changed on the basis of the result of the assessment of the patient achievement. Consequently, the higher brain dysfunction rehabilitation apparatus described in Patent Literature 2 provides an environment where the patient can perform various movements required in daily life.

A rehabilitation support system described in Patent Literature 3 causes a head mounted display that is mounted on the head of a patient to display a guide image being a guide for movements of rehabilitation, and displays a guide presenting a movement that the patient should perform within the field of view of the patient. Consequently, the patient can understand a movement that he/she should perform intuitively and naturally. It becomes possible to smoothly proceed with rehabilitation.

In a rehabilitation support apparatus described in Patent Literature 4, it is configured in such a manner as to display an image on a head mounted display (94). It is configured in such a manner, for example, that a user views an underwater image when seated in a chair, and views a sky image above the sea when standing up, in an attempt to increase the motivation for the sit to stand exercise for rehabilitation.

Rehabilitation support systems described in Patent Literatures 5 to 7 display, on a head mounted display (233), an avatar image that moves in response to rehabilitation movement and a target image representing a target for a rehabilitation movement, compares the rehabilitation movement with a target position, and assesses the rehabilitation ability. Moreover, Patent Literatures 5 to 7 touch on the utility of a dual task that aims to improve the effect of rehabilitation by combining two tasks including a cognitive function and a motor task. A first rehabilitation movement and a second rehabilitation movement are detected to assess the rehabilitation ability on the basis of both movements.

In a rehabilitation system described in Patent Literature 8, a system is proposed which displays a rehab task on a tablet terminal and performs rehab for the purpose of rehabilitation for a patient with higher brain dysfunction. In the system described in Patent Literature 8, a server acquires the rehab task level of the patient from a hard disk, and determines a rehab task content set in accordance with the acquired level. The tablet terminal displays a rehab task corresponding to the content determined by the server, and the patient solves the rehab task. The tablet terminal determines the rehabilitation task level of the patient on the basis of the results of a predetermined number of most recently answered rehab tasks.

Patent Literature 9 relates to a system that is entertaining to maintain the motivation of a patient with higher brain dysfunction for rehabilitation. The rehabilitation support system described in Patent Literature 9 is provided with a camera that captures the patient's image, and an image display means such as a projector or liquid crystal display that displays the patient's image captured by the camera. In the system described in Patent Literature 9, a displayed target of a rehabilitation-purpose game and an image of the patient's hand captured by the camera are composited with an image displayed by the image display means, and the position of the hand is detected. Accordingly, the game is progressed depending on whether or not the patient could select the displayed target to perform rehabilitation.

In a rehabilitation-purpose system described in Patent Literature 10, a captured patient's image acquired by a camera (11) and a rehab image generated in a computer (12) are composited together. A projector (14) is used to display the composite image on a screen (13). In the rehabilitation-purpose system, the position of a moving part (hand) of the patient in the patient's captured image is identified from image data. For example, a display mode of a response image portion included in the rehab image is changed on the basis of the interference state of the patient's moving part and the response image portion in the rehab image to encourage the patient in rehab movement.

Patent Literatures 11 and 12 display a virtual image on a display and rehabilitate a patient.

The systems described in Patent Literatures 1 to 7 are for encouraging a patient to perform movements for rehabilitation by using, for example, a head mounted display, reproducing a virtual space, and letting the patient move in the virtual space, and clearing up a task presented in the virtual space.

As in the systems described in Patent Literatures 9 to 12, there is also a system that displays, for example, a composite image on a projector or display, and encourages rehabilitation movements.

In the system described in Patent Literature 8, a task is displayed on the tablet terminal for rehabilitation. Patent Literature 8 discloses the system that transmits the task content set in accordance with the level of the patient from the server to the tablet terminal.

CITATION LIST

Patent Literature

Patent Literature 1: JP-A-08-280762
Patent Literature 2: JP-A-2001-079050
Patent Literature 3: JP-A-2015-228957
Patent Literature 4: JP-A-2018-079308
Patent Literature 5: Japanese Patent No. 6200615
Patent Literature 6: JP-A-2018-185501
Patent Literature 7: Japanese Patent No. 6425287
Patent Literature 8: JP-A-2018-195273
Patent Literature 9: JP-A-2006-325740
Patent Literature 10: JP-A-2011-110215
Patent Literature 11: JP-A-09-120464
Patent Literature 12: JP-A-10-151162

SUMMARY OF THE INVENTION

Problems to be Solved by the Invention

In the field of rehabilitation for patients with higher brain dysfunction, a doctor determines the contents of rehabilitation for a patient, and a practitioner such as an occupational therapist rehabilitates the patient on the basis of the doctor's instruction. In order to make rehabilitation efficient and effective, it is required to share the symptoms and improvement state of the patient between the doctor and the practitioner and to perform rehabilitation appropriate for the state of the patient.

In the systems described in Patent Literatures 1 to 7, attention is focused only on rehabilitation using a virtual image. The utility of rehabilitation of higher brain dysfunction using a virtual image is not undeniable. In Patent Literatures 1 to 7, however, respects of how a doctor and a practitioner share information and how a doctor determines optimal rehabilitation are not at all taken into account. The same applies to the systems of Patent Literatures 9 to 12 that display an image on a projector or display.

The system described in Patent Literature 8 also simply transmits a task content set in accordance with the level of a patient from the server to the tablet terminal. The system described in Patent Literature 8 is not a system for allowing a doctor to accurately grasp, for example, the improvement state of a patient and to determine an optimal rehabilitation menu.

Higher brain dysfunction is a disorder caused by, for example, damage to the brain. In order to treat higher brain dysfunction, it is effective that a doctor and a practitioner grasp an improvement state appropriately to gradually improve the brain dysfunction by use of an appropriate rehabilitation menu. However, the known systems described in Patent Literatures 1 to 12 cannot share, for example, the results of rehabilitation performed for a patient and the improvement state after treatment between a doctor and a practitioner.

Therefore, an object of the present invention is to provide a rehabilitation system for higher brain dysfunction to facilitate a doctor and a practitioner grasping the state of rehabilitation for a patient and to enable the construction of an appropriate rehabilitation menu.

Moreover, the systems described in Patent Literatures 1 to 7 display an image on, for example, a head mounted display to realize virtual reality (VR: Virtual Reality) and use virtual reality for rehabilitation, but have risks that a patient falls into a state, what is called VR sickness, falls down and collides with real-world obstacles. If, for example, a patient feels ill, an abnormality occurs in the sense, or the patient injures himself/herself due to VR-based rehabilitation, the effect of rehabilitation cannot be expected.

Therefore, another object of the present invention is to provide a system that allows a patient to undergo rehabilitation without feeling strange.

Solutions to the Problems

In order to solve the above problems, the present invention has the following features: The present invention is a rehabilitation system for performing rehabilitation of higher brain dysfunction, and includes: an image processing apparatus configured to execute an app for presenting a patient a problem for rehab based on an image using virtual reality, augmented reality, or mixed reality and store the patient's problem solution record as rehab record information; a practitioner-side terminal configured to receive the rehab record information from the image processing apparatus; a server configured to save the rehab record information transmitted from the practitioner-side terminal; and a doctor-side terminal configured to receive the rehab record information from the server and display the state of rehabilitation performed for the patient on the basis of the rehab record information.

The image processing apparatus includes one or more types of apps for presenting the problem. The practitioner-side terminal can select an app to be implemented on the image processing apparatus, and instruct the image processing apparatus to execute the selected app.

The doctor-side terminal creates a schedule of rehab to be performed on the image processing apparatus in such a manner as to link the schedule to the app to be used, and saves the schedule in the server. The practitioner-side terminal can download the schedule saved in the server, and instruct the image processing apparatus to execute the app specified by the schedule.

The app to be used on the image processing apparatus is associated with at least one impairment that is expected to be improved by the implementation of the app. The rehab record information includes the score of an answer to the problem set by the app. The doctor-side terminal displays the score of the app for each impairment to provide the display in such a manner as to allow comprehending an impairment improvement state.

The doctor-side terminal displays app score results on a time-series basis.

The rehab record information includes information related to the movement of the patient. The doctor-side terminal and/or the practitioner-side terminal can provide a display that reproduces the movement of the patient on the basis of the rehab record information.

The image processing apparatus transmits, to the practitioner-side terminal, an image that is visible to the patient during the execution of the app. The practitioner-side terminal displays the image transmitted from the image processing apparatus.

The image displayed on the practitioner-side terminal is saved as a moving image.

The doctor-side terminal can play the saved moving image.

The image transmitted from the image processing apparatus is distributed simultaneously to the doctor-side terminal.

The app to be executed on the image processing apparatus includes an adjustable setting condition. The doctor-side terminal and/or the practitioner-side terminal can adjust the setting condition.

The range of an angle to display the problem is adjustable as the setting condition.

The number of objects to be displayed in the problem is adjustable as the setting condition.

The image processing apparatus includes a measurement mode and a training mode as a mode to execute the app. In the measurement mode, the image processing apparatus sets a predetermined problem. In the training mode, the image processing apparatus sets a randomly created problem.

The image processing apparatus displays an image of an avatar being a virtual trainer.

The doctor-side terminal, the practitioner-side terminal, the image processing apparatus, or the server adjusts the degree of difficulty of the problem on the basis of a past score of the problem, and causes the image processing apparatus to set a problem according to the degree of difficulty.

The doctor-side terminal, the practitioner-side terminal, the image processing apparatus, or the server creates a problem in accordance with a weak point of the patient based on the rehab record information, according to the weak point, and causes the image processing apparatus to set the problem.

The image processing apparatus executes a number cancellation app that displays images of numbers, using the virtual reality, the augment reality, or the mixed reality, and sets a problem that prompts cancelling the images of the numbers sequentially.

The image processing apparatus executes a first selection cancellation app that displays images of a target and a non-target, using the virtual reality, the augmented reality, or the mixed reality, and sets a problem that prompts cancelling the image of the target.

The image processing apparatus executes a second selection cancellation app that displays images of a target and a non-target, using the virtual reality, the augmented reality, or the mixed reality, and sets a problem that prompts selecting the image of the target and changing the image after the selection.

The image processing apparatus executes a spatial arrangement app that displays at least one image of a wall, and images of a target and a non-target placed on the wall, using the virtual reality, the augmented reality, or the mixed reality, and sets a problem that prompts cancelling the image of the target.

The image processing apparatus executes a maze app that displays an image of a maze, using the virtual reality, the augmented reality, or the mixed reality, and sets a problem that prompts clearing the maze.

In the maze app, a target image is displayed to set a problem that prompts cancelling the target image. Cancellation here indicates a concept including cancellation of a target upon reaching a predetermined position, in addition to the intended selection of the target.

The image processing apparatus executes a square move app that displays an image of a grid of squares, using the virtual reality, the augmented reality, or the mixed reality, and sets a problem that prompts moving over the grid of squares.

The image processing apparatus displays a virtual image also outside the field of view of the patient in an app that displays the virtual image using the virtual reality, the augmented reality, or the mixed reality.

The virtual image is the image of the target and/or the non-target of the problem.

The virtual image is the image of the wall, maze, or grid of squares used in the problem.

Moreover, the present invention is an image processing apparatus including: a spatial recognition unit configured to recognize a surrounding space of the image processing apparatus; a tracking unit configured to recognize the position and inclination of the image processing apparatus in the space recognized by the spatial recognition unit; an orientation detection unit configured to detect the orientation of a user; an image processing unit configured to place a virtual object in the space recognized by the spatial recognition unit and generate an image of the virtual object visible to the user on the basis of the position and inclination recognized by the tracking unit and the orientation detected by the orientation detection unit; and a mixed reality-specific display unit configured to display the image of the virtual object generated by the image for the user as if the image generated by the image exists in a real space, in which the image processing apparatus further includes a control unit configured to generate a problem as if the image of the virtual object used for rehabilitation of higher brain dysfunction exists in the real space.

The control unit uses an image to be selected by the user as the image of the virtual object, and generates the problem in such a manner as to place the image at least in the field of view of the user.

The control unit generates the problem in such a manner as to place the image to be selected by the user also outside the field of view of the user.

The control unit scores the problem on the basis of the detection result of the position of the image processing apparatus by the tracking unit.

The control unit uses an image for prompting the user to move in the real space as the image of the virtual object, and generates the problem in such a manner as to place the image at least in the field of view of the user.

The control unit generates the problem in such a manner as to place the image for prompting the user to move in the real space also outside the field of view of the user.

The control unit includes a measurement mode and a training mode as a mode to execute an app for presenting a patient the problem. In the measurement mode, the control unit sets a predetermined problem. In the training mode, the control unit sets a randomly created problem.

The image processing apparatus displays an image of an avatar being a virtual trainer upon executing the app for presenting the patient the problem.

The image processing apparatus adjusts the degree of difficulty on the basis of a past score of the problem, and sets a problem according to the degree of difficulty.

The image processing apparatus sets a problem according to a weak point of the patient on the basis of the rehab record information.

Moreover, the present invention is a storage medium in which a computer program for rehabilitation of higher brain dysfunction is stored, the storage medium storing a computer program to be executed in an image processing apparatus including: a spatial recognition unit configured to recognize a surrounding space of the image processing apparatus; a tracking unit configured to recognize the position and inclination of the image processing apparatus in the space recognized by the spatial recognition unit; an orientation detection unit configured to detect the orientation of a user; an image processing unit configured to place a virtual object in the space recognized by the spatial recognition unit and generate an image of the virtual object visible to the user on the basis of the position and inclination recognized by the tracking unit and the orientation detected by the orientation detection unit; and a mixed reality-specific display unit configured to display the image of the virtual object generated by the image for the user as if the image generated by the image exists in a real space, in which the computer program causes the image processing apparatus to function as a control means configured to generate a problem as if the image of the virtual object used for rehabilitation of higher brain dysfunction exists in the real space.

Effects of the Invention

According to the present invention, it is possible to store rehab record information in the image processing apparatus that performs rehab with an image using virtual reality, augmented reality, or mixed reality and share the rehab record information between the practitioner-side terminal and the doctor-side terminal. Therefore, it is made easy for a doctor and a practitioner to grasp the state of rehabilitation for a patient. As a result, it becomes possible to construct an appropriate rehabilitation menu.

The image processing apparatus includes one or more types of apps. An app to be used is specified by the practitioner-side terminal. Consequently, it becomes possible to execute the app suitable for the symptom of the patient and increase the effect of rehabilitation.

The doctor-side terminal can specify an app to be used for treatment and easily create a schedule of rehab. The practitioner-side terminal can download the schedule created by the doctor-side terminal and instruct the image processing apparatus to execute the app. Hence, it becomes possible to easily perform appropriate rehab as instructed by the doctor.

Each app is associated with an impairment to be expected to be improved. Accordingly, it becomes possible to grasp the score as a result of the execution of an app on an impairment basis. Accordingly, the doctor-side terminal can grasp an impairment improvement state objectively and visually.

Moreover, the doctor-side terminal displays the scores on a time-series basis. Accordingly, it becomes possible to objectively and visually grasp whether or not rehab is producing an effect.

The movement of the patient included in the rehab record information is displayed on the doctor-side terminal and/or the practitioner-side terminal. Accordingly, for example, the doctor can grasp the state of the impairment of the patient objectively and visually.

The image viewed by the patient is displayed on the practitioner-side terminal during the execution of the app. Accordingly, for example, the practitioner can grasp, for example, whether or not the patient understands the meaning of rehab and undergoes rehab, and give, for example, an appropriate advice.

The above image is saved as a moving image. Accordingly, the state of rehab of the patient still can be checked later.

The saved moving image can be played later on the doctor-side terminal. Even a doctor who was not on-site during rehab can grasp the state of rehab and can use the state of rehab as a reference to construct a rehab menu for the future.

Moreover, the above image is distributed simultaneously to the doctor-side terminal. Accordingly, even if rehab is performed at a distant location, the doctor can gain an understanding of the state of rehab simultaneously, and it becomes possible to use the understanding to construct an appropriate rehab menu.

The app setting conditions are made adjustable. Accordingly, it becomes possible to make a problem easy or difficult with the progress of rehab. It is configured in such a manner that these adjustments can be made on the doctor-side terminal and/or the practitioner-side terminal. Accordingly, it becomes possible to create a rehab menu suitable for the state of the patient as circumstances demand.

For example, the range of the angle to display the problem is made adjustable. Accordingly, it becomes possible to adjust the rehab menu in accordance with a narrow or wide field of view of the patient as circumstances demand.

For example, the number of objects to be displayed in the problem is made adjustable. Accordingly, it becomes possible to adjust the rehab menu in accordance with the degree of impairment of the patient as circumstances demand.

The measurement mode and the training mode are provided as the app execution modes. Accordingly, it becomes possible to measure the degree of impairment of the patient and let the patient challenge a new problem. It is possible to expect an increase in the effect of rehab.

The image of the avatar being the virtual trainer is displayed on the image processing apparatus. Accordingly, it is possible to expect an increase in the motivation of the patient for rehab.

The degree of difficulty of the problem is adjusted. Accordingly, it becomes possible to set the problem in accordance with the impairment state of the patient.

A problem in accordance with a weak point of the patient can be set. Accordingly, rehab that improves the weak point of the patient becomes possible.

It is possible to expect an improvement in functional impairment in attention with the number cancellation app.

It is possible to expect improvements in functional impairment in attention and/or spatial perception with the first selection cancellation app.

It is possible to expect improvements in functional impairment in attention and/or inhibition with the second selection cancellation app.

It is possible to expect improvements in functional impairment in spatial perception and/or information acquisition ability with the spatial arrangement app.

It is possible to expect an improvement in functional impairment in spatial perception with the maze app.

It is possible to expect an improvement in functional impairment in executive functioning in the maze app by also setting a problem that prompts cancelling an image of a target together.

It is possible to expect improvements in functional impairment in memory and/or executive functioning with the square move app.

It is possible to expect improvements in functional impairment in spatial perception and/or memory by displaying a virtual image also outside the field of view of the patient.

The image processing apparatus for augmented reality is used to generate a problem that makes a virtual object image used for rehabilitation of higher brain dysfunction appear to exist in a real space. Accordingly, the risk that the patient falls into states such as what is called VR sickness and falling down is reduced. Hence, the patient can undergo rehabilitation safely without feeling strange.

If augmented reality is used, the score is counted, using selection based on the movement of the user. Accordingly, simple scoring becomes possible.

At least images are placed in the field of view of the user, and problems are provided. Consequently, the patient can continue to solve the problems without perplexity.

An image of a problem is placed also outside the field of view of the user. Accordingly, the patient can continue to solve the problems, turning his/her face and moving. Accordingly, brain and physical functions are used at the same time. The effect of rehab based on what is called a dual task can be expected. Also if an image of a problem is placed within the field of view of the user, the patient moves the hand upon tapping. Accordingly, brain and physical functions are used at the same time. Accordingly, the effect of rehab based on a dual task can be expected. Moreover, a case where the patient thinks an image of a problem may be placed outside the field of view, and uses physical functions is also conceivable. Hence, from such a point of view, the effect of rehab based on a dual task can be expected.

The score is counted on the basis of the detection of the position by the tracking unit. Accordingly, rehab that encourages the patient to move becomes possible.

The display of the problem at least in the field of view of the patient ensures encouraging the patient to move.

Moreover, the image is displayed outside the field of view. Accordingly, it becomes possible to further encourage the patient to move.

The program that can execute operation processes of the present invention is provided as a non-transitory recording medium, which can cause a general-purpose image processing apparatus to execute the present invention. Accordingly, the proliferation of the present invention can be expected.

These and other objects, features, phases, and effects of the present invention will be clearer from the following detailed description with reference to the accompanying drawings.

BRIEF DESCRIPTION OF THE DRAWINGS

FIGS. 11(a) and 11(b) are diagrams illustrating an operation image in a case where a maze app is being executed.

FIGS. 12(a) and 12(b) are diagrams illustrating an operation image in a case where a square move app is being executed.

FIG. 13 is a diagram illustrating the data structure of rehab record information stored in the image processing apparatus 5.

FIGS. 14(a) and 14(b) are diagrams illustrating an example of a schedule creation screen used in a schedule creation process (S103) in the doctor-side terminal 2.

FIGS. 15(a) to 15(d) are diagrams illustrating the flow of creating a schedule of when the column of December 20 is selected in the state of FIG. 14(a).

FIGS. 16(a) to 16(c) are diagrams illustrating an example of a rehab menu selection screen on the practitioner-side terminal 4.

FIG. 17(a) is a diagram illustrating an example of a screen for starting a rehab instruction on the practitioner-side terminal 4, and FIG. 17(b) is a diagram illustrating an example of a screen on the practitioner-side terminal 4 during rehab.

FIGS. 18(a) and 18(b) are diagrams illustrating an example of the screen on the practitioner-side terminal 4 during rehab.

FIG. 19 is a diagram illustrating an example of an app execution result screen displayed on the practitioner-side terminal 4.

FIGS. 20(a) and 20(b) are diagrams illustrating an example of the display of the rehab record information on the doctor-side terminal 2.

FIG. 38 is a diagram illustrating an example of an app setting condition settings screen in the first selection cancellation app on the doctor-side terminal 2 and/or the practitioner-side terminal 4.

FIG. 39 is a diagram illustrating an example of an app setting condition settings screen in the second selection cancellation app on the doctor-side terminal 2 and/or the practitioner-side terminal 4.

FIG. 40 is a diagram illustrating an example of an app setting condition settings screen in the spatial arrangement app on the doctor-side terminal 2 and/or the practitioner-side terminal 4.

FIG. 41 is a diagram illustrating an example of an app setting condition settings screen in the maze app on the doctor-side terminal 2 and/or the practitioner-side terminal 4.

FIG. 42 is a diagram illustrating an app setting condition settings screen in the square move app on the doctor-side terminal 2 and/or the practitioner-side terminal 4.

FIG. 43 is an example of a virtual trainer displayed on the image processing apparatus 5.

DESCRIPTION OF THE EMBODIMENTS

First Embodiment

Figure 1:
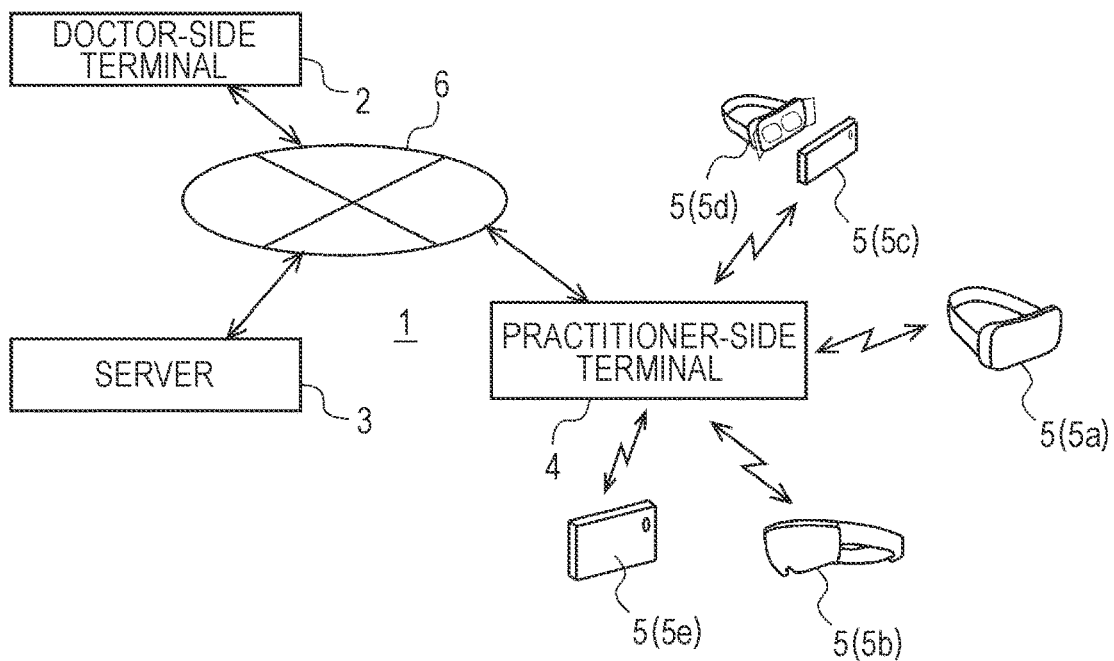
FIG. 1 is a diagram illustrating the entire configuration of a rehabilitation system 1 according to a first embodiment of the present invention.

FIG. 1 is a diagram illustrating the entire configuration of a rehabilitation system 1 according to a first embodiment of the present invention. In FIG. 1, the rehabilitation system 1 includes a doctor-side terminal 2, a server 3, a practitioner-side terminal 4, and an image processing apparatus 5.

The doctor-side terminal 2, the server 3, and the practitioner-side terminal 4 are connected to each other via a network 6 in such a manner as to be capable of communicating with each other. The image processing apparatus 5 and the practitioner-side terminal 4 are connected in such a manner as to be capable of communicating with each other in a wired or wireless manner. Not only a case where the practitioner-side terminal 4 and the image processing apparatus 5 are connected in a rehab facility such as a hospital (in-hospital rehab) but also a case where the practitioner-side terminal 4 and the image processing apparatus 5 are connected via a network (for example, at-home rehab and remote rehab) is assumed in the rehabilitation system 1 of the present invention.

The doctor-side terminal 2 creates a rehabilitation menu (hereinafter referred to as a "rehab menu") for higher brain dysfunction on a patient-by-patient basis, and stores the rehab menu in the server 3. The practitioner-side terminal 4 downloads the rehab menu registered by the doctor-side terminal 2 from the server 3. The practitioner-side terminal 4 instructs the image processing apparatus 5 that is used by a patient to execute rehabilitation related to the downloaded rehab menu. The image processing apparatus 5 displays an image necessary for rehabilitation in accordance with the instructed rehab menu. Rehab record information executed by the image processing apparatus 5 is transmitted to the practitioner-side terminal 4. The practitioner-side terminal 4 uploads the rehab record information to the server 3. The doctor-side terminal 2 displays the state of rehabilitation performed for the patient in a visually understandable manner on the basis of the rehab record information uploaded to the server 3. The rehabilitation system 1 is a system that realizes a doctor's determination on a rehab menu, the performance of rehabilitation on a practitioner side, and the display of the patient's rehabilitation state in this manner.

It is also possible to perform rehabilitation with the practitioner-side terminal 4 and the image processing apparatus 5 without using the doctor-side terminal 2 and the server 3. An embodiment thereof is described in a second embodiment.

The rehabilitation system 1 of the embodiment is described assuming that the system is present in a stand-alone basis. However, it is also possible to incorporate the rehabilitation system of the present invention into a part of medical groupware, an electronic medical chart system, or another medical system to operate the rehabilitation system. Therefore, the present invention also includes a rehabilitation system that operates, incorporated in another medical system.

The doctor-side terminal 2 is a computer apparatus that is used by a doctor. The designation of the doctor-side terminal 2 is not particularly limited as long as the doctor-side terminal 2 is an information processing apparatus such as a personal computer, a workstation, a tablet terminal, or a smartphone. When a plurality of doctors uses the doctor-side terminals 2, the doctors may use their respective doctor-side terminals 2. Moreover, a plurality of doctors may share one doctor-side terminal 2 and sets their own account for use. In addition, a doctor can use the doctor-side terminal 2 in every known method.

The practitioner-side terminal 4 is a computer apparatus that is used by a practitioner such as an occupational therapist. The designation of the practitioner-side terminal 4 is not particularly limited as long as the practitioner-side terminal 4 is an information processing apparatus such as a personal computer, a workstation, a tablet terminal, or a smartphone. The practitioner is a person who rehabilitates a patient, and is not limited to an occupational therapist, and also includes a physiotherapist, nurse, doctor, caregiver, acupuncturest, family, and acquaintance on the part of the invention. In the invention, the term practitioner is used as a concept irrespective of the possession or non-possession of a qualification. Also in terms of the practitioner-side terminal 4, the practitioners may use their respective practitioner-side terminals 4. Alternatively, a plurality of practitioners may share one practitioner-side terminal 4, and set their own account for use. In addition, the practitioner can use the practitioner-side terminal 4 in every known method.

The server 3 is a computer apparatus that executes a program for saving, for example, the patient's data used in the rehabilitation system 1, creating a rehabilitation schedule, and displaying rehab record information. One server 3 is illustrated here; however, a plurality of the servers 3 may be used to save data and execute the program. Moreover, a server that saves data and a server that executes the program may be present as different apparatuses. In addition, the server 3 can be constructed in every known method.

Examples of the image processing apparatus 5 include a head mounted display (HMD) 5a, HOLOLENS (registered trademark) 5b made by Microsoft (registered trademark) Corporation, a device 5c such as a smartphone or tablet terminal, a pair of goggles 5d where the device 5c is mounted, and a touch input display device 5e such as a tablet terminal or smartphone. FIG. 1 illustrates three image processing apparatuses 5. However, the number of the image processing apparatuses 5 is not limited. Each patient may possess the image processing apparatus 5, or a plurality of patients may share and use the image processing apparatus 5. The term HMD is used in some cases in the embodiment in the description and drawings, which is not, however, intended to limit the image processing apparatus 5 to a head mounted display. The term HMD is simply used to abbreviate the image processing apparatus 5.

A technology used in the image processing apparatus 5 is any of virtual reality (VR: Virtual Reality), augmented reality (AR: Augmented Reality), and mixed reality (MR: Mixed Reality). Various classification methods for virtual reality, augmented reality, and mixed reality are conceivable. However, in the description, a description is given, assuming that virtual reality, augmented reality, and mixed reality have the following significance:

If virtual reality is used, the image processing apparatus 5 displays an image related to a virtual space, and makes a user perceive as if the user is actually present in the virtual space. Generally, if virtual reality is used, a displayed image changes in response to the movement of a user, which can make the user perceive as if the user is moving in the virtual space. If virtual reality is used, three-dimensional information of an object in the virtual space, and tracking information such as the position and inclination of the image processing apparatus 5 and the user's line of sight are required. From where and in which direction in the virtual space the user sees the virtual space is calculated. An image in the virtual space is displayed on the image processing apparatus 5 on the basis of the calculation.

In the following description, a description is given, taking, as an example, a case where the user's line of sight is detected by, for example, an eye tracking function in virtual reality and augmented reality. However, it is simply required to identify at least the orientation of a user, which direction a user is facing. Therefore, all parts that are described as the user's line of sight can be replaced with and read as the orientation of the user. In this case, the invention shall be understood, assuming that an orientation detection unit 59 is used instead of a line-of-sight detection unit 59 in the image processing apparatus 5. The user's line of sight is a concept included in the orientation of the user. The line-of-sight detection unit 59 is a concept included in the orientation detection unit 59. The line-of-sight detection unit 59 can use, for example, neck movement sensing as a specific means for detecting the orientation of the user, other than the line of sight, which, however, does not limit the present invention.

If augmented reality is used, an image of a virtual object is superimposed on a real image obtained by the image processing apparatus 5. The composite image is displayed. In augmented reality, a real image where a virtual object is superimposed is recognized. An image of the virtual object is superimposed on the recognized real image. Hence, in the description, the image processing apparatus 5 is assumed to not have tracking information such as the position and inclination of the image processing apparatus 5 and the user's line of sight as in virtual reality and mixed reality. However, this definition is simply a definition in the description to make the description easy to understand. In the present invention, it is needless to say that there is no problem in realizing the present invention with augmented reality, using the image processing apparatus that can obtain tracking information.

If the display device 5e is used, a case of AR is mainly assumed. The patient moves the display device 5e such as a tablet terminal while showing real-space surroundings with a camera of the display device 5e, carrying the display device 5e. A virtual-space object is superimposed on a real-space video by image composition in accordance with the patient's movement. However, the case of AR is not limited to the display device 5e.

In mixed reality, spatial recognition is realized in which a real space is recognized as a three-dimensional shape by image recognition, a depth camera, infrared sensor, laser irradiation, and other various sensors and detectors. If mixed reality is used, the image processing apparatus 5 displays an image that looks as if an object exists in the recognized real space, and makes the user perceive as if the virtual object exists in the real space. Furthermore, if mixed reality is used, the image processing apparatus 5 can recognize, for example, the position and inclination of the image processing apparatus 5 and the user's line of sight (tracking information) in the real space, and can offer a display that can make the user perceive as if the virtual object remains left in the real space in accordance with the movement of the user in the real space. In the case of mixed reality, the image processing apparatus 5 can detect the user's line of sight and can grasp which direction the user is facing. Hence, the image processing apparatus 5 can also change an image to be displayed in accordance with the orientation of the user. Furthermore, in mixed reality, it is assumed that the movements of the user's finger and hand are detected to enable, for example, the selection of the virtual object.

Various spatial recognition methods in mixed reality have been proposed. For example, singular points on an image are extracted. A plurality of the extracted singular points is converted to three-dimensional coordinates to grasp surrounding three-dimensional shapes and furthermore identify his/her own position.

The embodiment assumes the case of using mixed reality. However, embodiments of the cases of using virtual reality and augmented reality are also described as appropriate. The rehabilitation system of the present invention can be realized using not only mixed reality but also virtual reality and augmented reality.

Moreover, information related to the position and inclination of the image processing apparatus 5 and the user's line of sight is collectively referred to as tracking information. The position and inclination of the image processing apparatus 5 are detected to detect the position and inclination of the user. Accordingly, a description is given assuming that the tracking information of the image processing apparatus 5 is synonymous with the tracking information of the user.

Figure 2:
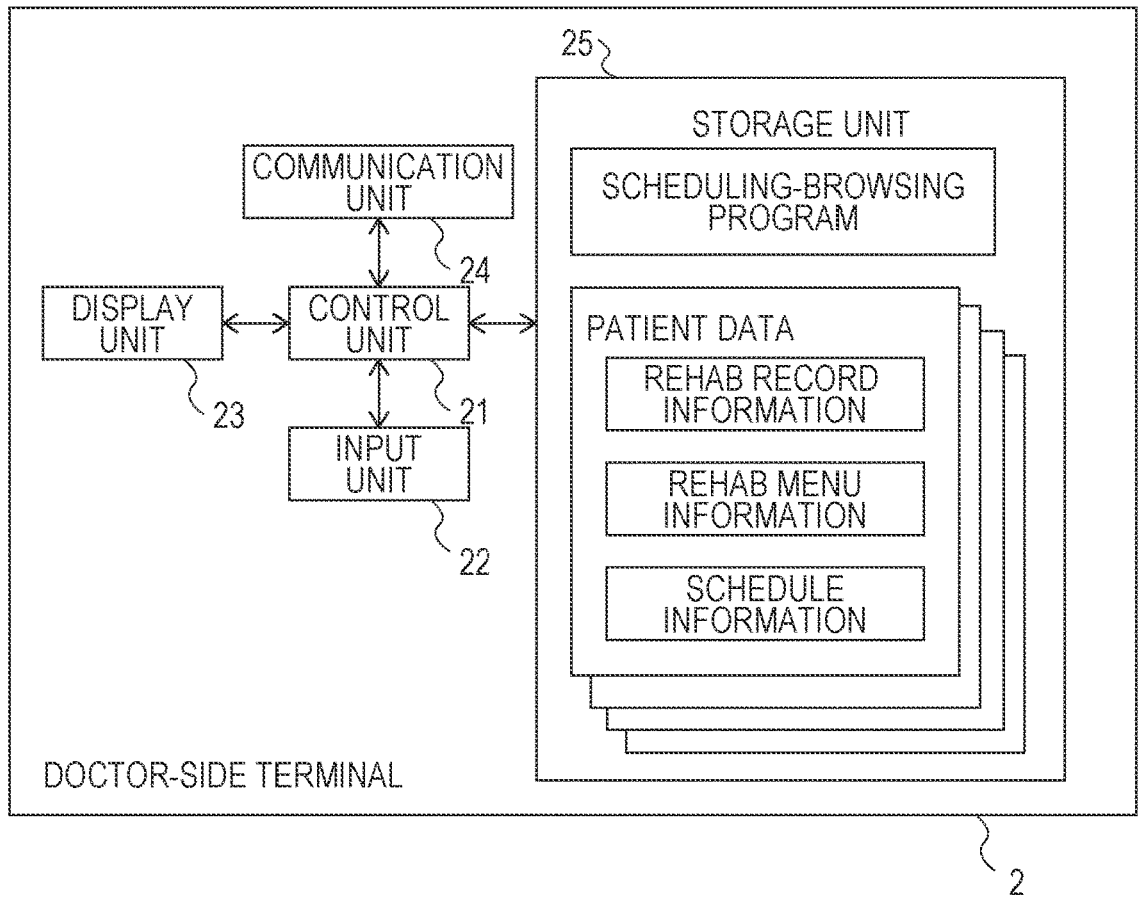
FIG. 2 is a block diagram illustrating the functional configuration of a doctor-side terminal 2.

FIG. 2 is a block diagram illustrating the functional configuration of the doctor-side terminal 2. In FIG. 2, the doctor-side terminal 2 includes a control unit 21, an input unit 22, a display unit 23, a communication unit 24, and a storage unit 25.

The control unit 21 reads a program necessary to execute the rehabilitation system 1, from the storage unit 25, executes the program, and controls the operation of the doctor-side terminal 2. The input unit 22 is a device for operating the doctor-side terminal 2, such as a keyboard, a mouse, or a touchscreen. The display unit 23 is a display device such as a display. The communication unit 24 is a device for enabling communication with the external server 3 via the network 6.

The storage unit 25 is a recording medium such as memory or a hard disk. Patient data of each patient downloaded from the server 3, in addition to a scheduling-browsing program that is executed in the control unit 21, is recorded in the storage unit 25.

If a return from the server 3 is displayed on the doctor-side terminal 2, and if scheduling and the viewing of the patient data are made possible on the doctor-side terminal 2, it is possible to cause a general browser program to function as the scheduling-browsing program. Such a technology is a known matter, and a detailed description thereof is omitted here.

The server 3 is responsible for the saving of the patient data. The patient data is temporarily saved in the storage unit 25 of the doctor-side terminal 2. The server 3 and the doctor-side terminal 2 cooperate with each other to provide a display based on the temporarily saved patient data on the doctor-side terminal 2. However, the doctor-side terminal 2 may save the patient data in the storage unit 25 in a non-temporary manner.

Figure 3:
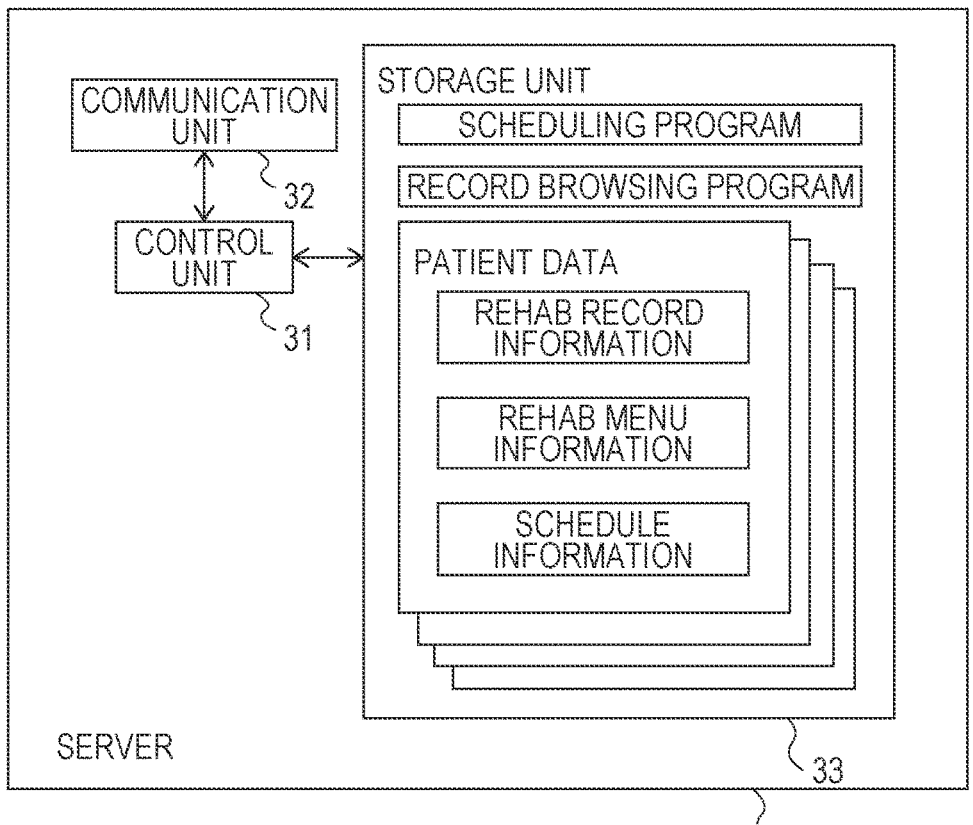
FIG. 3 is a block diagram illustrating the functional configuration of a server 3.

FIG. 3 is a block diagram illustrating the functional configuration of the server 3. The server 3 includes a control unit 31, a communication unit 32, and a storage unit 33. The control unit 31 of the server 3 executes a scheduling program and/or a record browsing program, which are stored in the storage unit 33, at instructions of the doctor-side terminal 2 and the practitioner-side terminal 4 obtained via the communication unit 32, and returns the execution results to the doctor-side terminal 2 and the practitioner-side terminal 4.

A user who operates the doctor-side terminal 2 (typically, a "doctor" but not limited to a doctor) uses the input unit 22 to access the server 3. The control unit 21 accesses the server 3 via the communication unit 24 at the instruction of the input unit 22, and registers a rehab schedule. Moreover, the control unit 21 downloads necessary patient data of patients and stores the patient data in the storage unit 25.

The control unit 21 creates a rehab menu of a patient targeted for treatment in cooperation with the program on the server 3 in accordance with the user's input via the input unit 22. The control unit 21 stores the created rehab menu in the server 3. Moreover, the control unit 21 downloads patient data obtained from the server 3 and displays a rehab record of the patient on the display unit 23.

An embodiment where the server 3 manages schedules and rehab record information is assumed here. However, if the server 3 is simply treated as a recording device that exchanges data with the practitioner-side terminal 4, the doctor-side terminal 2 may be configured in such a manner as to execute programs corresponding to the scheduling program and the record browsing program.

In other words, in the rehabilitation system of the present invention, the functions of each of the doctor-side terminal 2, the server 3, the practitioner-side terminal 4, and the image processing apparatus 5 are simply required to be provided somewhere in the entire system. It is not necessarily required to provide these functions to the apparatuses described below. For example, the practitioner-side terminal 4 may include part of the functions of the image processing apparatus 5. Moreover, the doctor-side terminal 2 and the server 3 may include part of the functions of the practitioner-side terminal 4.

Figure 4:
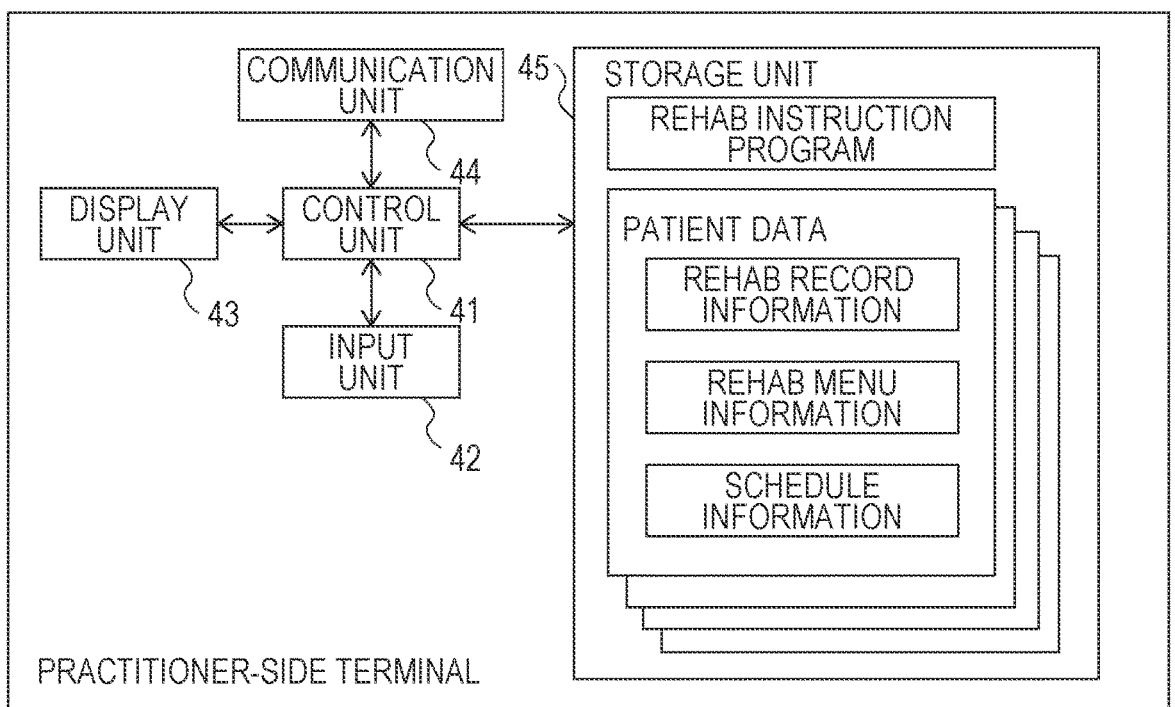
FIG. 4 is a block diagram illustrating the functional configuration of a practitioner-side terminal 4.

FIG. 4 is a block diagram illustrating the functional configuration of the practitioner-side terminal 4. The practitioner-side terminal 4 includes a control unit 41, an input unit 42, a display unit 43, a communication unit 44, and a storage unit 45.

The control unit 41 executes a rehab instruction program stored in the storage unit 4, and controls the operation of the practitioner-side terminal 4. The input unit 42 is a device for operating the practitioner-side terminal 4, such as a keyboard, a mouse, or a touchscreen. The display unit 43 is a display device such as a display. The communication unit 44 is a device for enabling communication with the external server 3 via the network 6. The communication unit 44 is a device for communicating with the image processing apparatus 5. The network 6 is, for example, the Internet or an on-site LAN, and the type of network is not particularly limited. Communication between the communication unit 44 and the image processing apparatus 5 is, for example, wired or wireless, and the type of communication is not particularly limited.

The storage unit 45 is a recording medium such as memory or a hard disk. The rehab instruction program and the patient data of each patient downloaded from the server 3 are recorded in the storage unit 45. The server 3 is responsible for the saving of the patient data. The patient data is temporarily saved in the storage unit 45 of the practitioner-side terminal 4. The temporarily saved patient data is uploaded to the server 3 by the rehab instruction program. However, the patient data may be saved in a non-temporary manner in the storage unit 45 in the practitioner-side terminal 4.

The practitioner-side terminal 4 executes the rehab instruction program, instructs the image processing apparatus 5 to execute rehab, acquires rehab record information from the image processing apparatus 5, and transmits the rehab record information to the server 3.

The patient data is described here. Naturally, basic information such as the name, date of birth, and outpatient record of a patient is stored as the patient data. In addition, "rehab record information" presenting a detailed record of rehabilitation, "rehab menu information" presenting the details of a rehabilitation menu, and "schedule information" presenting a rehabilitation schedule are used as the patient data.

The patient data is saved in the server 3. It is configured in such a manner that the doctor-side terminal 2 and the practitioner-side terminal 4 can access the latest patient data. Naturally, the patient data is appropriately backed up by use of every known method and also is provided with security in order to prevent unauthorized acquisition from the outside.

Figure 5:
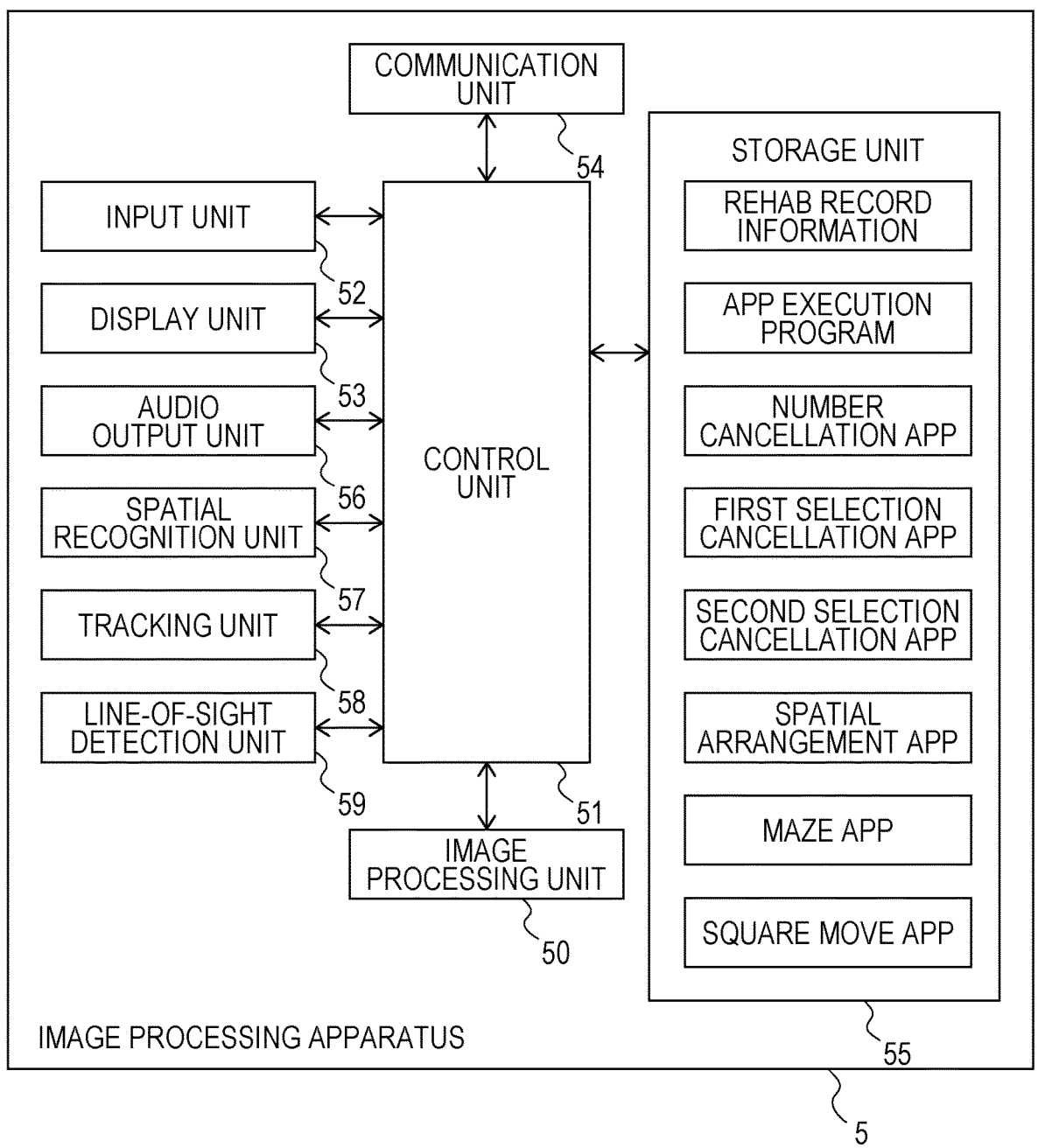
FIG. 5 is a block diagram illustrating the functional configuration of an image processing apparatus 5.

FIG. 5 is a block diagram illustrating the functional configuration of the image processing apparatus 5. In FIG. 5, the image processing apparatus 5 includes a control unit 51, an input unit 52, a display unit 53, a communication unit 54, a storage unit 55, an audio output unit 56, a spatial recognition unit 57, a tracking unit 58, the line-of-sight detection unit 59, and an image processing unit 50.

The control unit 51 controls the operation of the entire image processing apparatus 5.

The input unit 52 is a device for operating the image processing apparatus 5, such as a wired or wireless switch or touchscreen. In terms of the image processing apparatus 5, the image processing apparatus 5 can also be operated by recognizing a gesture of the user. Accordingly, it is also possible to take an unillustrated camera and image recognition processing unit as functioning as the input unit 52. Furthermore, if the line of sight stays at a fixed point for a fixed period of time (a case of what is called a gaze), it can also be said that an operation called selection is performed. Accordingly, it is also possible to understand that a process that is taken as the operation of the control unit 51 on the basis of information from the line-of-sight detection unit 59 is a process by the input unit 52.

The display unit 53 is a device for displaying generated images. In a case of the HMD 5*a* for VR, the display unit 53 is small displays for the left and right eyes. In the HMD 5*a* for VR, the background may be see-through or non see-through. In a case of HOLOLENS (registered trademark) 5*b* for MR, the display unit 53 is small displays for the left and right eyes. In the case of HOLOLENS (registered trademark) 5*b* for MR, the background is see-through. If the image processing apparatus 5 is constructed by the device 5*c* such as a smartphone and the pair of goggles 5*d* where the device 5*c* is mounted, a display screen of the device 5*c* serves as the display unit 53.

HOLOLENS (registered trademark) 5*b* made by Microsoft (registered trademark) Corporation is illustrated here as an example of MR. However, it is needless to say that any other device for MR is also acceptable. If the case of MR, it may be configured in such a manner that a real space can be perceived, seen through the lens, or it may be configured in such a manner as to display a real-time image of a real space captured by the camera on the small display to superimpose a virtual object on the real-time image. MR may thus be realized. In addition, a device that realizes MR using every known method is included in the image processing apparatus 5.

The communication unit 54 is a device that can communicate with at least the practitioner-side terminal 4, but may be capable of communicating in between with the network 6.

The storage unit 55 is a recording medium such as memory. An app execution program that controls the operation of an app, the rehab record information, a number cancellation app, a first selection cancellation app, a second selection cancellation app, a spatial arrangement app, a maze app, and a square move app are stored in the storage unit 55. It is simply required that one of the number cancellation app, the first selection cancellation app, the second selection cancellation app, the spatial arrangement app, the maze app, and the square move app is stored. It is not necessarily required to store all the apps for rehab. The details of each app for rehab are described later in turn.

If a new app for rehab is developed in the future, the image processing apparatus 5 can add the new app for rehab in the storage unit 55 through communication with the practitioner-side terminal 4 and communication with the network 6.

The app execution program is read into the control unit 51 and executed. Accordingly, it becomes possible to realize instructing each app for rehab to start operating, setting operating conditions of each app for rehab (called "app setting conditions"), storing the rehab record information, and transmitting the rehab record information to the practitioner-side terminal 4.

The audio output unit 56 is a speaker or earphone. The audio output unit 56 outputs, for example, correct and incorrect answer sounds for problems, a start sound of execution of an app for rehab, and sounds during the execution of the app for rehab at the instruction of the control unit 51.

The spatial recognition unit 57 includes a camera, and recognizes the three-dimensional shape of a surrounding space of the image processing apparatus 5, using an image recognition technology. Various technologies for recognizing a three-dimensional shape of a space by image capturing with a camera have already been developed. Accordingly, it is assumed here that any of the technologies is used to perform spatial recognition. The spatial recognition unit 57 may not be provided if VR and AR are used.

Apps that require spatial recognition by the spatial recognition unit 57 include the spatial arrangement app, the maze app, and the square move app. In terms of the number cancellation app, and the first and second selection cancellation apps, it is possible to cause the display unit 53 to display as if a virtual-space object is placed in a real space, without performing the spatial recognition process. However, also in the number cancellation app, and the first and second selection cancellation apps, the placement of a virtual-space object after spatial recognition leads to more correct placement.

The tracking unit 58 recognizes, for example, the position and inclination of the image processing apparatus 5. Various tracking technologies in VR and MR have already been developed. Accordingly, it is assumed here that any of the technologies is used to recognize the position and inclination.

The tracking unit 58 may be configured in such a manner as to detect, for example, the position and inclination by not only, for example, a sensor structurally included in a housing of the image processing apparatus 5 but also, for example, a sensor attached to the outside of the housing. Therefore, the image processing apparatus 5 may achieve not only inside-out tracking but also outside-in tracking. In this case, the tracking unit 58 is present outside the housing of the image processing apparatus 5. However, the image processing apparatus 5 is assumed to include the tracking unit 58 present outside the housing.

The line-of-sight detection unit 59 is a device that detects the line of sight of a user who is using the image processing apparatus 5. Various technologies for detecting the line of sight in VR and MR have already been developed. Accordingly, it is assumed here that any of the technologies is used to recognize the line of sight. If the detection of the line of sight is taken as a part of the tracking technology, the line-of-sight detection unit 59 may be taken as being included in the tracking unit 58.

The image processing unit 50 generates a three-dimensional image to be displayed on the display unit 53. Original data of a three-dimensional image is called here three-dimensional data. The image processing unit 50 stores a three-dimensional structure of a real space recognized by the spatial recognition unit 57 as three-dimensional data in the storage unit 55 during execution of each app for rehab. The image processing unit 50 stores, in the storage unit 55, three-dimensional data of a virtual object to be placed with the same coordinate axes as the three-dimensional data of the three-dimensional structure of the real space. The image processing unit 50 also stores, in the storage unit 55, three-dimensional data of tracking information (position, inclination, and line of sight) with the same coordinate axes as the three-dimensional data of the three-dimensional structure of the real space. These three types of three-dimensional data are managed with the same coordinate axes. Accordingly, the image processing unit 50 can generate an image of a virtual object seen in the line of sight of the patient, and display the image on the display unit 53.

The load of processing three-dimensional data is heavy. Accordingly, the image processing unit 50 is configured in such a manner as to calculate three-dimensional data, isolated from the control unit 51; however, naturally, that the control unit 51 may be configured in such a manner as to calculate three-dimensional data.

The patient clears up a presented task, looking at the image displayed on the display unit 53.

Figure 6:
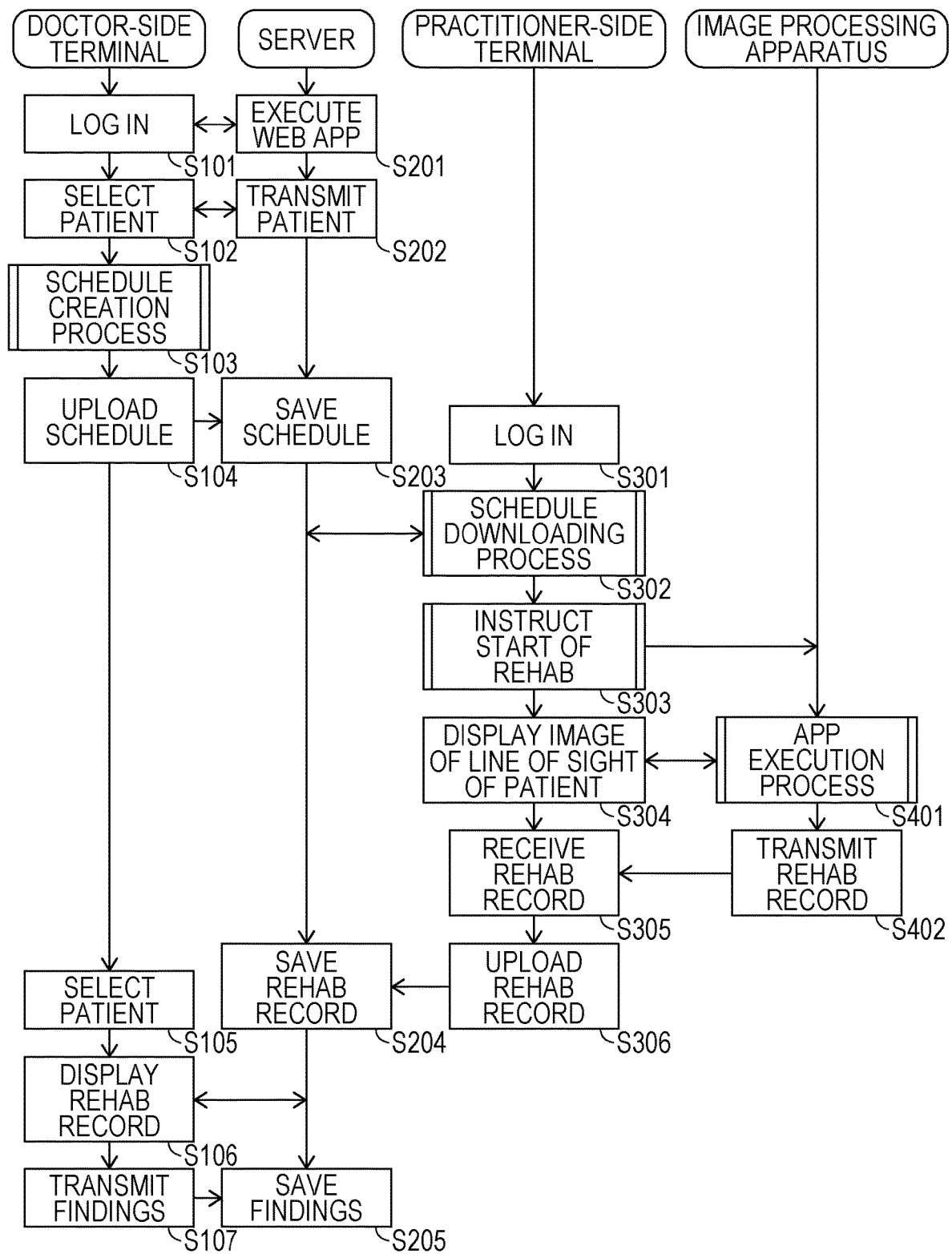
FIG. 6 is a flowchart illustrating the flow of the entire operation of each apparatus in the rehabilitation system 1.

FIG. 6 is a flowchart illustrating the flow of the entire operation of each apparatus in the rehabilitation system 1.

Firstly, the doctor-side terminal 2 logs into the server 3 (S101). In response to the login of the doctor-side terminal 2, the server 3 executes the scheduling program and the record browsing program (S201). Screens for creating a rehabilitation menu, managing a schedule, and displaying rehab record information are displayed on the doctor-side terminal 2. On the doctor-side terminal 2, a rehabilitation menu is created, a schedule is managed, and rehab record information is displayed while the screens are viewed.

The embodiment is what is called a cloud system. Accordingly, there is no need to install software on the doctor-side terminal 2 as mentioned above. However, the present invention also includes an embodiment where software is installed on the doctor-side terminal 2 to create a rehabilitation menu, manage a schedule, and display rehab record information. In a case of this embodiment, the server 3 mainly plays a role as a recording apparatus that records a schedule, a rehab menu, and rehab record information. The operation of the doctor-side terminal 2 in the case where software is installed on the doctor-side terminal 2 is roughly similar to the operation in the case of the cloud system, and is fully feasible for those skilled in the art by invoking the operation in the case of the cloud system. Accordingly, a detailed description thereof is omitted.

Return to the description of FIG. 6. The doctor-side terminal 2 selects a patient who schedules rehab (S102). It is configured in such a manner that, at this point in time, the name of a patient whom the doctor is in charge of is transmitted from the server 3 to the doctor-side terminal 2 (S202) and that the doctor-side terminal 2 can select a patient. The server 3 may be searched for a patient stored therein by the doctor-side terminal 2 to select the patient on the doctor-side terminal 2 on the basis of the search results.

Next, a schedule creation process for the rehab menu is executed on the doctor-side terminal 2 (S103). The created schedule is uploaded to the server 3 (S104). The server 3 saves the uploaded rehab menu information and schedule information (S203). Information linked to the patient data is the rehab record information, the rehab menu information, and the schedule information. The rehab menu information includes which app is used, and what are app setting conditions for the use of the app. The schedule information includes the rehab menu information linked to the date and time of treatment.

Typically, the operations up to this point are executed by the doctor before the date and time of treatment. Next, the description shifts to operations in the practitioner-side terminal 4 in a case where the date and time of treatment is approaching.

The practitioner-side terminal 4 logs into the server 3 (S301). A necessary schedule is then downloaded (S302). The practitioner-side terminal 4 instructs the image-processing apparatus 5 to execute a rehab menu app registered in the downloaded schedule (S303). Typically, the practitioner instructs the start of the app, but the patient himself/herself may give the instruction.

The image processing apparatus 5 executes the relevant app for rehab at the instruction to start rehab (S401). During the execution of the app, the score is counted. Moreover, the image processing apparatus 5 transmits what kind of image is being viewed in the patient's line of sight to the practitioner-side terminal 4. The image viewed by the patient is displayed on the practitioner-side terminal 4 (S304). If the see-through image processing apparatus 5 is used, a composite image of a real image captured by the camera of the image processing apparatus 5 and a virtual object is displayed on the practitioner-side terminal 4.

After the execution of the app for rehab is ended, the image processing apparatus 5 transmits the rehab record information to the practitioner-side terminal 4 (S402). The practitioner-side terminal 4 receives the transmitted rehab record information (S305). The practitioner-side terminal 4 uploads the rehab record information to the server 3, at the practitioner's instruction or automatically (S306).

The server 3 saves the transmitted rehab record information (S204).

Before S105, the doctor-side terminal 2 may be temporarily logged out and logged in again, and then the operation of S105 may be performed. If the doctor has selected a patient (S105), the doctor-side terminal 2 downloads the rehab record information of the selected patient, and displays the rehab record (S106). The doctor-side terminal 2 transmits findings inputted by the doctor to the server 3 in such a manner as to link the findings to the rehab record information, if necessary (S107). The server 3 links the findings to the rehab record information, and saves the findings (S205).

The above description is the entire operation of the rehabilitation system 1. Next, a rough outline of the entire operation of the rehabilitation system 1 is described, presenting specific screen examples, data structures, and rehab images. It is needless to say that the illustrative screen examples, data structures, and rehab images are mere examples, and do not at all limit the present invention. It is needless to say that they can be changed, using technical common sense of those skilled in the art as appropriate.

Figure 7:
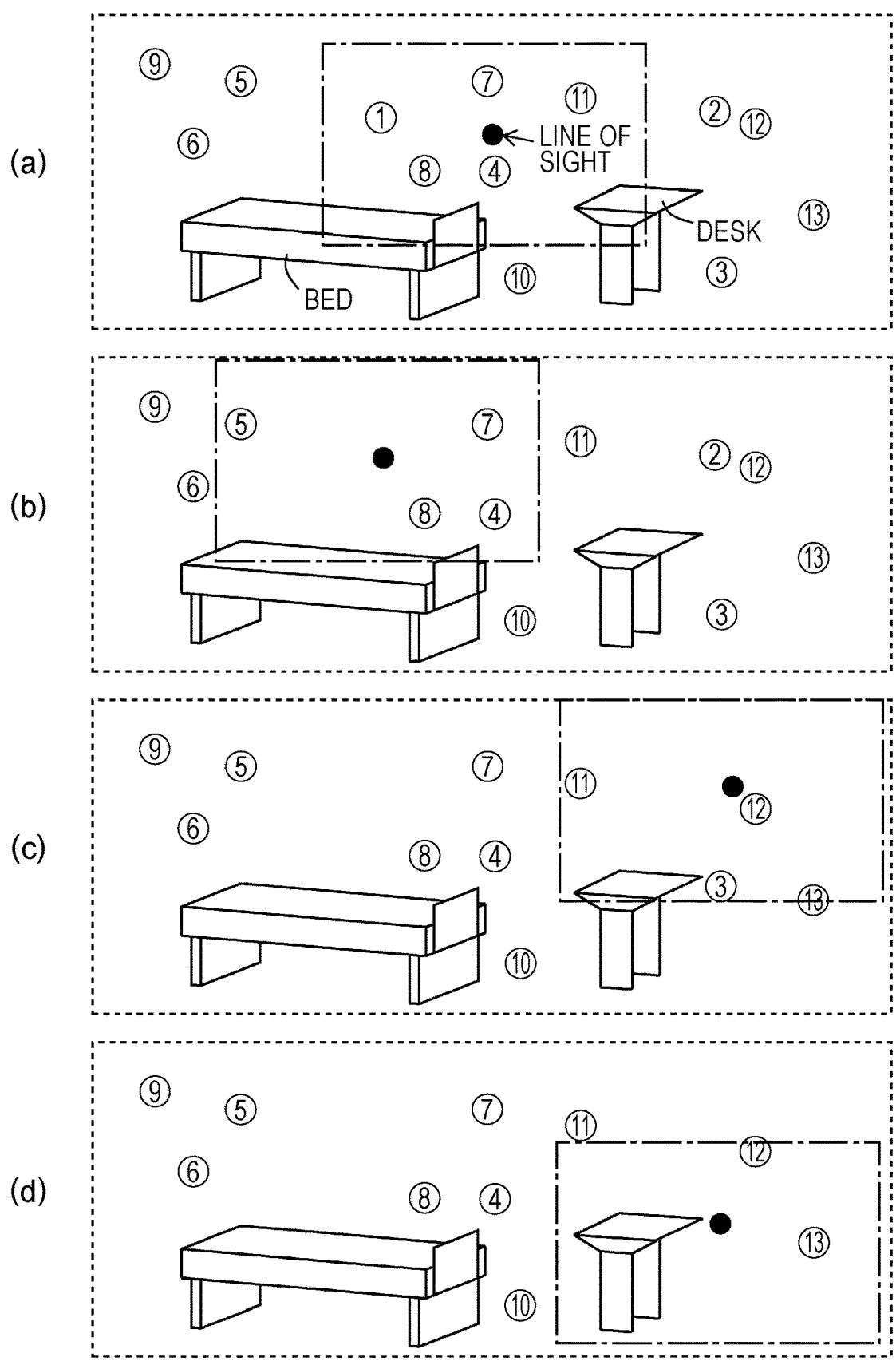
FIGS. 7(a) to 7(d) are diagrams illustrating an operation image in a case where a number cancellation app is being executed.

FIGS. 7(*a*) to 7(*d*) are diagrams illustrating an operation image in a case where the number cancellation app is being executed. In FIGS. 7(*a*) to 7(*d*), the frame indicated by a broken line is assumed to be the entire space. The entire space here is a space created virtually in a case of VR. It is assumed that a bed and a desk are virtually placed in the virtual space. The entire space indicates a real space around a patient in cases of AR and MR. The examples of FIGS. 7(*a*) to 7(*d*) illustrate by example that the bed and the desk exist in the real space.

In FIGS. 7(*a*) to 7(*d*), the area indicated by a dot-and-dash line indicates the area of the field of view within which a patient wearing the image processing apparatus 5 can see. The field of view is a part of the virtual or real space. Accordingly, the dot-and-dash line indicates an area smaller than the broken-line part.

The image processing apparatus 5 places numbers from 1 to 13 in the virtual or real space.

If MR is used, the three-dimensional shape of a real space is recognized by spatial recognition, and converted into three-dimensional data. The image processing apparatus 5 then places three-dimensional data of a virtual object on the same three-dimensional coordinates, and displays on the display unit 53 as if the virtual object exists in the real space that is actually seen. In MR, an image that looks as if the virtual object exists is displayed in the real space that is actually, visually recognized by the user, and the real space seen by the user is an actual space unlike VR.

If VR is used, the numbers are placed on three-dimensional data of a virtual space, and the image processing apparatus 5 displays an image of the virtual space where the numbers are placed, on the display unit 53, on the basis of three-dimensional data after the placement. In VR, an image of the surroundings of an object is a virtual-space image.

If AR is used, the image processing apparatus 5 superimposes a virtual object on a real-space image captured by the camera, and displays the composite image on the display unit 53. In AR, surroundings of the object are an actually captured real-space image. The virtual object image is superimposed on the real-space image. In AR, the user is viewing the image where the virtual object image is superimposed on the real-space image, which is different from MR that shows the user the actual real space.

A limited area called the field of view of the patient does exist in the entire space in all the cases of using the technologies of VR, AR, and MR.

The virtual objects (here, the numbers) are placed throughout the space. The image processing apparatus 5 is moved to enable the patient to look for the numbers placed throughout the space. Assume a rule that the numbers are deleted sequentially, starting at one. In a case of FIG. 7(*a*), it is assumed that the face and eyes are moved to move the line of sight and that the line of sight is brought onto the number one. The field of view is then moved to the left in the figure and the video seen by the patient is also changed as illustrated in FIG. 7(*b*). The line of sight is moved onto the number one. The input unit 52 is operated, a deletion gesture is made, or a gaze (the act of fixing the line of sight on an object for a fixed period of time) is given; accordingly, the number one can be deleted. An act for selecting or deleting an object is collectively called a tap below. The tap includes at least a gesture for selection or deletion, the operation of the input unit 52, and a gaze, and is also assumed to include a known selection or deletion method (for example, selection or deletion by sound recognition).

Next, when the line of sight is moved to the right in the figure, the line of sight can be brought onto the number two as illustrated in FIG. 7(*c*). The number two is then deleted likewise. Furthermore, the line of sight is moved downward in the figure, the number three comes within sight, and can be deleted as illustrated in FIG. 7(*d*).

In all the cases of VR, AR, and MR, it is possible to similarly perform rehabilitation where numbers are placed in a space, and deleted on the basis of a specified rule.

It is possible to expect an improvement in the attention of a patient with higher brain dysfunction with the number cancellation app. As a result of rehab that was provided by, for example, the present inventors on an actual rehab site, using the number cancellation app, the effects of improvement in information processing speed, working memory, general cognitive function were also observed.

Figure 8:
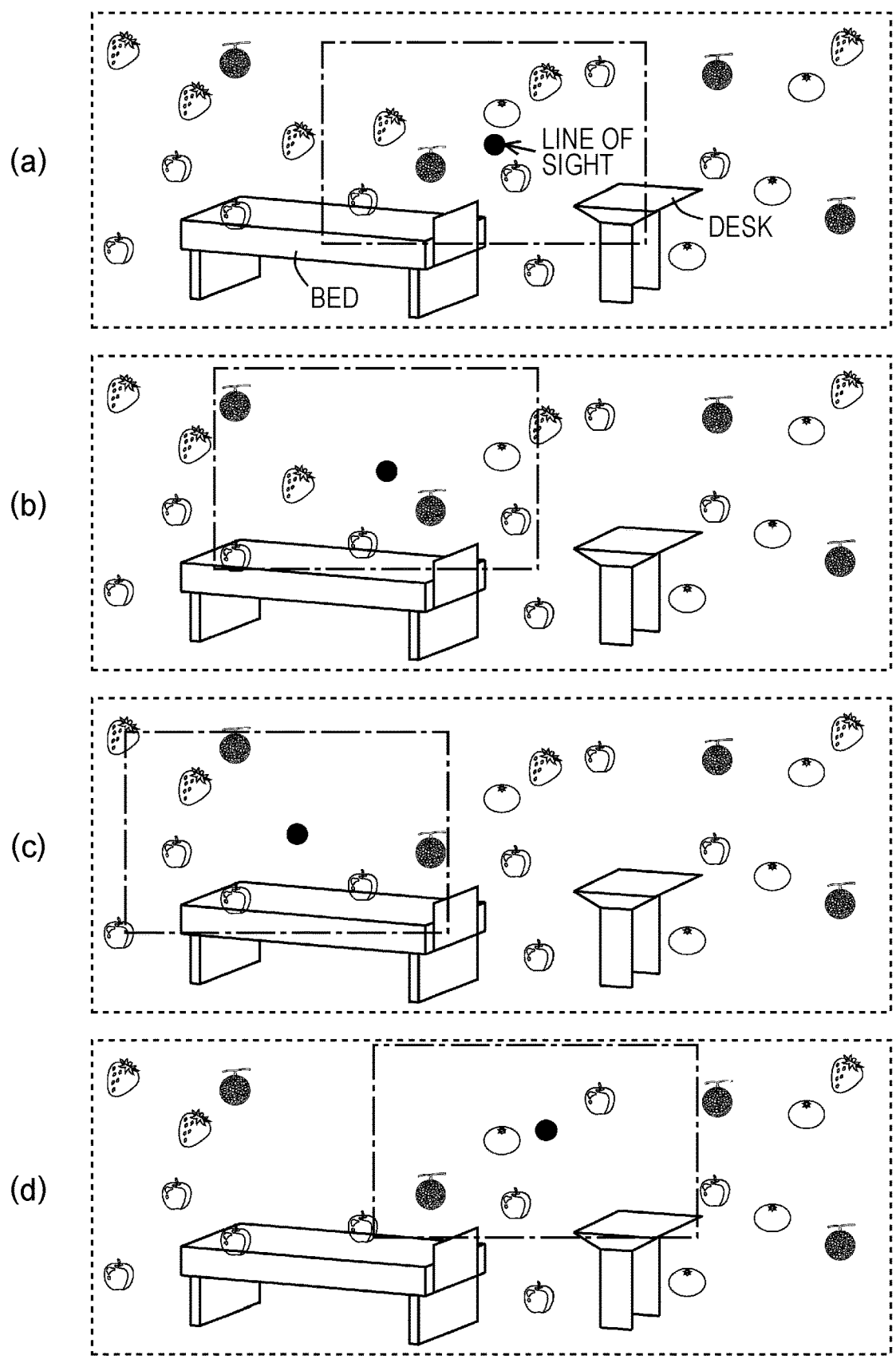
FIGS. 8(a) to 8(d) are diagrams illustrating an operation image in a case where a first selection cancellation app is being executed.

FIGS. 8(*a*) to 8(*d*) are diagrams illustrating an operation image in a case where the first selection cancellation app is being executed. A presentation method in FIGS. 8(*a*) to 8(*d*) is similar to FIGS. 7(*a*) to 7(*d*). In the first selection cancellation app, various illustrations are displayed instead of the numbers of the number cancellation app. A method for drawing various illustrations is similar to the case of the number cancellation app in all of VR, AR, and MR.

In the first selection cancellation app, a user selects and then cancels specified illustrations one by one. As in the number cancellation app, the user moves the line of sight, and brings the line of sight onto a deletion target illustration. In an example of FIG. 8(*a*), a "strawberry" that is up and to the left of the line of sight is assumed to be a target illustration. As illustrated in FIG. 8(*b*), the line of sight is placed on the "strawberry", and tapped and deleted in a similar method to the number cancellation app. The target here is a virtual-space object, and indicates a selection or deletion target. A non-target indicates a virtual-space object that is not targeted for selection or deletion.

Next, a "strawberry" that is to the left of the line of sight in FIG. 8(*b*) is similarly deleted (refer to FIG. 8(*c*)). Moreover, as illustrated in FIG. 8(*d*), a "strawberry" that is up and to the right is similarly deleted.

The number of targets for deletion is not limited to one. A plurality of different types of targets may be targeted for deletion.

It is possible to expect improvements in the attention and/or spatial perception of a patient with higher brain dysfunction with the first selection cancellation app. As a result of rehab that was provided by, for example, the present inventors on an actual rehab site, using the first selection cancellation app, contribution to the attention function and the spatial perception function has been found.

Figure 9:
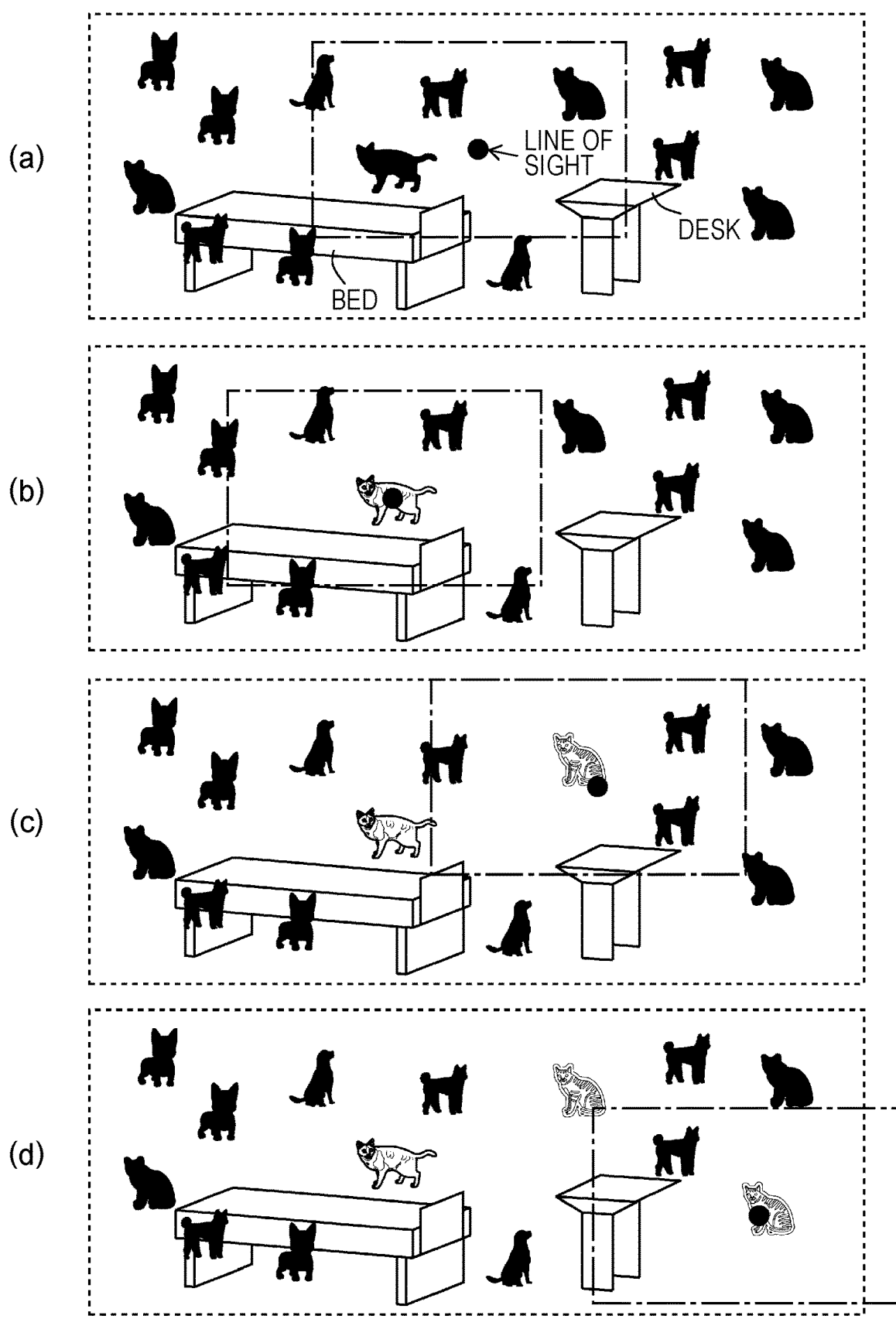
FIGS. 9(a) to 9(d) are diagrams illustrating an operation image in a case where a second selection cancellation app is being executed.

FIGS. 9(*a*) to 9(*d*) are diagrams illustrating an operation image in a case where the second selection cancellation app is being executed. A presentation method of FIGS. 9(*a*) to 9(*d*) is similar to FIGS. 7(*a*) to 7(*d*). In the second selection cancellation app, various illustrations are displayed instead of the numbers of the number cancellation app. A method for drawing various illustrations is similar to the case of the number cancellation app in all of VR, AR, and MR.

In the second selection cancellation app, a user makes selections by selecting specified illustrations one by one. As in the number cancellation app, the user moves the line of sight, and brings the line of sight onto a selection target illustration. In an example of FIG. 9(*a*), a "cat" that is to the left of the line of sight is assumed to be a target illustration. As illustrated in FIG. 9(*b*), the line of sight is placed on the "cat" to select the "cat" in a method similar to the number cancellation app.

In the second selection cancellation app, a process after the selection is different from the first selection cancellation app. In the second selection cancellation app, the selected target illustration changes. It is assumed here that the black illustration changes to white. However, how an illustration changes is not particularly limited. It may be a change in other than color, for example, a change of a target in an illustration from a standing position in a seated position.

Next, a "cat" that is up and to the right of the line of sight in FIG. 9(*b*) is similarly selected (refer to FIG. 9(*c*)). Moreover, a "cat" that is down and to the right is similarly selected as illustrated in FIG. 9(*d*).

The number of targets for selection is not limited to one. A plurality of different types of targets may be targeted for selection.

It is possible to expect improvements in the attention and/or inhibition of a patient with higher brain dysfunction with the second selection cancellation app. Improvements in attention and/or inhibition are assumed. However, as a result of rehab that was provided by, for example, the present inventors on an actual rehab site, using the second selection cancellation app, contribution to the spatial perception function has also been found.

The number cancellation app, the first selection cancellation app, and the second selection cancellation app are based on the precondition of a use method where a patient looks for, and clears or selects targets one by one, moving his/her face in a seated or standing position without walking. However, the apps may be used in a method where a patient looks for targets while walking.

It may be configured in such a manner that an area where targets and non-targets are placed can be adjusted, according to the severity of the symptom of a patient. For example, a setting may be used in which targets and non-targets are placed only in a narrow area of approximately 60 degrees or, conversely, a wide area of approximately 180 degrees, with the line of sight as the center.

Figure 10:
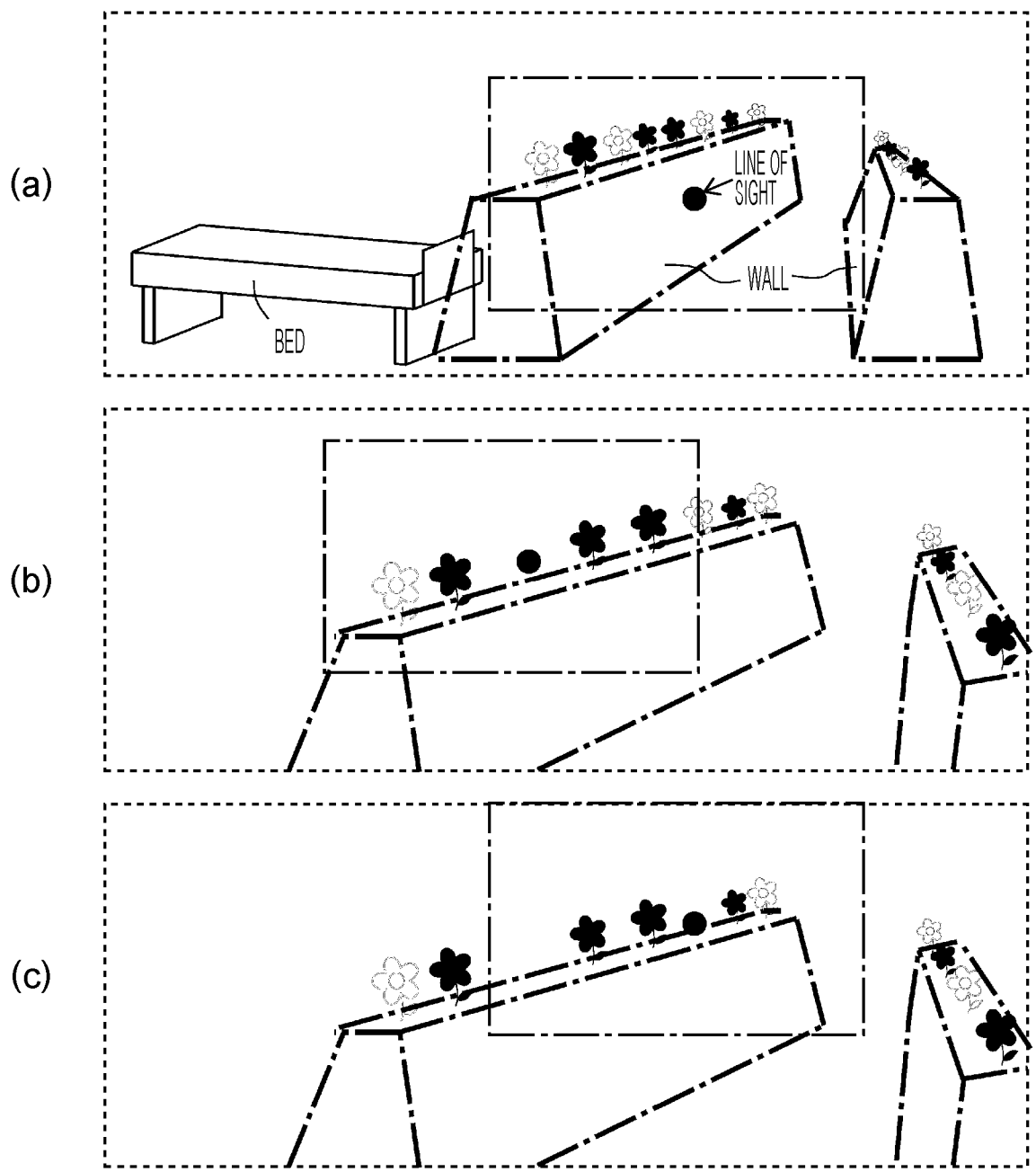
FIGS. 10(a) to 10(c) are diagrams illustrating an operation image in a case where a spatial arrangement app is being executed.

FIGS. 10(a) to 10(c) are diagrams illustrating an operation image in a case where the spatial arrangement app is being executed. In FIGS. 10(a) to 10(c), broken lines indicate the entire space as in FIGS. 7(a) to 7(d). It is assumed here that a bed and a wall are virtually placed in a virtual space in a case of VR. A bed is assumed to exist in a real space in the example of FIGS. 10(a) to 10(c) in cases of AR and MR. It is assumed in the case of AR that a wall image is superimposed on an image of the real space where the bed exists. It is assumed in the case of MR that a virtual-space wall exists in the real space where the bed exists.

In FIGS. 10(a) to 10(c), areas indicated by dot-and-dash lines indicate the area of the field of view within which a patient wearing the image processing apparatus 5 can see as in FIGS. 7(a) to 7(d).

In the case of VR, targets (here, white flowers) and non-targets (here, black flowers) are placed and drawn on the virtual-space wall. In the case of AR, images of the targets and non-targets, together with the wall image, are superimposed on the real-space image. In the case of MR, the targets and the non-targets are placed and drawn on the virtual-space wall.

In the spatial arrangement app, the patient looks for and deletes targets one by one while walking in reality. An image displayed changes in accordance with the current position of the image processing apparatus 5 and the direction of the line of sight.

In the case of MR, the image processing apparatus 5 recognizes the current position and the line of sight in the real space, and generates and displays images of virtual-space objects to be displayed. In the case of MR, the image processing apparatus 5 recognizes an image of the surrounding real space, recognizes the three-dimensional structure of the real space, and then displays images of virtual-space objects (such as the wall and flowers).

In the case of VR, the image processing apparatus 5 recognizes the current position and the line of sight, and generates and displays virtual-space objects to be displayed.

In the case of AR, the image processing apparatus 5 recognizes an image captured by the camera, and superimposes a virtual object on the recognized image. For example, if a virtual wall is superimposed along the pattern of the floor of a room, an image of the virtual wall is generated in such a manner as to match an image of the floor pattern captured by the camera, and a composite image is produced on a frame-by-frame basis. Accordingly, it is possible to provide the user with an image that looks as if the virtual wall is placed on the floor.

In this manner, the image displayed changes moment to moment in response to the movement of the image processing apparatus 5 in all the cases of VR, AR, and MR. Hence, the user can move as if looking for a target image placed on the wall.

In the example of FIG. 10(a), the target (white flower) is visually recognized up and to the left of the line of sight. The patient walks and moves forward a little, and visually recognizes an image where the wall and the flower are approaching gradually, as illustrated in FIG. 10(b). At the point in time when the target can be confirmed, the patient turns his/her eyes to the target, and taps and deletes the target as in the case of the example of FIGS. 7(a) and 7(b). The patient continues deleting the targets similarly. The example of FIG. 10(c) illustrates a state where the patient who has found the white flower to the right turns his/her face to the right and deletes the targets, placing the line of sight on the white flower on the right side.

Walking along a path between two walls is assumed in the examples illustrated in FIGS. 10(a) to 10(c). However, the number of walls may be one, or three or more. Moreover, the wall may not be straight but curved.

It is possible to expect improvements in the spatial perception and/or information acquisition ability of a patient with higher brain dysfunction with the spatial arrangement app. As a result of rehab that was provided by, for example, the present inventors on an actual rehab site, using the spatial arrangement app, relations to the information processing speed and working memory have also been found.

FIGS. 11(a) and 11(b) are diagrams illustrating an operation image in a case where the maze app is being executed. The diagrams illustrated in FIGS. 11(a) and 11(b) are the entire space. In a case of VR, it is assumed here that a door, a desk, a floor, and a wall for a maze are virtually placed in a virtual space. In cases of AR and MR, it is assumed that a door, a desk, and a floor exist in a real space in the examples of FIGS. 11(a) and 11(b). In the case of AR, it is assumed that a wall image is superimposed on an image of the real pace where the door, the desk, and the floor exist. In the case of MR, a virtual-space wall exists in the real space where the door, the desk, and the floor exist.

In FIGS. 11(a) and 11(b), the area of the field of view within which a patient wearing the image processing apparatus 5 can see is not described due to the difficulty of drawing. However, the patient is visually recognizing a fixed area within the entire space through the image processing apparatus 5 as in FIGS. 7(a) to 10(c).

A drawing method of the image processing apparatus 5 of each of the cases of VR, AR, and MR is similar to the case of the spatial arrangement app.

As illustrated in FIG. 11(a), a flag representing a goal is placed in the maze. Moreover, an image representing a target is placed in the maze. When the patient has moved, the image processing apparatus 5 displays an image of a place to which the patient has moved, and gives the patient an impression as if he/she has entered the maze. Such image processing is similar to the case of the spatial arrangement app in FIGS. 10(a) to 10(c).

In addition to FIG. 11(a), the image processing apparatus 5 may display an image as a hint on the image viewed by the patient as illustrated in FIG. 11(b). A location indicated by a star symbol represents the target, which is an image that prompts the patient to go to the goal through the target location. Whether the patient can reach the goal only after passing through the target, or whether the patient can reach the goal without passing through the target is simply a matter that should be designed as appropriate.

The image processing apparatus 5 recognizes whether or not the patient has moved to the target location in response to the movement of the patient. In the cases of VR and MR, positional information can be obtained directly. Accordingly, the image processing apparatus 5 recognizes whether the recognized positional information is the target location or goal location, and counts the score. In the case of AR, an image captured by the camera of the image processing apparatus 5 is recognized. The image processing apparatus 5 judges whether or not the recognized image is an image obtained at the target location or goal location. Accordingly, the score can be counted.

In the maze app, whether or not to simply reach the goal may be set as the scoring criterion. The target may not be used as a problem.

It is possible to expect improvements in the spatial perception and/or executive functioning of a patient with higher brain dysfunction with the maze app.

FIGS. 12(a) and 12(b) are diagrams illustrating an operation image in a case where the square move app is being executed. The diagrams illustrated in FIGS. 12(a) and 12(B) are the entire space. In a case of VR, it is assumed here that a door, a desk, a floor, and a grid of squares for moves are virtually placed in a virtual space. In cases of AR and MR, it is assumed that a door, a desk, and a floor exist in a real space in the examples of FIGS. 12(a) and 12(b). In the case of AR, it is assumed that an image of the grid of squares is superimposed on an image of the real space where the door, the desk, and the floor exist. In the case of MR, it is assumed that the virtual-space grid of squares exist in the real space where the door, the desk, and the floor exist.

In FIGS. 12(a) and 12(b), the area of the field of view within which a patient wearing the image processing apparatus 5 can see is not described due to the difficulty of drawing. However, the patient is visually recognizing a fixed area within the entire space through the image processing apparatus 5 as in FIGS. 7(a) to 10(c).

A drawing method of the image processing apparatus 5 of each of the cases of VR, AR, and MR is similar to the case of the spatial arrangement app.

Firstly, the grid of squares with the indication of north, south, east, and west is displayed by the square move app as illustrated in FIG. 12(a). An instruction "Please stand in the start square "S"." is displayed as the first instruction on a screen viewed by the patient. The patient moves to the location of "S" in accordance with the instruction.

The image processing apparatus 5 recognizes whether or not the patient has moved to a target location in response to the movement of the patient. In the cases of VR and MR, positional information can be obtained directly. Accordingly, the image processing apparatus 5 recognizes whether or not the recognized positional information is the target location (the start location or an instructed location), and counts the score. In the case of AR, an image captured by the camera of the image processing apparatus 5 is recognized. The image processing apparatus 5 judges whether or not the recognized image is an image obtained at the target location. Accordingly, the score can be counted.

When having reached the start location, the image processing apparatus 5 gives an instruction to move some squares as the next instruction. In the example of FIG. 12(b), an instruction to move "three squares west, four squares south, one square east" is given. The image processing apparatus 5 similarly recognizes whether or not to have reached the target location, and counts the score.

At this point in time, it is possible to introduce various game elements by, for example, limiting the time during which one can stand in one square, deducting a point if not on an instructed moving route, and specifying a passing point on the route.

It is possible to expect improvements in the executive functioning and/or memory of a patient with higher brain dysfunction with the square move app.

The scoring criteria of each app do not particularly limit the present invention. In the number cancellation app, the first and second selection cancellation apps, and the spatial arrangement app, for example, a point may be added whenever a target is deleted or selected, a wrong tap leads to deduction of a point, and the score is counted with the time taken to clear as bonus points. In the maze app, a point is added upon arrival at each target location, and the score is counted with the time taken to reach the goal as bonus points. In the square move app, the score is counted with reference to the time required to move to a specified location. These scoring criteria are mere examples, and it is needless to say that another scoring method can be used.

FIG. 13 is a diagram illustrating the data structure of the rehab record information stored in the image processing apparatus 5. As illustrated in FIG. 13, patients are managed on a doctor-in-charge basis. For example, the type of app that was used, the use mode of the app (here, the measurement mode is set at "1" and the training mode at "2"), the year, month, and day of treatment when rehab was performed, the practitioner, the score of the app, the achievement record indicating how a target was achieved (such as the tap time, and correct and incorrect answers), a movement record of the position of the eye point are stored as the rehab record information for each patient in the storage unit 55 of the image processing apparatus 5. A moving image that the patient viewed during rehab may be stored as an option. If the orientation of the patient is used instead of the line of sight, the movement record of the line-of-sight position is a movement record of the orientation of the patient. Therefore, when the movement record is taken conceptually, it can be said that it is information related to the movement of the patient.

It is needless to say that FIG. 13 simply illustrates an example of the data structure of the rehab record information, and does not limit the present invention. The data structure of the rehab record information can be any structure as long as it is data that shows the record of rehab.

FIGS. 14(a) and 14(b) are diagrams illustrating an example of a schedule creation screen used in the schedule creation process (S103) in the doctor-side terminal 2. FIG. 14(a) illustrates before creating a schedule of a patient "Ichiro Tanaka" on Dec. 20, 2018. FIGS. 15(a) to 15(d) are diagrams illustrating the flow of creating the schedule of when the column of December 20 is selected in the state of FIG. 14(a).

Firstly, a screen for selecting a rehab schedule comes up as illustrated in FIG. 15(a). It is configured in such a manner that the date of treatment can be inputted and a rehab menu can be selected. When a pulldown is selected, it becomes possible to select an existing menu created in the past. "Tanaka 1" and "Tanaka 2" are assumed to be the existing menus. The flow of creating a new menu, "Tanaka 3", is illustrated here.

When a "+" button in FIG. 15(a) is selected, a menu edition screen (FIG. 15(b)) comes up. It is configured in such a manner that a new menu name can be inputted (here, "Tanaka 3") on the screen of FIG. 15(b) to select an app to be used. If Select App is selected, an app addition screen illustrated in FIG. 15(c) comes up. There are a test mode tab and a training mode tab. It is configured in such a manner that an app effective for an impaired function can be selected for each mode tab.

Spatial perception, executive functioning, memory, information acquisition ability, attention, and inhibition are used as the impaired functions. An app can be selected for each impairment. Apps effective for the impairments may overlap. In other words, each app is associated with at least one impairment that is expected to be improved by executing the app.

FIG. 15(d) is a screen after the selection of the app. It is illustrated here that the apps of "number cancellation," "first selection cancellation," "second selection cancellation" have been selected for the menu, "Tanaka 3". A Save button is pressed to save the menu, "Tanaka 3", and then add the menu to a menu of December 20 (FIG. 14(b)).

It is needless to say that the flow and screens for creating a schedule menu illustrated in FIGS. 14(a) and 14(b) and FIGS. 15(a) to 15(d) are mere examples, and do not limit the present invention. The present invention includes that those skilled in the art create a schedule menu, using every known method.

Moreover, it may be configured in such a manner that a typical menu can be selected as the rehab menu by default.

FIGS. 16(a) to 16(c) are diagrams illustrating an example of a rehab menu selection screen on the practitioner-side terminal 4. FIG. 16(a) is a basic screen. The basic screen includes buttons of "Start Test (scheduled)," "Start Test (spot)," "Download Rehab Menu," "Send Rehab Result". "Start Test (spot)" is the button used in the second embodiment. Accordingly, a description thereof is omitted here.

Firstly, a practitioner presses "Download Rehab Menu", and executes a schedule downloading process (S302). In the embodiment, the practitioner-side terminal 4 is set in such a manner as to download a rehab menu that is executed on the day of the download. However, it is needless to say that a rehab menu may be downloaded by specifying the date of treatment or by specifying a patient.

FIG. 16(b) is a diagram illustrating an example of a rehab menu download screen. It is configured in such a manner that rehab menus that are performed on this day can be downloaded from the server 3 by pressing a Download button. Rehab menus already downloaded are displayed in "Downloaded Rehab Menus". When one of the menus is selected, the details of the menu are displayed in the field of "Details of Rehab Menu". In this manner, a rehab menu is downloaded first. The practitioner then advances the preparation of rehab.

When rehab is actually started, the practitioner presses "Start Test (scheduled)." A shift is then made to a screen such as illustrated in FIG. 16(c). It is configured in such a manner that a practitioner in charge can be selected and a downloaded menu can be selected as illustrated in FIG. 16(c). It is assumed here that "Tanaka 2" has been selected. Moreover, it is configured in such a manner that the image processing apparatus 5 to be used can be selected in the field of HMD. When the menu is selected in this manner, a shift is made to a screen such as illustrated in FIG. 17(a).

The screen illustrated in FIG. 17(a) illustrates a state where a practitioner, "Goro Tokkyo", performs the menu, "Tanaka 2", using the image processing apparatus 5, "Terminal A". The details of the app are displayed here on the screen as depicted in FIG. 17(a). The display contents are mere examples. However, detailed settings in a case of using the "number cancellation app" are displayed here. The details are assumed to include "Ball (indicating a ball displaying a number) Color", "Number of Balls", "Text Size", "Hint Display Grace (a grace time before a hint is displayed)", "Setting Range (what angle range with the line of sight as the center the numbers are displayed)", "Mode (the measurement mode or training mode)", "Cancellation Method (for example, gesture, gaze, or tap)", and "Time Limit (a time limit to clear)". These items are examples of the app setting conditions.

The measurement mode is a mode of repeatedly setting a predetermined problem to measure the result of rehab. The number of the predetermined problems is not limited to one, and the predetermined problems may be problems of a plurality of patterns. The training mode is a mode for obtaining the result of rehab by setting problems of various patterns. In the first embodiment, problems are assumed to be generated randomly in the training mode.

It is configured in such a manner that the contents of the details of the app setting conditions can be adjusted by pressing an Edit button.

"Previous App" or "Next App" is pressed to sequentially display the details of apps that are scheduled to be executed. It is similarly configured in such a manner that the contents of the details of the app setting conditions of each app can be adjusted.

The edition of the details of the app setting conditions is not necessarily required. If there is no problem with the conditions set by default, it is not necessary to edit the details.

In FIG. 17(a), an "Execute" button is pressed to transmit the rehab menu and the detailed settings from the practitioner-side terminal 4 to the image processing apparatus 5. Rehab is then started.

It is needless to say that the screen example illustrated in FIG. 17(a) is a mere example, and does not limit the present invention.

FIG. 17(b) is a diagram illustrating an example of a screen that is displayed on the practitioner-side terminal 4 during rehab. It is assumed here that the number cancellation app is being executed. An image that the patient is actually viewing is displayed in a field of "Patient's View". The image displayed in the field of "Patient's View" is an image in the virtual space in a case of VR, and is an image where a virtual-space object is superimposed on a real-space image in cases of AR and MR.

As illustrated in FIG. 17(b), the line of sight is indicated by, for example, a black dot. The next target is displayed in such a manner that "No. 1 Next" is displayed. When "Stop" is pressed, the rehab can be stopped on the practitioner side. When "Advise" is pressed, a hint about the next target is displayed on the image processing apparatus 5. For example, an arrow indicating the position of the next target is conceivable as the hint.

When the line of sight is positioned on the target as illustrated in FIG. 18(a), the line of sight changes to, for example, a double circle. When the patient taps on it in this state, the target is deleted as illustrated in FIG. 18(a).

It is needless to say that the examples of the screens on the practitioner-side terminal 4 during rehab, which are illustrated in FIGS. 17(b) to 18(b), are mere examples and do not limit the present invention. Moreover, only the case of the number cancellation app is illustrated here. However, it is sufficient if the other apps are also configured in such a manner as to similarly display an image viewed by the patient on the practitioner-side terminal 4.

It may be configured in such a manner as to simultaneously distribute the images viewed in the line of sight of the patient such as illustrated in FIGS. 17(b) to 18(b) from the practitioner-side terminal 4 to the doctor-side terminal 2 through the network 6 and the server 3. Consequently, it is also possible to grasp the state of rehab on the doctor-side terminal 2 from a distant location in substantially real time.

The image processing apparatus 5 stores rehab record information sequentially during the execution of the app.

When the app is cleared, the image processing apparatus 5 transmits the rehab record information to the practitioner-side terminal 4. After the rehab record information is transmitted to the practitioner-side terminal 4, the practitioner-side terminal 4 displays the results of the execution of the app. FIG. 19 is a diagram illustrating an example of an app execution result screen displayed on the practitioner-side terminal 4.

As illustrated in FIG. 19, the practitioner-side terminal 4 displays the score (here, 47 points), and displays a tap record. The tap record includes a tapped time and required time for one tap, the number of an object (a target or non-target) tapped, and correct/incorrect. An example of the number cancellation app is illustrated here. However, it is simply required to display a tap record suitable for each app on the practitioner-side terminal 4 for each app. Moreover, it is configured in such a manner that the contents of the app settings can be checked (Check Settings) on the practitioner-side terminal 4.

The practitioner-side terminal 4 stores the rehab record information obtained from the image processing apparatus 5. The practitioner then presses "Send Rehab Result" illustrated in FIG. 16(*a*). Accordingly, the rehab record information is transmitted (S306). However, the practitioner-side terminal 4 may transmit the rehab record information to the server 3 automatically without the action of the practitioner. Moreover, in terms of the rehab record information, all information of a plurality of patients may be transmitted together, or information may be transmitted on a patient-by-patient basis.

On the doctor-side terminal 2, the results of rehab can be displayed visually and in an easy-to-understand manner on the basis of the rehab record information downloaded from the server 3. FIGS. 20(*a*) and 20(*b*) are diagrams illustrating an example of the display of the rehab record information on the doctor-side terminal 2. Firstly, it is based on the preconditions that each app is associated with at least one impairment that is expected to be improved by executing the app, and that functional impairment in, for example, spatial perception for which rehab is effective is determined for each app. For example, the number cancellation app is effective for attention. The first selection cancellation app is effective for attention and/or spatial perception. The second selection cancellation app is effective for attention and/or inhibition. The spatial arrangement app is effective for spatial perception and/or information acquisition ability. The maze app is effective for spatial perception and/or an executive functioning. The square move app is effective for memory and/or an executive functioning. The state of each functional impairment can be determined according to the score obtained by the execution of an app.

For example, the score of each functional impairment is graphed as illustrated in FIG. 20(*a*). Accordingly, the doctor can easily grasp the current degree of the functional impairment of the patient. For example, the example illustrated in FIG. 20(*a*) shows at a glance that inhibition and memory are extremely low. A radar chart is presented here. However, in terms of the graph used, every known graph can be used. The type of graph does not limit the present invention.

Moreover, the score of each functional impairment is presented in time line graph form as illustrated in FIG. 20(*b*). Accordingly, the results of rehab of the patient can be checked. It is possible to confirm that the score of each functional impairment is trending higher day by day in the example illustrated in FIG. 20(*b*). Accordingly, it can be said that the rehab is yielding results. A line graph is presented here. However, in terms of the graph used, every known graph can be used. The type of graph does not limit the present invention.

One app is associated with a plurality of impairments that is expected to be improved in some cases. In such cases, the scores of the plurality of impairments are displayed by executing the one app.

Moreover, one impairment is associated with a plurality of apps in some cases. In such cases, the score of the impairment is displayed, using, for example, the average, or weighted average of the scores of the plurality of apps corresponding to the impairment.

Figure 21:
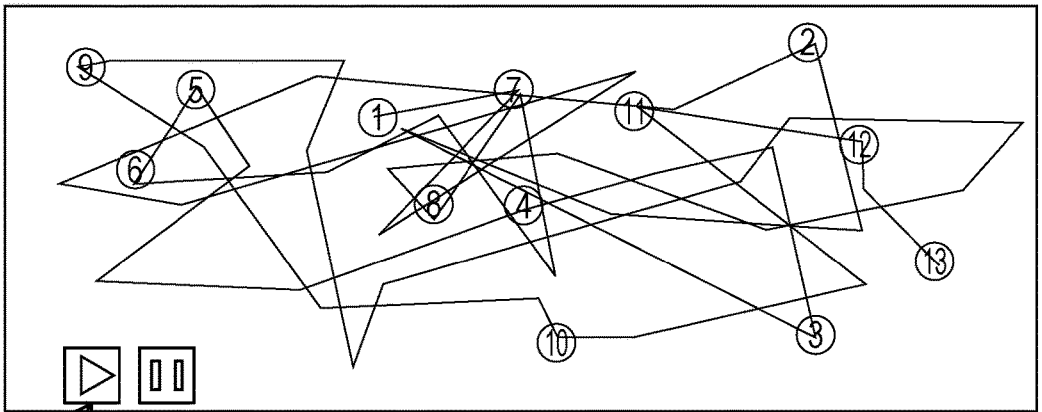
FIGS. 21(a) and 21(b) are diagrams illustrating an example of a display screen in a case of viewing the details of the rehab record information on the doctor-side terminal 2.

FIG. 21(*a*) is a diagram illustrating an example of a display screen in a case where the details of the rehab record information is viewed on the doctor-side terminal 2. It is configured in such a manner that the year, month, and day of treatment, the app that was used, the mode, the practitioner, and the score are displayed as the rehab record information on a patient-by-patient basis on the doctor-side terminal 2. Moreover, it is configured in such a manner that if Details in FIG. 21(*a*) is selected, the state of rehab during the execution of the app can be checked in detail as illustrated in FIG. 21(*b*).

In the example of the screen illustrated in FIG. 21(*b*), the movements of the patient in the case of the number cancellation app are reproduced and displayed. If the doctor checks the record of such movements of the patient, the doctor can diagnose what impairment the patient has. The movements of the patient can also be reproduced sequentially by pressing a Play button as appropriate, which is not necessarily required. Moreover, although not illustrated here, a moving image displayed on the practitioner-side terminal 4 during rehab of the patient may be stored in the server 3, downloaded to the doctor-side terminal 2, and displayed thereon. Moreover, in the example of the screen illustrated in FIG. 21(*b*), a tap record table is also displayed. These detailed displays are simply required to be designed and determined for each app as appropriate. It is needless to say that the examples illustrated here are mere examples, and do not limit the present invention. The display such as FIG. 21(*b*) may be presented on the practitioner-side terminal 4.

Bearing the examples of screen transition described above in mind, the details of the operation of each apparatus are described below with reference to the flowcharts.

Figure 22:
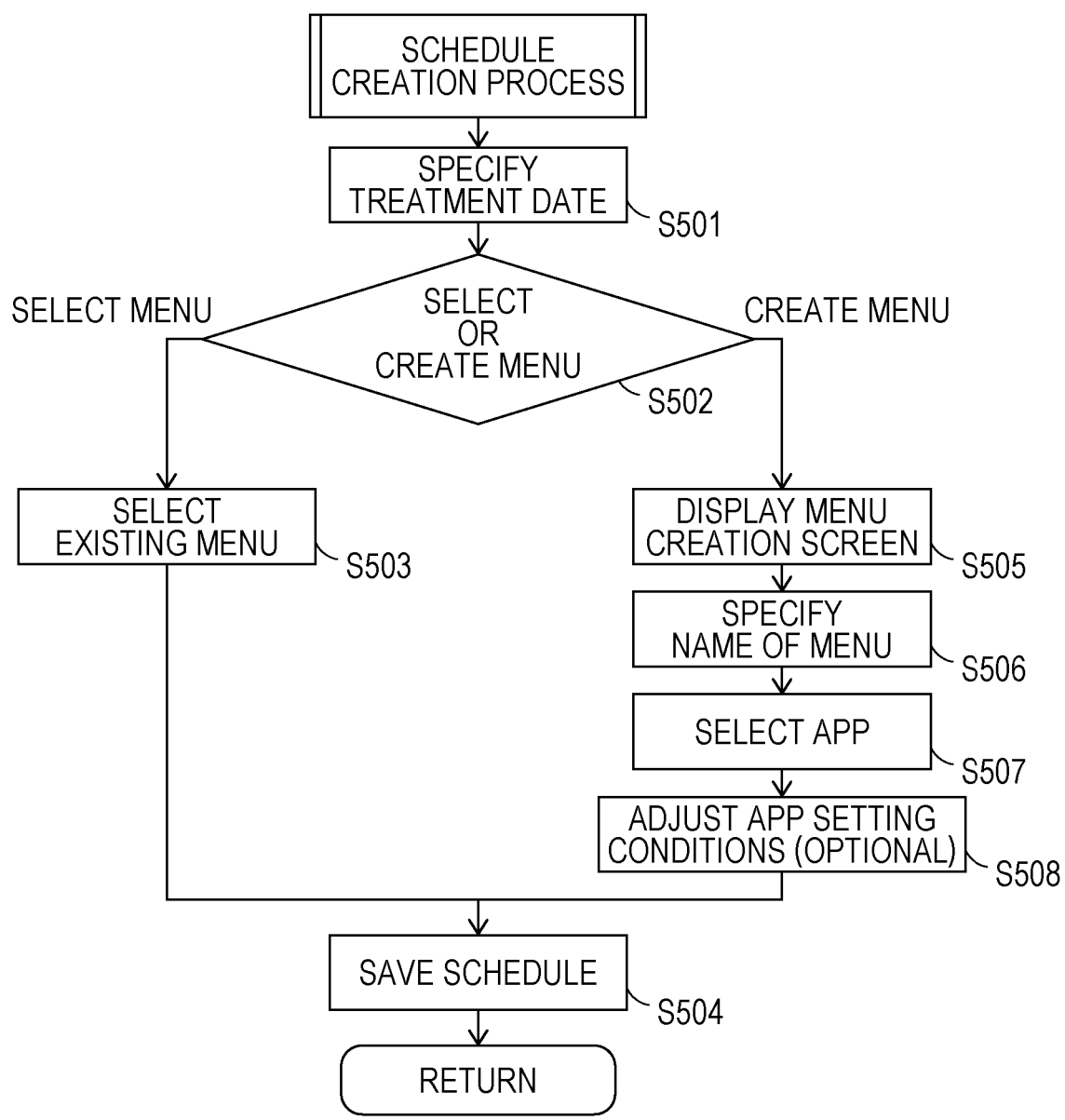
FIG. 22 is a flowchart of the schedule creation process on the doctor-side terminal 2.

FIG. 22 is a flowchart of the schedule creation process on the doctor-side terminal 2. Firstly, as a precondition, it is assumed that the control unit 21 of the doctor-side terminal 2 reads a scheduling-browsing program from the storage unit 25, and executes the program.

The control unit 21 of the doctor-side terminal 2 displays a display for accepting the specification of a treatment date on the display unit 23 to accept the specification of the treatment date from the input unit 22 (S501). In the following description, in order to avoid redundant descriptions, if the relationships between the display unit 23 and the input unit 22, and the control unit 51 are obvious to those skilled in the art, an expression "the control unit 21 accepts the specification of a treatment date." is simply used, and the descriptions of the relationships with the display unit 23 and the input unit 22 are omitted (the same applies to the flowcharts of FIG. 23 and the subsequent figures). Moreover, a case where the control unit 21 saves information in the storage unit 25 is also simply expressed as "the control unit 21 saves information.", and redundant descriptions are avoided (the same applies to the flowcharts of FIG. 23 and the subsequent figures).

Next, the control unit 21 accepts the selection or creation of a menu (S502).

If the selection of a menu is accepted, the control unit 21 allows selecting an existing menu on the basis of rehab menu information (S503), and links the menu to the treatment date, and saves the menu as schedule information (S504).

On the other hand, if the creation of a menu is accepted in S502, the control unit 21 displays a screen for creating a menu on the display unit 23 (S505). Next, the control unit 21 accepts the name of the menu (S506). Next, the control unit 21 lets selecting an app to be used (S507). Next, the control unit 21 lets adjusting the app setting conditions if necessary (S508). The operation of S508 is optional, and is the operation that is performed when the doctor thinks it is necessary. The control unit 21 then saves the created menu as a new menu and as the rehab menu information, and furthermore links the menu to the treatment date and saves the menu as the schedule information (S504).

The control unit 21 uploads the saved rehab menu information and/or schedule information to the server 3 via the communication unit 24 (S104 in FIG. 6).

Figure 23:
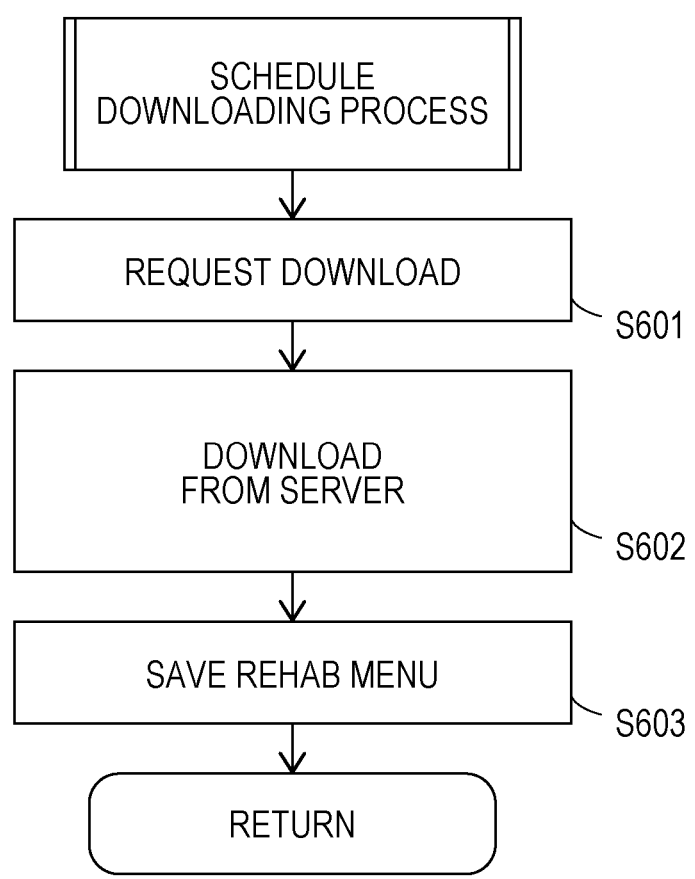
FIG. 23 is a flowchart illustrating a schedule downloading process on the practitioner-side terminal 4.

FIG. 23 is a flowchart illustrating the schedule downloading process on the practitioner-side terminal 4. As a precondition, it is assumed that the control unit 41 of the practitioner-side terminal 4 reads a rehab process program from the storage unit 45 and executes the rehab process program.

The control unit 41 of the practitioner-side terminal 4 requests the server 3 to download rehab menu information and schedule information via the communication unit 44 at the user's instruction (S601). The control unit 41 downloads rehab menu information and schedule information for the day (S602), and saves the information (S603). Only the information for the day is downloaded here. However, it is needless to say that information to be downloaded is not limited to the information for the day, but, for example, information for a plurality of days or for a specified date may be downloaded.

Figure 24:
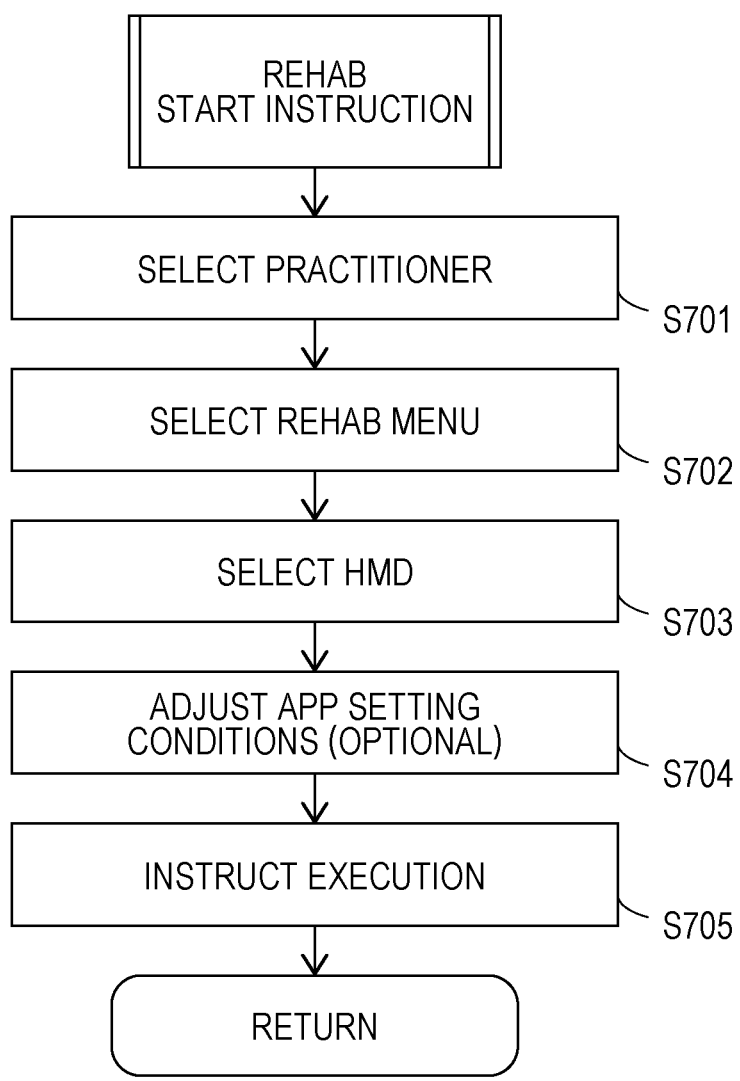
FIG. 24 is a flowchart of a rehab start instruction on the practitioner-side terminal 4.

FIG. 24 is a flowchart of a rehab start instruction on the practitioner-side terminal 4. As a precondition, it is assumed that the control unit 41 of the practitioner-side terminal 4 reads the rehab process program from the storage unit 45, and executes the rehab process program.

The control unit 41 of the practitioner-side terminal 4 lets selecting a practitioner (S701). Next, the control unit 41 lets selecting a rehab menu of a patient who the selected practitioner is in charge of (S702). Next, the control unit 41 lets selecting the image processing apparatus 5 to be used, and starts communicating with the selected image processing apparatus 5 (S703). The control unit 41 accepts adjustments of the app setting conditions as appropriate (S704). After the preparations are finished, the control unit 41 instructs the image processing apparatus 5 to execute an app (S705).

As described above, after being instructed to execute the app, the image processing apparatus 5 executes the instructed app and performs rehab. The operation of the image processing apparatus 5 on each app is described below.

Figure 25:
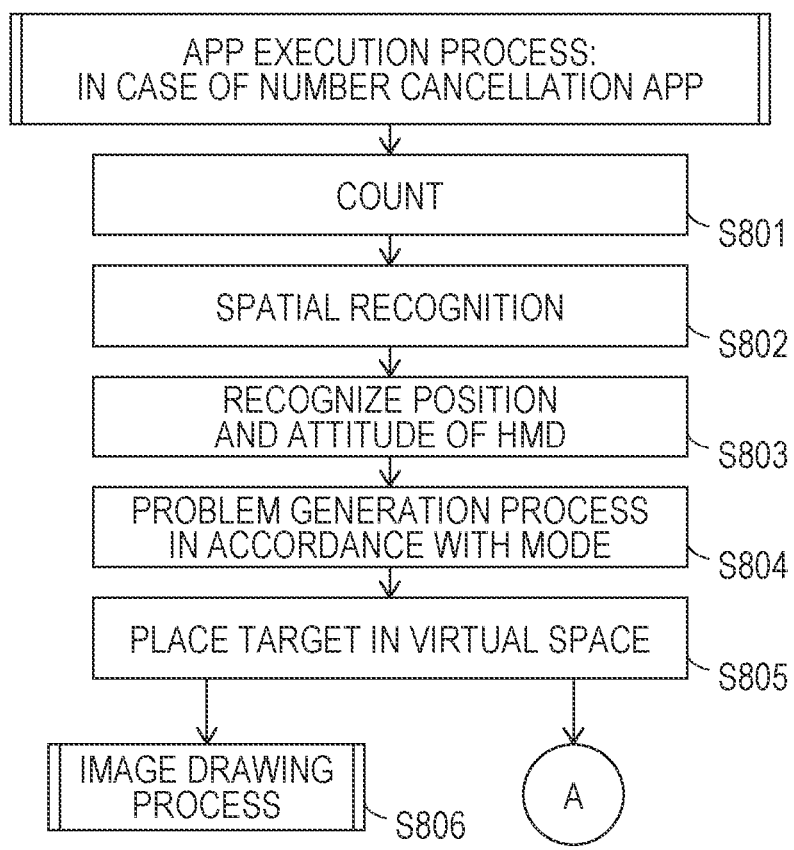
FIG. 25 is a flowchart illustrating the operation of the image processing apparatus 5 during execution of the number cancellation app.

FIG. 25 is a flowchart illustrating the operation of the image processing apparatus 5 during execution of the number cancellation app. As a precondition, it is assumed that the control unit 51 of the image processing apparatus 5 reads in and executes the app execution program, and executes an app instructed by the practitioner-side terminal 4 on instructed setting conditions. Moreover, as a precondition, a case of MR is assumed for the operations illustrated in FIG. 25. However, descriptions of operations in cases of VR and AR are added as appropriate.

In FIG. 25, firstly, the control unit 51 causes the display unit 53 to display a countdown display, and offers a user a time period to turn toward a position where the app is executed (S801). A countdown process is not necessarily required. The position of the image processing apparatus 5 at the time when the app starts being executed may be set as a start position, or the start position may be determined in accordance with input such as the user's tap.

Next, in the case of MR, the spatial recognition unit 57 recognizes a surrounding three-dimensional space, using the built-in camera, and converts the three-dimensional space into three-dimensional data (S802). Next, the tracking unit 58 recognizes the position and inclination of the image processing apparatus 5 (S803). The control unit 51 grasps the position of the image processing apparatus 5 in the three-dimensional space by the processes of S802 and S803, and recognizes where in the three-dimensional space the image processing apparatus 5 is present. A case where an OS of the image processing apparatus 5 performs the process for spatial recognition and the process for tracking are also included in the present invention. Moreover, the spatial recognition process is not limited to image recognition by the built-in camera, but a case where the spatial recognition process is performed, using a depth camera, an infrared sensor, laser irradiation, and other various sensors and detectors is also included in the present invention.

In the case of VR, the control unit 51 generates three-dimensional data of a virtual space in S802, recognizes the position and inclination of the image processing apparatus 5 in S803, and recognizes where in the virtual space the image processing apparatus 5 is located.

In the case of AR, the control unit 51 captures an image of the surroundings in S802 and S803, and determines an area on which a problem is superimposed.

Next, the control unit 51 generates a problem for number cancellation (S804). A problem generation process is described here in detail. The control unit 51 generates a problem on the basis of the app setting conditions. If the mode is the measurement mode, a fixed problem is placed on the three-dimensional data. If the mode is the training mode, a randomly generated problem is placed on the three-dimensional data. The placement area is assumed to be a setting range (the angle with the line of sight as the center) specified by the app setting condition. In addition, the problem is generated on the basis of the app setting conditions of, for example, the color and number of targets, and the size.

The control unit 51 places the generated problem on the three-dimensional data (S805). The execution of the number cancellation app proceeds afterwards. However, a drawing process by the image processing unit 50 is performed in parallel with the execution of the app (S806).

Figure 26:
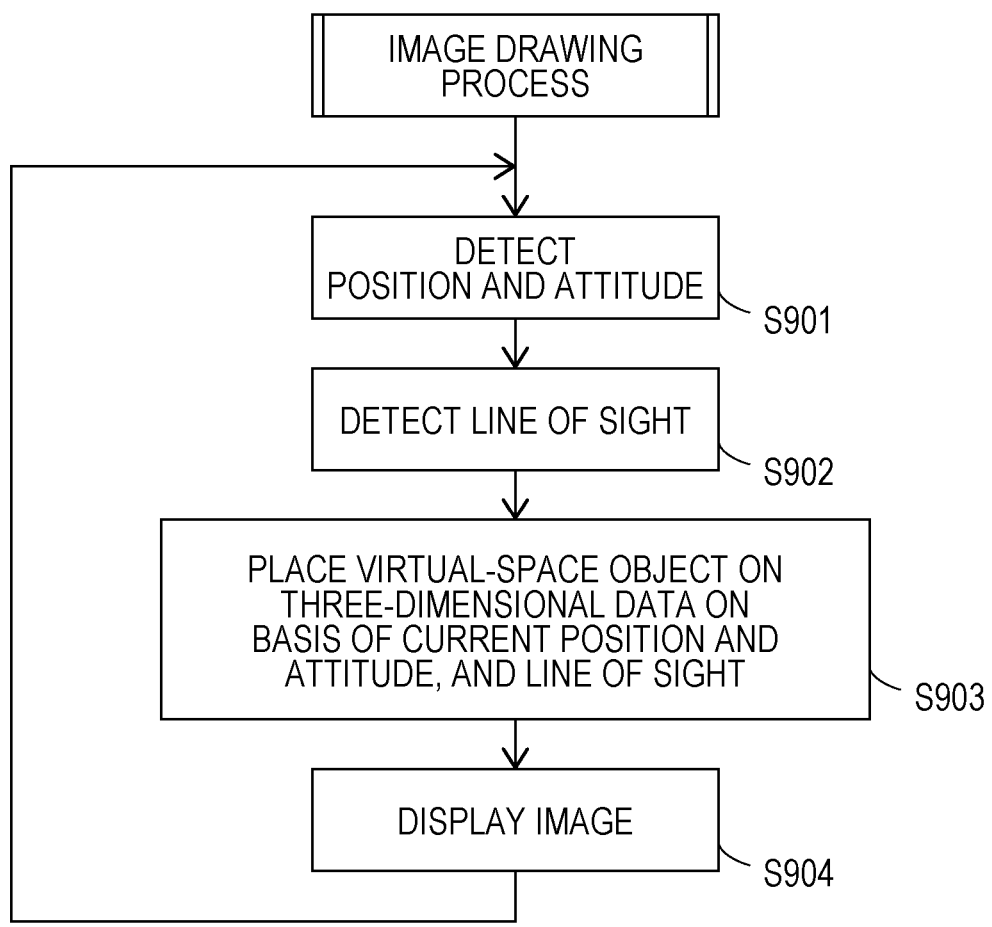
FIG. 26 is a flowchart of an image drawing process in an image processing unit 50.

FIG. 26 is a flowchart of the image drawing process in the image processing unit 50. The image drawing process requires high-speed and a large amount of calculation. Accordingly, it is assumed here that the image processing unit 50 different from the control unit 51 executes the process. Naturally, however, it is needless to say that the control unit 51 can execute the process depending on the performance of the control unit 51.

The image processing unit 50 detects the position and inclination of the image processing apparatus 5 on the three-dimensional data on the basis of the information from the tracking unit 58 (S901). Next, the direction of the line of sight on the three-dimensional data is detected on the basis of the information from the line-of-sight detection unit 59 (S902). Next, the image processing unit 50 places a virtual-space object on the three-dimensional data in accordance with the current position and inclination of the image processing apparatus 5 and the direction of the line of sight (S903), determines an image that is displayed on the display unit 53, and displays the image (S904). Such a process is performed on a frame-by-frame basis. Accordingly, it becomes possible to display a display that looks as if a virtual image exists in the real space on the display unit 53 in response to the movement of the image processing apparatus 5.

The case of VR is similar to the above case of MR, except the point that the image processing unit 50 displays, on the display unit 53, an image where an object is placed on a virtual-space image.

In the case of AR, a real-space image captured by the image processing apparatus 5 is recognized. The image processing unit 50 composites a virtual-space image.

Figure 27:
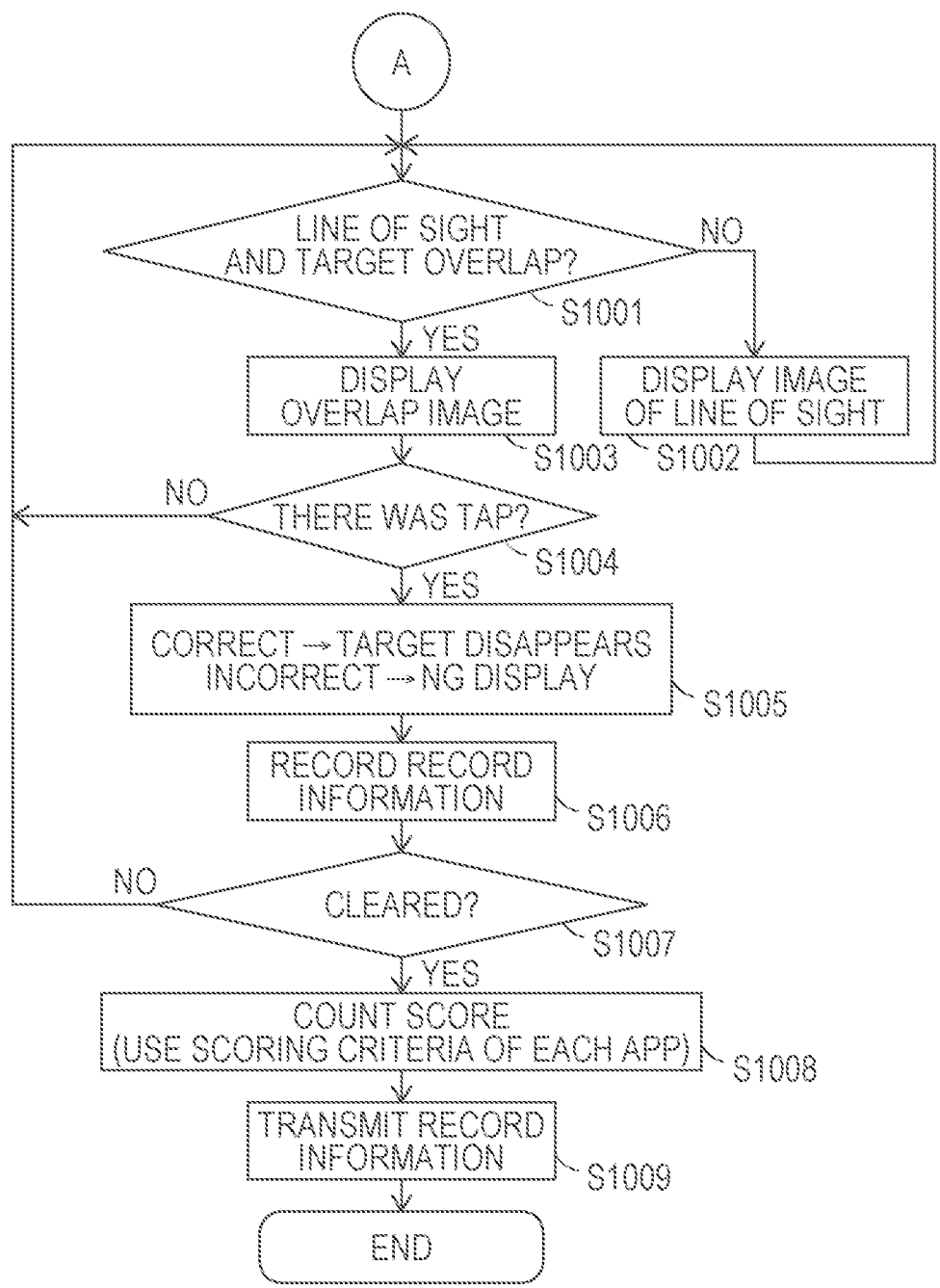
FIG. 27 is a flowchart illustrating the operation continued from FIG. 25.

FIG. 27 is a flowchart illustrating the operation continued from FIG. 25. The control unit 51 judges whether or not the line of sight and the target overlap each other (S1001). If there is not overlap, the control unit 51 continues drawing an image representing the line of sight (S1002). On the other hand, if there is overlap, the control unit 51 changes the display to an image representing the overlap with the image representing the line of sight (S1003).

In the cases of MR and VR, in S1001, the control unit 51 can judge overlap by a comparison between the position of the line of sight and the target position. In the case of AR, the position of the line of sight is not recognized. Accordingly, in S1001 to S1004, the control unit 51 judges, for example, whether or not the finger of the patient is overlapping the target, or whether or not the patient has tapped directly on the display of the tablet terminal 5*e* (for example, the position is specified with a touch of the finger) by use of, for example, image recognition or a touch sensor to judge whether or not there was a tap.

Whether or not there was a tap in the state of S1003 is judged (S1004). If there was not a tap, the control unit 51 returns to the operation of S1001. Therefore, even if proceeding temporarily to the operation of S1003, the control unit 51 proceeds to the operation of S1002 if the overlap is broken halfway through the act of tapping.

If there was a tap, the control unit 51 judges the answer correct or incorrect and, in the case of a correct answer, causes the target to disappear from the three-dimensional data and provides a display representing the disappearance of the target (S1005). In the case of an incorrect answer, the control unit 51 causes the display unit 53 to display a display representing an incorrect answer (S1005).

The control unit 51 stores the rehab record information in the storage unit 55 in response to the tap (S1006). The rehab record information is stored for each cancellation operation.

After the cancellation operation, the control unit 51 judges whether or not all the targets have disappeared and the problem has been cleared (S1007). If the problem has not been cleared, the control unit 51 returns to the operation of S1001. On the other hand, if the problem has been cleared, the control unit 51 counts the score on the basis of predetermined scoring criteria (S1008). The score is stored as rehab record information in the storage unit 55. The control unit 51 then transmits the rehab record information stored in the storage unit 55 to the practitioner-side terminal 4 via the communication unit 54 (S1009). The method for saving rehab record information is not particularly limited. However, the image processing apparatus 5 may, for example, save information such as the position and the line of sight at predetermined time intervals, and transmit the information as rehab record information, together with the score, to the practitioner-side terminal 4. However, the method is not limited to the above. Moreover, the image processing apparatus 5 may transmit rehab record information to the practitioner-side terminal 4 at regular time intervals.

Figure 28:
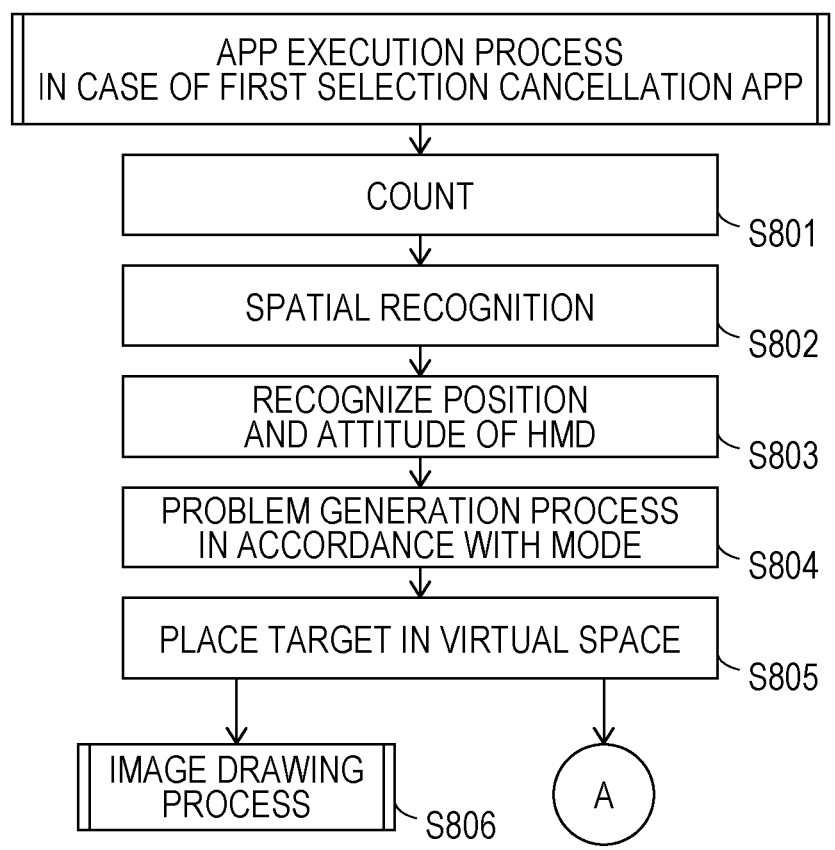
FIG. 28 is a flowchart illustrating the operation of the image processing apparatus 5 that executes the first selection cancellation app.

FIG. 28 is a flowchart illustrating the operation of the image processing apparatus 5 that executes the first selection cancellation app. A precondition here is similar to the case of FIG. 25. Moreover, in FIG. 28, the same reference numerals are assigned to operations similar to the operations in FIG. 25, and only different points are described.

The sequence of cancellation of targets does not matter with the first selection cancellation app unlike the number cancellation app. Therefore, if a target (a correct target) is selected and cancelled in the judgement on correct or incorrect in S1005 in the flowchart of FIG. 27 continued from FIG. 28, it is regarded as correct, and the score is counted irrespective of the sequence of cancellation.

Figure 29:
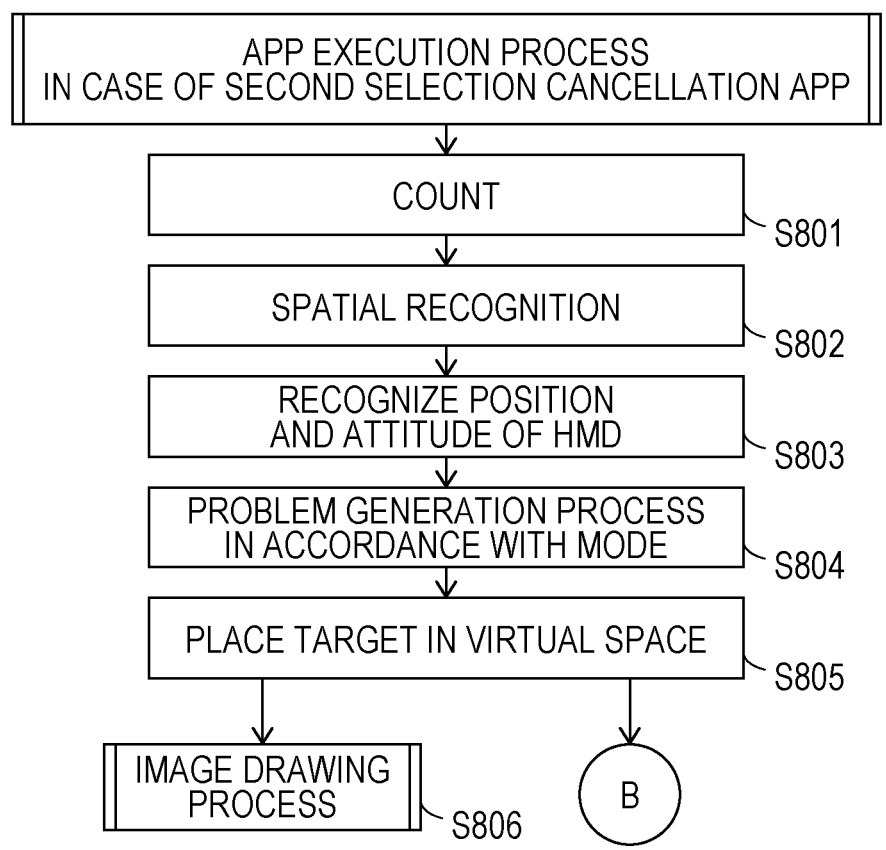
FIG. 29 is a flowchart illustrating the operation of the image processing apparatus 5 that executes the second selection cancellation app.
Figure 30:
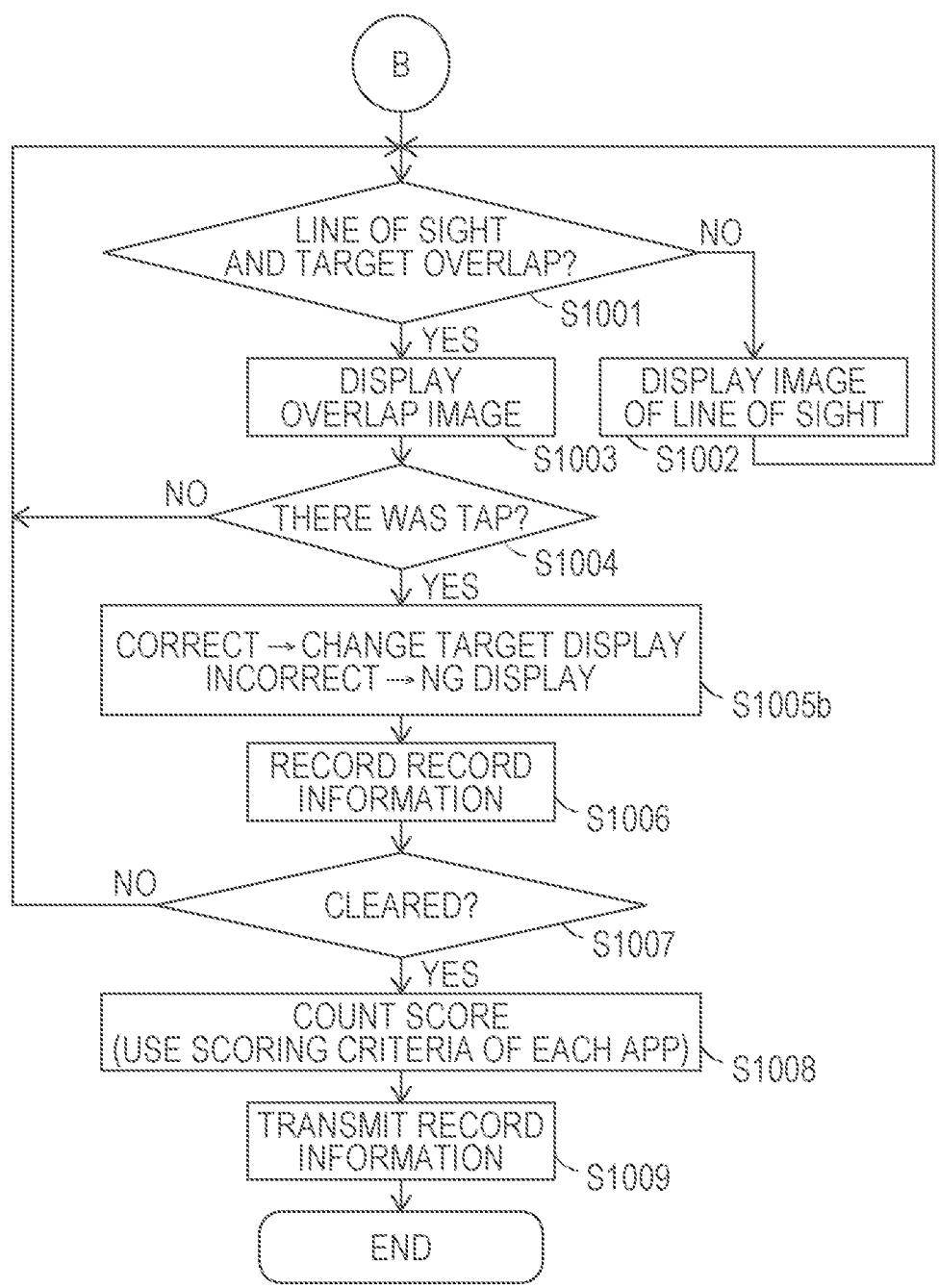
FIG. 30 is a flowchart illustrating the operation continued from FIG. 29.

FIG. 29 is a flowchart illustrating the operation of the image processing apparatus 5 that executes the second selection cancellation app. FIG. 30 is a flowchart illustrating the operation continued from FIG. 29. A precondition here is similar to the case of FIG. 25. Moreover, in FIGS. 29 and 30, the same reference numerals are assigned to operations similar to the operations in FIGS. 25 and 27, and only different points are described.

The sequence of cancellation of targets does not matter with the second selection cancellation app unlike the number cancellation app. If a correct target is selected in the second selection cancellation app, the display of the target is changed, but does not disappear, unlike the first selection cancellation app. Moreover, if a target whose display has been changed is selected in the second selection cancellation app, it is regarded as incorrect. It may be configured in such a manner that the selection of a target other than a correct answer has no influence on the score, or has an influence on the score, regarding the selection as an incorrect answer. However, the configuration is not limited to the above. Therefore, if a target is selected in the judgement on correct or incorrect in S1005*b* in the flowchart of FIG. 30 continued from FIG. 29, the control unit 51 changes the display of the target, which is scored as correct, irrespective of the sequence of cancellation.

Figure 31:
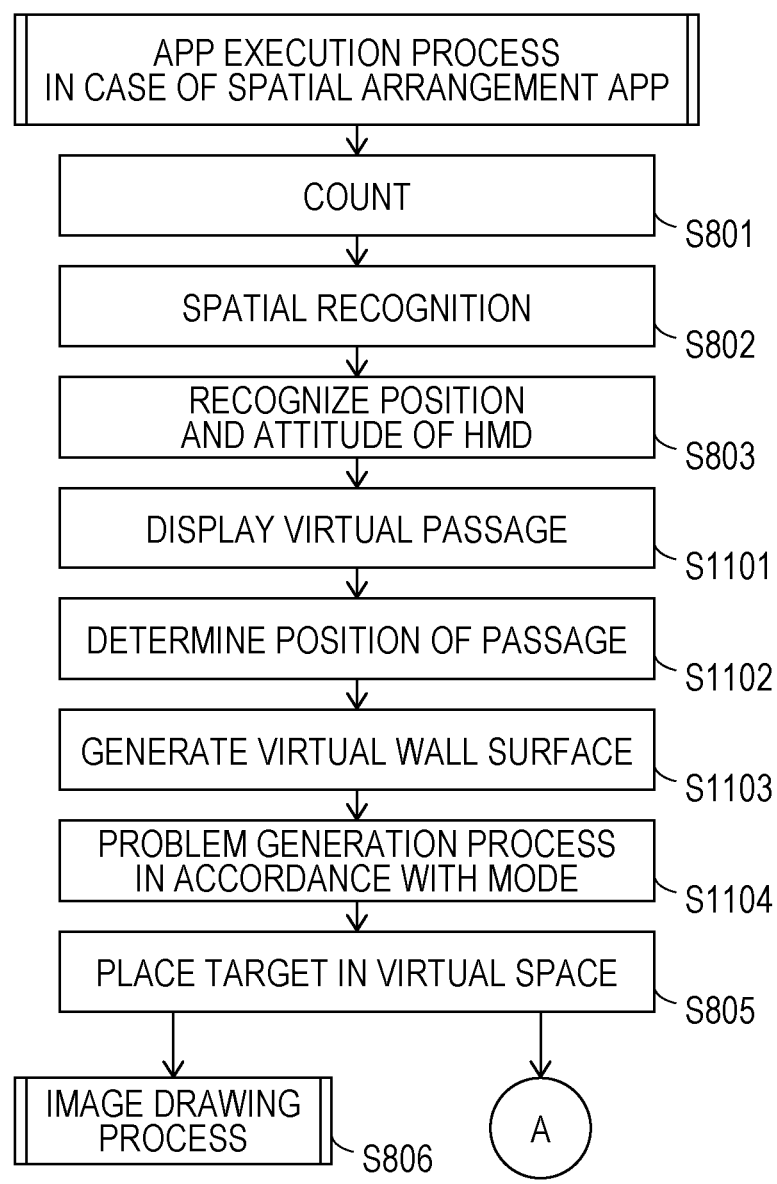
FIG. 31 is a flowchart illustrating the operation of the image processing apparatus 5 that executes the spatial arrangement app.

FIG. 31 is a flowchart illustrating the operation of the image processing apparatus 5 that executes the spatial arrangement app. A precondition here is similar to the case of FIG. 25. Moreover, in FIG. 31, the same reference numerals are assigned to operations similar to the operations in FIG. 25, and descriptions thereof are omitted.

In FIG. 31, the tracking unit 58 recognizes the position and inclination of the image processing apparatus 5 (S803). The control unit 51 then displays a virtual passage on the display unit 53 in accordance with the app setting conditions (S1101). The virtual passage serves as a guide for displaying a virtual wall. It is assumed that the determination of the position of the virtual passage determines the position of the virtual wall. When a patient adjusts the position of the image processing apparatus 5, the position of the virtual passage is also adjusted accordingly. If the virtual passage is placed, overlapping a real-space obstacle, the patient cannot walk in the real space. Accordingly, the patient adjusts the position of the image processing apparatus 5 in such a manner that the virtual passage is displayed in an area where there are no obstacles. When the adjustment of the position of the virtual passage is completed, the patient gives a tap. The control unit 51 determines the position of the virtual passage in response to the tap (S1102). When the position of the virtual passage has been determined, the control unit 51 reflects data representing the virtual passage on the three-dimensional data.

The operations of S1101 to S1102 are similar in all of MR, VR, and AR. In other words, the control unit 51 is simply required to display the virtual passage in such a manner as to overlap the real space in the case of MR, to display the virtual passage in the virtual space in the case of VR, and to superimpose and display the virtual passage on a video of the real space captured in the case of AR.

Next, the control unit 51 generates three-dimensional data of the virtual wall surface along the virtual passage in accordance with the app setting conditions (S1103). The control unit 51 generates a problem that determines the position of a target in such a manner as to place the target on the virtual wall surface in accordance with the app setting conditions (S1104). The control unit 51 determines the position of the target in a fixed manner in the case of the measurement mode, and determines the position of the target randomly in the case of the training mode. The control unit 51 places the generated problem on the three-dimensional data (S805). The image processing unit 50 then executes the operation of FIG. 26 (S806) in parallel with the scoring of the problem.

The scoring of the problem is basically similar to the operation (FIG. 27) of the first selection cancellation app. The sequence of cancellation of targets does not matter in the operation of S1005 unlike the number cancellation app.

Figure 32:
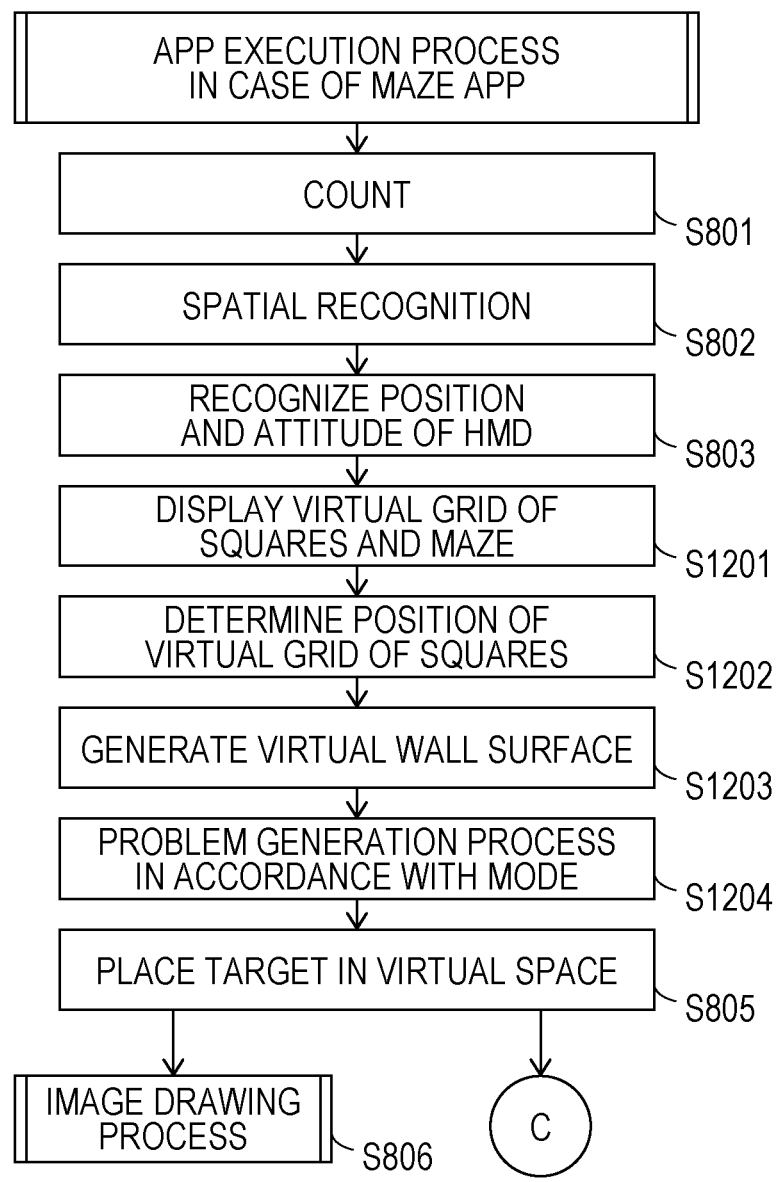
FIG. 32 is a flowchart illustrating the operation of the image processing apparatus 5 that executes the maze app.
Figure 33:
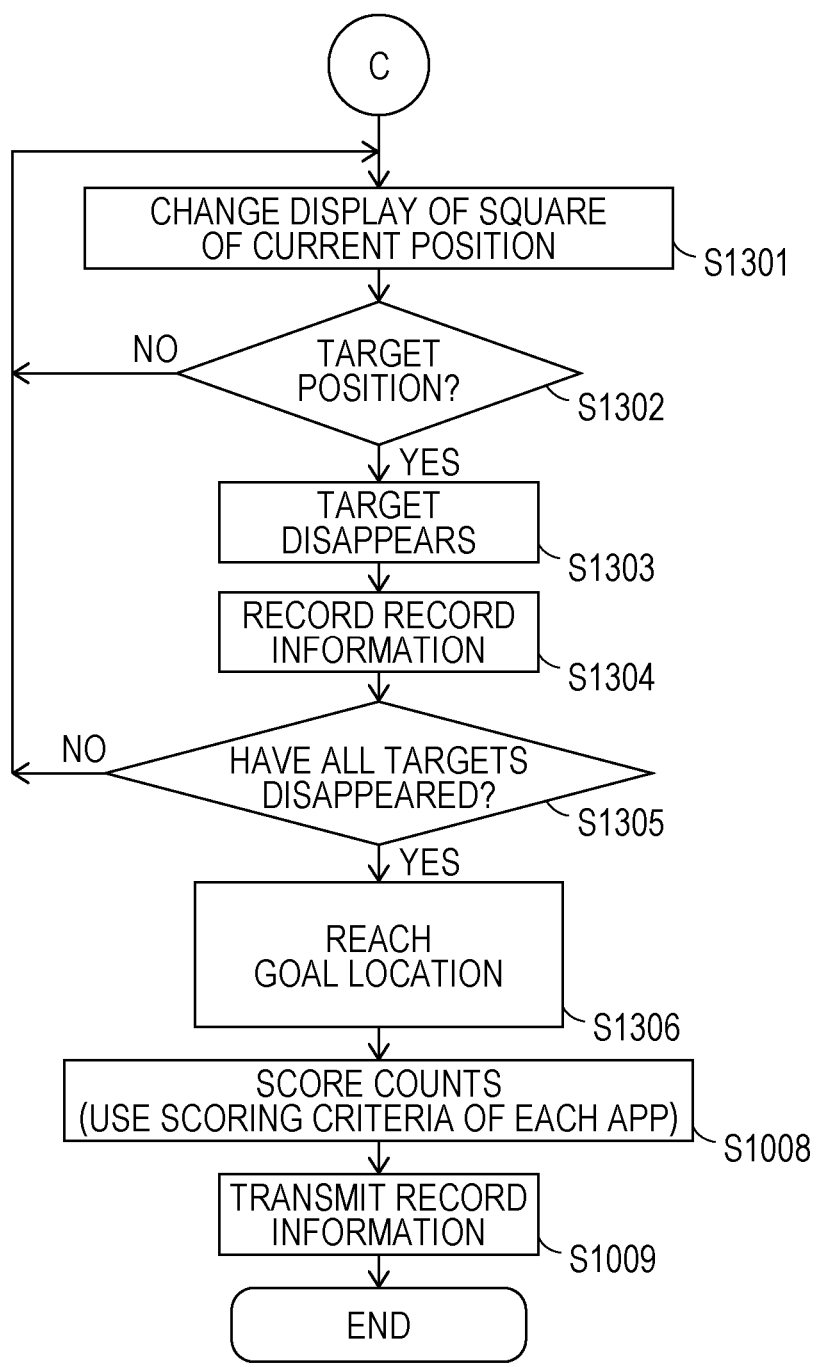
FIG. 33 is a flowchart illustrating the operation continued from FIG. 32.

FIG. 32 is a flowchart illustrating the operation of the image processing apparatus 5 that executes the maze app. FIG. 33 is a flowchart illustrating the operation continued from FIG. 32. A precondition here is similar to the case of FIG. 25. Moreover, in FIGS. 32 and 33, the same reference numerals are assigned to operations similar to the operations in FIGS. 25 and 27, and descriptions thereof are omitted.

In FIG. 32, the tracking unit 58 recognizes the position and inclination of the image processing apparatus 5 (S803). The control unit 51 then displays a virtual grid of squares on the display unit 53, in accordance with the app setting conditions (S1201). The virtual grid of squares serves a guide for displaying a virtual wall for a maze. It is assumed that the determination of the position of the virtual grid of squares determines the position of the virtual wall. When a patient adjusts the position of the image processing apparatus 5, the position of the virtual grid of squares is also adjusted accordingly. If the virtual grid of squares is placed, overlapping a real-space obstacle, the patient cannot walk in the real space. Accordingly, the patient adjusts the position of the image processing apparatus 5 in such a manner that the virtual grid of squares is displayed in an area where there are no obstacles. When the adjustment of the position of the virtual grid of squares is completed, the patient gives a tap. The control unit 51 determines the position of the virtual grid of squares, that is, the position where the maze is placed, in response to the tap (S1202). When the position of the virtual maze has been determined, the control unit 51 reflects data representing the virtual grid of squares on three-dimensional data.

The operations of S1201 to S1202 are similar in all of MR, VR, and AR. In other words, the control unit 51 is simply required to display the virtual grid of squares in such a manner as to overlap the real space in the case of MR, to display the virtual grid of squares in the virtual space in the case of VR, and to superimpose and display the virtual grid of squares on a video of the real space captured in the case of AR.

Next, the control unit 51 generates data of the virtual wall surface for the maze along the virtual grid of squares in accordance with the app setting conditions (S1203). The control unit 51 generates a problem that determines the positions of targets in such a manner as to place the targets on the virtual grid of squares in accordance with the app setting conditions (S1204). The control unit 51 determines the positions of the targets in a fixed manner in the case of the measurement mode, and determines the positions of the targets randomly in the case of the training mode. The control unit 51 places the generated problem on the three-dimensional data (S805). The image processing unit 50 then executes the operation of FIG. 26 (S806) in parallel with the scoring of the problem.

The clearing of the problem is judged along the flow of FIG. 33. The control unit 51 grasps the current position of the image processing apparatus 5 on the basis of the information from the spatial recognition unit 57, and changes the display of a square of the current position (for example, the color of the square is changed) (S1301). Next, the control unit 51 judges whether or not the position of the current square is the position of the target (S1302). If the current position is not the position of the target, the control unit 51 returns to the operation of S1301.

In the cases of MR and VR, in S1302, the control unit 51 can make a judgement on arrival at the position of the target by comparing the current position and the position of the target. In the case of AR, the current position is not recognized. Accordingly, the control unit 51 recognizes an image of the surroundings of the image processing apparatus 5, and judges whether or not to have reached the position of the target in S1301 and S1302.

If the current position is the position of the target, the control unit 51 causes the target to disappear (S1303), and reflects the disappearance on the rehab record information (S1304). Next, the control unit 51 judges whether or not all the targets have disappeared (S1305). If not all the targets have disappeared, the control unit 51 returns to the operation of S1301. If all the targets have disappeared, the control unit 51 continues the process until the current position reaches the goal location and, when the current position has reached the goal location (S1306), proceeds to counting the score (S1008) and transmission of the rehab record information (S1009).

The judgement on whether or not to have reached the goal location is similar to the judgement described in the operation of S1302 in all the cases of MR, VR, and AR.

It is assumed here that it is possible to reach the goal only after all the targets disappear. However, even if not all the targets have disappeared, the control unit 51 may judge the arrival at the goal location as clear and count the score. In this case, the control unit 51 is simply required to, for example, deduct a point due to the fact that the target has not disappeared and reflect the deduction on the score result, which does not limit the present invention.

Figure 34:
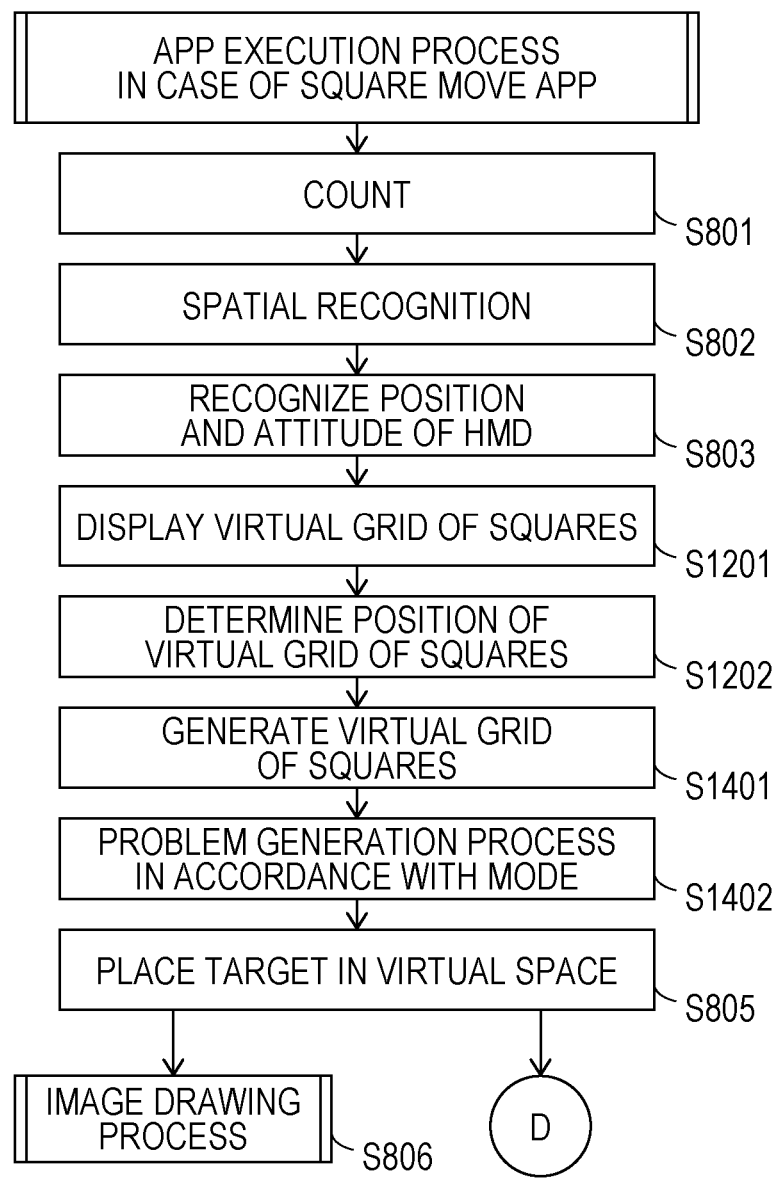
FIG. 34 is a flowchart illustrating the operation of the image processing apparatus 5 that executes the square move app.
Figure 35:
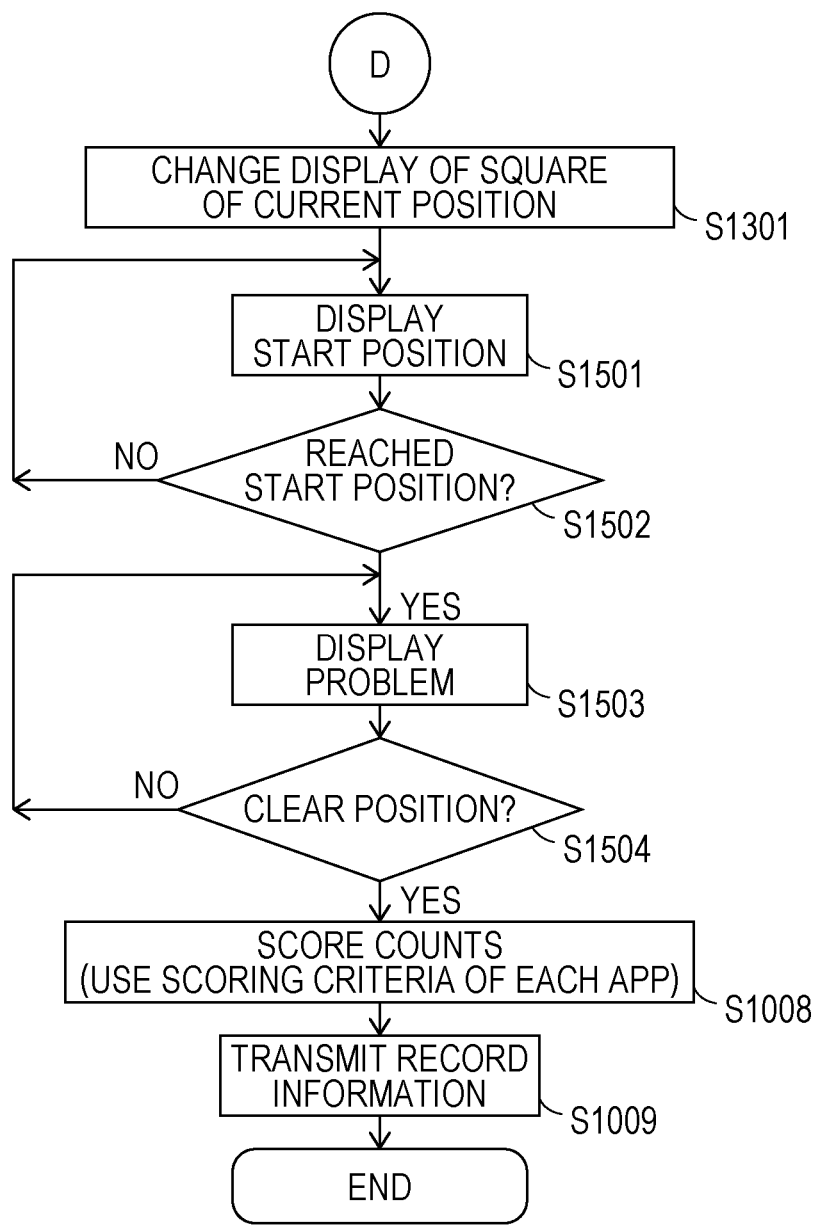
FIG. 35 is a flowchart illustrating the operation continued from FIG. 34.

FIG. 34 is a flowchart illustrating the operation of the image processing apparatus 5 that executes the square move app. FIG. 35 is a flowchart illustrating the operation continued from FIG. 34. A precondition here is similar to the case of FIG. 25. Moreover, in FIGS. 34 and 35, the same reference numerals are assigned to operations similar to the operations in FIGS. 25, 27, 32, and 33, and descriptions thereof are omitted.

FIG. 34 is similar to FIG. 32 up to S1202 where the position of the grid of squares is determined. The control unit 51 then generates data for the virtual grid of squares. The image processing unit 50 reflects the data representing the virtual grid of squares on three-dimensional data (S1401). The control unit 51 generates problems in accordance with the app setting conditions (S1402). The problems generated here are problems presenting a start position and a moving direction. The control unit 51 determines the positions of targets in a fixed manner in the case of the measurement mode, and determines the positions of the targets randomly in the case of the training mode. The control unit 51 proceeds to the operation of the judgement of clearing in FIG. 35 on the basis of the generated problems.

The clearing of the problems is judged along the flow of FIG. 35. The control unit 51 changes the display of a square of the current position (S1301). The control unit 51 displays the start position on a square (S1501). The control unit 51 judges whether or not the current position has reached the start position (S1502). If the current position has reached the start position, the control unit 51 displays the problem (S1503). The control unit 51 judges whether or not to have reached a clear position specified by the problem (S1504). The problem continues being displayed until the current position reaches the clear position. If the current position has reached the clear position, the control unit 51 proceeds to counting the score (S1008) and the transmission of the rehab record information (S1009).

Judgments on arrival at the start position and arrival at the clear position in each of MR, VR, and AR are similar to the judgment on arrival at the target position in FIG. 33.

In this manner, according to the first embodiment, rehab record information is stored in the image processing apparatus 5 that executes rehab with images using virtual reality, augmented reality, or mixed reality, and the rehab record information can be shared between the practitioner-side terminal 4 and the doctor-side terminal 2, which facilitates the doctor and the practitioner grasping the state of rehabilitation of the patient. As a result, it becomes possible to construct an appropriate rehabilitation menu.

Especially a problem that makes a virtual object image used for rehabilitation of higher brain dysfunction appear to exist in a real space is generated, using the image processing apparatus for augmented reality; accordingly, the risk that the patient falls into states such as what is called VR sickness and falling down is reduced. Hence, the patient can undergo rehabilitation safely without feeling strange.

Second Embodiment

The second embodiment illustrates operations in the case of "Start Test (spot)" illustrated in FIG. 16(*a*). It is assumed in the first embodiment that a rehab menu is determined on the basis of a schedule created by the doctor-side terminal 2. However, specific contents of rehab can also be determined by a practitioner under the instruction of a doctor, depending on the legal system of a country where rehab is performed. Moreover, a case is also possible that a doctor instructs a practitioner on rehab principles, not using the rehabilitation system 1 but using another means (for example, verbally, electronic mail, groupware, paper). Hence, the rehabilitation system 1 of the present invention is configured in such a manner as to allow a practitioner to create a rehab menu by himself/herself to offer rehabilitation.

Figures 36, 37:
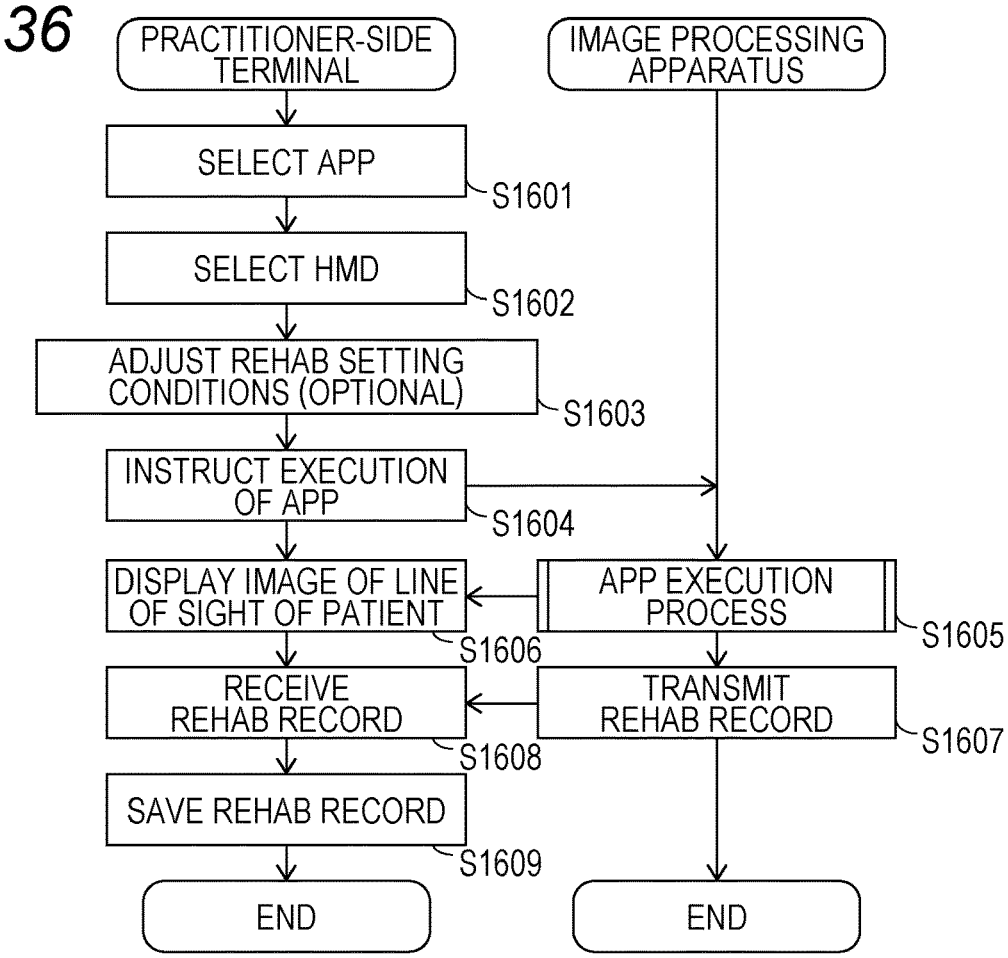
FIG. 36 is a flowchart illustrating the flow of operations between the practitioner-side terminal 4 and the image processing apparatus 5 in a second embodiment.
FIG. 37 is a diagram illustrating an example of an app setting condition settings screen in the number cancellation app on the doctor-side terminal 2 and/or the practitioner-side terminal 4.

FIG. 36 is a flowchart illustrating the flow of operations between the practitioner-side terminal 4 and the image processing apparatus 5 in the second embodiment. Firstly, the practitioner-side terminal 4 selects an app to be used (S1601), and selects the image processing apparatus 5 to be used (S1602). The practitioner-side terminal 4 adjusts the rehab setting conditions at the instruction of a practitioner (S1603). Next, the practitioner-side terminal 4 instructs the image processing apparatus 5 to execute the app at the instruction of the practitioner (S1604).

The image processing apparatus 5 then performs the app execution process as in the first embodiment (S1605). The practitioner-side terminal 4 displays an image of the line of sight of a patient during the execution of the app (S1606). When the execution of the app is completed, the image processing apparatus 5 transmits rehab record information to the practitioner-side terminal 4 (S1607). The practitioner-side terminal 4 receives the rehab record information (S1608), and saves the rehab record information (S1609). The practitioner-side terminal 4 links the rehab record information to the patient, and saves the rehab record information. The practitioner-side terminal 4 can upload the rehab record information to the server 3. The doctor-side terminal 2 can download rehab record information of a spot session from the server 3.

In this manner, a rehab menu can be specified also from the practitioner-side terminal in the second embodiment. Accordingly, the practitioner can perform rehab as circumstances demand.

FIG. 37 is a diagram illustrating an example of an app setting condition settings screen in the number cancellation app on the doctor-side terminal 2 and/or the practitioner-side terminal 4. As illustrated in FIG. 37, for example, the color and number of targets, the text size, the grace time before the display of a hint, the setting range, the mode, the cancellation method, and the time limit can be adjusted in the number cancellation app.

FIG. 38 is a diagram illustrating an example of an app setting condition settings screen in the first selection cancellation app on the doctor-side terminal 2 and/or the practitioner-side terminal 4. As illustrated in FIG. 38, for example, the type and number of correct targets, the type and number of incorrect targets, the setting range, the mode, the cancellation method, and the lime limit can be adjusted in the first selection cancellation app.

FIG. 39 is a diagram illustrating an example of an app setting condition settings screen in the second selection cancellation app on the doctor-side terminal 2 and/or the practitioner-side terminal 4. As illustrated in FIG. 39, for example, the type and number of correct targets, the setting range, the mode, the cancellation method, and the lime limit can be adjusted in the second selection cancellation app.

FIG. 40 is a diagram illustrating an example of an app setting condition settings screen in the spatial arrangement app on the doctor-side terminal 2 and/or the practitioner-side terminal 4. As illustrated in FIG. 40, the wall type, the road length, the road width, the minimum value of the wall height, the maximum value of the wall height, the type and number of correct targets, the type and number of incorrect targets, the mode, the cancellation method, and the time limit can be adjusted in the spatial arrangement app.

FIG. 41 is a diagram illustrating an example of an app setting condition settings screen in the maze app on the doctor-side terminal 2 and/or the practitioner-side terminal 4. As illustrated in FIG. 41, the mode, the number of squares of the maze in breadth, the number of squares in depth, the passage width, the wall height, the type and number of correct targets, and the time limit can be adjusted in the maze app.

FIG. 42 is a diagram illustrating an app setting condition settings screen in the square move app on the doctor-side terminal 2 and/or the practitioner-side terminal 4. As illustrated in FIG. 42, the number of squares in breadth, the number of squares in depth, the number of moves (how many moves to reach a target location), the number of times of repetition (how many times in total a problem is set), the stop allowed time (the time period during which a stop is allowed in one square), the mode, and the time limit can be adjusted in the square move app.

The app setting conditions illustrated above are mere examples, can be changed in any way, and do not limit the present invention.

Other Embodiments

The app execution program that is executed in the image processing apparatus 5 may be configured in such a manner as to display a virtual trainer. FIG. 43 is an example of the virtual trainer that is displayed on the image processing apparatus 5.

The image processing apparatus 5 displays an avatar image of the virtual trainer on the display unit 53. The virtual trainer outputs words of encouragement and hint words in text form or by voice.

The use of the virtual trainer allows reducing the burdens on the practitioner.

Figure 44:
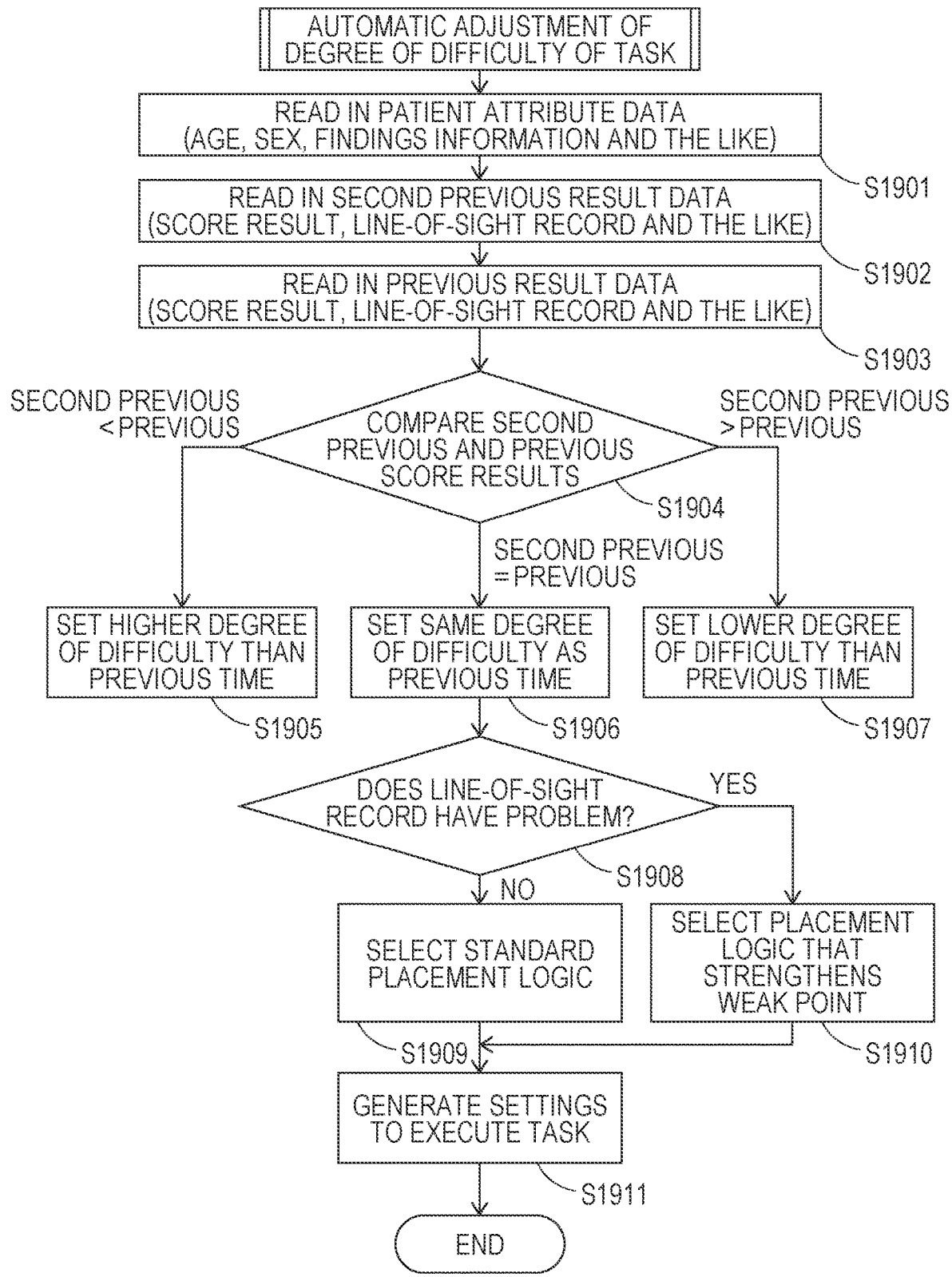
FIG. 44 is a flowchart illustrating operations of the doctor-side terminal 2 and/or the practitioner-side terminal 4 of when it is configured in such a manner that the degree of difficulty of a problem can be adjusted automatically.

Moreover, it is better if the degree of difficulty of a problem can be adjusted automatically. FIG. 44 is a flowchart illustrating operations of the doctor-side terminal 2 and/or the practitioner-side terminal 4 of when it is configured in such a manner that the degree of difficulty of a problem can be adjusted automatically. It is assumed below that the practitioner-side terminal 4 sets the degree of difficulty and creates a problem according to the weak point for the purpose of simplification of explanation, but the doctor-side terminal 2 may do so. Moreover, if at-home rehab is assumed, it is also conceivable that a patient undergoes rehab, for example, at home with the image processing apparatus 5c or 5e such as a smartphone or tablet terminal. In such a case, the virtual trainer is useful. Moreover, in the case of at-home rehab, the image processing apparatus 5, or the server 3, may adjust the degree of difficulty automatically and create a problem according to the weak point as illustrated in FIG. 44. In other words, which device adjusts the degree of difficulty does not limit the present invention.

The practitioner-side terminal 4 reads in patient attribute data (S1901), reads in the second previous result data of a relevant patient (S1902), and reads in the previous result data (S1903). The practitioner-side terminal 4 then compares the previous result data and the second previous result data, and judges whether or not the grade is getting higher (S1904).

If the previous grade is higher than the second previous grade, the practitioner-side terminal 4 sets a higher degree of difficulty than the previous time (S1905). If the previous grade and the second previous grade are the same, the practitioner-side terminal 4 sets the same degree of difficulty as the previous time (S1906). If the previous grade is lower than the second previous grade, the practitioner-side terminal 4 sets a lower degree of difficulty than the previous time (S1907). The degree of difficulty can be set on the basis of, for example, the number of targets and the placement area. However, the setting of the degree of difficulty is a mere example, and does not limit the present invention.

After setting the degree of difficulty, the practitioner-side terminal 4 judges whether or not a line-of-sight record has a problem (S1908). Having a problem with the line-of-sight record here indicates, for example, whether or not there are many incorrect answers in the selection and cancellation of targets on the right side. The operation of S1906 may be judged automatically by the practitioner-side terminal 4, or may be judged manually by a practitioner or doctor.

If the line-of-sight record has no problem, the practitioner-side terminal 4 selects a standard placement logic (S1909). On the other hand, if the line-of-sight record has a problem, the practitioner-side terminal 4 selects a placement logic that strengthens the weak point (S1910). For example, a logic that places targets randomly is conceivable as the standard placement logic. If the weak point is, for example, the right side, for example, a logic that places more targets on the right side is conceivable as the logic that strengthens the weak point. However, the logics are examples, and do not limit the present invention.

After the degree of difficulty and the placement logic are set in this manner, the practitioner-side terminal 4 instructs the image processing apparatus 5 to generate a problem, considering the degree of difficulty and the placement logic upon problem generation (S1911). The image processing apparatus 5 generates a problem on the basis of the degree of difficulty and the placement logic.

The previous and second previous scores are compared to adjust the degree of difficulty. However, comparison targets are not limited to the previous and second previous scores. The average of the previous score and an Nth previous score, or an upward/downward trend of the average of an Nth previous score is also acceptable. In any case, it is simply required to adjust the degree of difficulty on the basis of the past score.

Only the degree of difficulty may be adjusted, or only the placement logic based on the grasping of a weak point may be adjusted.

The adjustments of the degree of difficulty and/or the placement logic are realized in this manner. Accordingly, it becomes possible to further increase the effect of rehab for a patient.

The size of a target image may be changeable. The size of a target image may change in the same problem, or may change according to the degree of difficulty of a problem.

Moreover, for example, the color and brightness of a target image may be changeable. For example, the color and brightness of a target image may change in the same problem, or may change according to the degree of difficulty of a problem.

These adjustments may be set manually by a person, or may be made automatically in accordance with rehab record information.

Moreover, a target is not only stationary but also may be moving in a problem. The move of the target allows expecting a further improvement in impairment.

Up to this point the present invention has been described in detail. However, the above-mentioned descriptions are simply the exemplification of the present invention in every respect, and are not intended to limit the scope of the present invention. It is needless to say that various improvements and modifications can be made without departing from the scope of the present invention. Each of the constituent elements of the invention disclosed in the description shall be established as a single independent embodiment. An embodiment obtained by combining the constituent elements in every combination method shall be included in the present invention.

INDUSTRIAL APPLICABILITY

The present invention relates to a rehabilitation system and an image processing apparatus, and is industrially applicable.

LIST OF REFERENCE NUMERALS

1 Rehabilitation system
2 Doctor-side terminal

3 Server
4 Practitioner-side terminal
5 Image processing apparatus
6 Network
50 Image processing unit
51 Control unit
52 Input unit
53 Display unit
54 Communication unit
55 Storage unit
56 Audio output unit
57 Spatial recognition unit
58 Tracking unit
59 Line-of-sight detection unit (orientation detection unit)

The invention claimed is:

1. An image processing apparatus, which is wearable by a user, for rehabilitation of higher brain dysfunction, comprising:
a recording medium that stores at least one app for presenting the user wearing the image processing apparatus a problem for the rehabilitation of higher brain dysfunction;
a wired or wireless switch or a touchscreen;
a camera;
a spatial recognition unit configured to process a data obtained by the camera, an infrared sensor or a laser irradiation to recognize a three-dimensional shape of a surrounding space of the image processing apparatus, and convert the three-dimensional shape of the space into three-dimensional data;
a first sensor structurally included in a housing of the image processing apparatus or attached to an outside of the housing, and configured to detect a position and an inclination of the image processing apparatus in the space recognized by the spatial recognition unit;
a second sensor configured to detect an orientation of the user including a line of sight of the user;
an image processor configured to store, in the storage unit, the three-dimensional data of the space, three-dimensional data of a virtual object, three-dimensional data of the position and inclination of the image processing apparatus detected by the first sensor, and three-dimensional data of the orientation of the user detected by the second sensor with the same coordinate axes, place the virtual object in the space recognized by the spatial recognition unit on the same coordinate axes, and generate an image of the virtual object visible to the user on the basis of the position and inclination of the image processing apparatus detected by the first sensor and the orientation of the user detected by the second sensor; and
a mixed reality-specific display unit configured to visually present the image of the virtual object generated by the image processor for the user as if the image generated by the image processor exists in a real space, wherein
the image processing apparatus further comprises a processor configured to generate the problem as if the image of the virtual object used for rehabilitation of higher brain dysfunction exists in the real space,
the image processing apparatus performs the rehabilitation of higher brain dysfunction by executing the at least one app using a mixed reality while the image processor performs a drawing process,
the drawing process includes:
detecting the position and the inclination of the image processing apparatus on the three-dimensional data of the space on the basis of information from the first sensor;
detecting the orientation of the user on the three-dimensional data of the space on the basis of information from the second sensor;
placing the three-dimensional data of the virtual object on the three-dimensional data of the space in accordance with the current position and inclination of the image processing apparatus and the orientation of the user; and
visually presenting the generated image of the virtual object on the mixed reality-specific display unit,
the at least one app sets the problem eliminating or changing the image of the virtual object in accordance with an input from the user, and
the input from the user includes at least one of an input from the wired or wireless switch or the touchscreen, a gesture of the user detected by the camera, or the line of sight of the user at a fixed point for a fixed period of time, which is detected by the second sensor.

2. The image processing apparatus according to claim 1, wherein the processor detects the user's selection of the image of the virtual object, using the detection result by the second sensor, and scores the problem on the basis of the detected selection result.

3. The image processing apparatus according to claim 2, wherein the processor uses an image to be selected by the user as the image of the virtual object, and generates the problem in such a manner as to place the image at least in the field of view of the user.

4. The image processing apparatus according to claim 3, wherein the processor generates the problem in such a manner as to place the image to be selected by the user also outside the field of view of the user.

5. The image processing apparatus according to claim 1, wherein the processor scores the problem on the basis of the detection result of the position of the image processing apparatus by the first sensor.

6. The image processing apparatus according to claim 5, wherein the processor uses an image for prompting the user to move in the real space as the image of the virtual object, and generates the problem in such a manner as to place the image at least in the field of view of the user.

7. The image processing apparatus according to claim 6, wherein the processor generates the problem in such a manner as to place the image for prompting the user to move in the real space also outside the field of view of the user.

8. The image processing apparatus according to claim 1, wherein
the processor includes a measurement mode and a training mode as a mode to execute the app for presenting a patient the problem,
in the measurement mode, the processor sets a predetermined problem, and
in the training mode, the processor sets a randomly created problem.

9. The image processing apparatus according to claim 1, wherein the image processing apparatus displays an image of an avatar being a virtual trainer upon executing the app for presenting a patient the problem.

10. The image processing apparatus according to claim 1, wherein the image processing apparatus adjusts the degree of difficulty on the basis of a past score of the problem, and sets the problem according to the degree of difficulty.

11. The image processing apparatus according to claim 1, wherein the image processing apparatus sets the problem according to a weak point of a patient on the basis of the rehab record information.

12. A rehabilitation system for performing rehabilitation of higher brain dysfunction, the rehabilitation system comprising:
the image processing apparatus according to claim 1, the image processing apparatus being configured to execute an app for presenting the user as a patient the problem for rehab based on the image using mixed reality and store the patient's problem solution record as rehab record information;
a practitioner-side terminal configured to receive the rehab record information from the image processing apparatus;
a server configured to save the rehab record information transmitted from the practitioner-side terminal; and
a doctor-side terminal configured to receive the rehab record information from the server and display the state of rehabilitation performed for the patient on the basis of the rehab record information.

13. The rehabilitation system according to claim 12, wherein
the practitioner-side terminal is capable of selecting the app to be implemented on the image processing apparatus, and instructing the image processing apparatus to execute the selected app.

14. The rehabilitation system according to claim 12, wherein
the doctor-side terminal creates a schedule of rehab to be performed on the image processing apparatus in such a manner as to link the schedule to the app to be used, and saves the schedule in the server, and
the practitioner-side terminal is capable of downloading the schedule saved in the server, and instructing the image processing apparatus to execute the app specified by the schedule.

15. The rehabilitation system according to claim 12, wherein
the app to be used on the image processing apparatus is associated with at least one impairment that is expected to be improved by the implementation of the app,
the rehab record information includes the score of an answer to the problem set by the app, and
the doctor-side terminal displays the score of the app for each impairment to provide the display in such a manner as to allow comprehending an impairment improvement state.

16. The rehabilitation system according to claim 15, wherein the doctor-side terminal displays app score results on a time-series basis.

17. The rehabilitation system according to claim 12, wherein
the rehab record information includes information related to the movement of the patient, and
at least one of the doctor-side terminal and the practitioner-side terminal is capable of providing a display that reproduces the movement of the patient on the basis of the rehab record information.

18. The rehabilitation system according to claim 12, wherein
the image processing apparatus transmits, to the practitioner-side terminal, an image that is visible to the patient during the execution of the app, and
the practitioner-side terminal displays the image transmitted from the image processing apparatus.

19. The rehabilitation system according to claim 18, wherein the image displayed on the practitioner-side terminal is saved as a moving image.

20. The rehabilitation system according to claim 19, wherein the doctor-side terminal is capable of playing the saved moving image.

21. The rehabilitation system according to claim 18, wherein the image transmitted from the image processing apparatus is distributed simultaneously to the doctor-side terminal.

22. The rehabilitation system according to claim 12, wherein
the app to be executed on the image processing apparatus includes an adjustable setting condition, and
at least one of the doctor-side terminal and the practitioner-side terminal is capable of adjusting the setting condition.

23. The rehabilitation system according to claim 22, wherein the range of an angle to display the problem is adjustable as the setting condition.

24. The rehabilitation system according to claim 22, wherein the number of objects to be displayed in the problem is adjustable as the setting condition.

25. The rehabilitation system according to claim 12, wherein
the image processing apparatus includes a measurement mode and a training mode as a mode to execute the app,
in the measurement mode, the image processing apparatus sets a predetermined problem, and
in the training mode, the image processing apparatus sets a randomly created problem.

26. The rehabilitation system according to claim 12, wherein the image processing apparatus displays an image of an avatar being a virtual trainer.

27. The rehabilitation system according to claim 12, wherein the doctor-side terminal, the practitioner-side terminal, the image processing apparatus, or the server adjusts the degree of difficulty of the problem on the basis of a past score of the problem, and causes the image processing apparatus to set the problem according to the degree of difficulty.

28. The rehabilitation system according to claim 12, wherein the doctor-side terminal, the practitioner-side terminal, the image processing apparatus, or the server creates the problem in accordance with a weak point of the patient based on the rehab record information, according to the weak point, and causes the image processing apparatus to set the problem.

29. The rehabilitation system according to claim 12, wherein the image processing apparatus executes a number cancellation app that displays images of numbers, using the mixed reality, and sets the problem that prompts cancelling the images of the numbers sequentially.

30. The rehabilitation system according to claim 12, wherein the image processing apparatus executes a first selection cancellation app that displays images of a target and a non-target, using the mixed reality, and sets the problem that prompts cancelling the image of the target.

31. The rehabilitation system according to claim 12, wherein the image processing apparatus executes a second selection cancellation app that displays images of a target and a non-target, using the mixed reality, and sets the problem that prompts selecting the image of the target and changing the image after the selection.

32. The rehabilitation system according to claim 12, wherein the image processing apparatus executes a spatial arrangement app that displays at least one image of a wall, and images of a target and a non-target placed on the wall, using the mixed reality, and sets the problem that prompts cancelling the image of the target.

33. The rehabilitation system according to claim 12, wherein the image processing apparatus executes a maze app that displays an image of a maze, using the mixed reality, and sets the problem that prompts clearing the maze.

34. The rehabilitation system according to claim 33, wherein in the maze app, a target image is displayed to set the problem that prompts cancelling the target image.

35. The rehabilitation system according to claim 12, wherein the image processing apparatus executes a square move app that displays an image of a grid of squares, using the mixed reality, and sets the problem that prompts moving over the grid of squares.

36. The rehabilitation system according to claim 12, wherein the image processing apparatus displays a virtual image also outside the field of view of the patient in the app that displays the virtual image using the mixed reality.

37. The rehabilitation system according to claim 36, wherein the virtual image is at least one of the images of the target and the non-target of the problem.

38. The rehabilitation system according to claim 36, wherein the virtual image is the image of the wall, maze, or grid of squares used in the problem.

39. A non-transitory computer-readable storage medium in which a computer program for rehabilitation of higher brain dysfunction is stored, the computer program including at least one app for presenting a user wearing an image processing apparatus a problem for the rehabilitation of higher brain dysfunction,
wherein the computer program, when executed by a processor in the image processing apparatus, causes the processor to perform:
processing a data obtained by a camera, an infrared sensor or a laser irradiation to recognize a three-dimensional shape of a surrounding space of the image processing apparatus, and converting the three-dimensional shape of the space into three-dimensional data;
detecting, on the basis of information from a first sensor structurally included in a housing of the image processing apparatus or attached to an outside of the housing, position and an inclination of the image processing apparatus in the space recognized;
detecting, on the basis of information from a second sensor in the image processing apparatus, an orientation of the user including a line of sight of the user;
storing, in a storage unit of the image processing apparatus, the three-dimensional data of the space, three-dimensional data of a virtual object, three-dimensional data of the detected position and inclination of the image processing apparatus, and three-dimensional data of the detected orientation of the user with the same coordinate axes, placing the virtual object in the recognized space on the same coordinate axes, and generating an image of the virtual object visible to the user on the basis of the detected position and inclination of the image processing apparatus and the detected orientation of the user; and
visually presenting the image of the generated virtual object for the user as if the image of the generated virtual object exists in a real space,
the computer program causes the processor to generate the problem as if the image of the virtual object used for rehabilitation of higher brain dysfunction exists in the real space,
the computer program causes the processor to perform the rehabilitation of higher brain dysfunction by executing the at least one app using a mixed reality while the computer program causes the processor to perform a drawing process,
the drawing process includes:
detecting the position and the inclination of the image processing apparatus on the three-dimensional data of the space on the basis of information from the first sensor;
detecting the orientation of the user on the three-dimensional data of the space on the basis of information from the second sensor;
placing the three-dimensional data of the virtual object on the three-dimensional data of the space in accordance with the current position and inclination of the image processing apparatus and the orientation of the user; and
visually presenting the generated image of the virtual object on a mixed reality-specific display unit of the image processing apparatus,
the at least one app sets the problem eliminating or changing the image of the virtual object in accordance with an input from the user, and
the input from the user includes at least one of an input from a wired or wireless switch or a touchscreen included in the image processing apparatus, a gesture of the user detected by the camera, or the line of sight of the user at a fixed point for a fixed period of time, which is detected by the second sensor.

40. A head mounted display comprising:
a recording medium that stores at least one app for presenting a user wearing the head mounted display a problem for rehabilitation of higher brain dysfunction;
a wired or wireless switch or a touchscreen;
a camera;
a spatial recognition unit configured to process a data obtained by the camera, an infrared sensor or a laser irradiation to recognize a three-dimensional shape of a surrounding space of the head mounted display, and convert the three-dimensional shape of the space into three-dimensional data;
a first sensor structurally included in a housing of the head mounted display or attached to an outside of the housing, and configured to detect a position and an inclination of the head mounted display in the space recognized by the spatial recognition unit;
a second sensor configured to detect an orientation of the user including a line of sight of the user;
an image processor configured to store, in the storage unit, the three-dimensional data of the space, three-dimensional data of a virtual object, three-dimensional data of the position and inclination of the head mounted display detected by the first sensor, and three-dimensional data of the orientation of the user detected by the second sensor with the same coordinate axes, place the virtual object in the space recognized by the spatial recognition unit on the same coordinate axes, and generate an image of the virtual object visible to the user on the basis of the position and inclination of the head mounted display detected by the first sensor and the orientation of the user detected by the second sensor; and
mixed reality-specific displays for left and right eyes, configured to visually present the image of the virtual object generated by the image processor for the user as if the image generated by the image processor exists in a real space, wherein the head mounted display further comprises a processor configured to generate the problem as if the image of the virtual object used for rehabilitation of higher brain dysfunction exists in the real space, the head mounted display performs the rehabilitation of higher brain dysfunction by executing the at least one app using a mixed reality while the image processor performs a drawing process, the drawing process includes:

detecting the position and the inclination of the head mounted display on the three-dimensional data of the space on the basis of information from the first sensor;

detecting the orientation of the user on the three-dimensional data of the space on the basis of information from the second sensor;

placing the three-dimensional data of the virtual object on the three-dimensional data of the space in accordance with the current position and inclination of the head mounted display and the orientation of the user; and visually presenting the generated image of the virtual object on the mixed reality-specific display unit, the at least one app sets the problem eliminating or changing the image of the virtual object in accordance with an input from the user, and the input from the user includes an input from the wired or wireless switch or the touchscreen, a gesture of the user detected by the camera, or the line of sight of the user at a fixed point for a fixed period of time, which is detected by the second sensor.

* * * * *